(12) United States Patent
Jaroch et al.

(10) Patent No.: US 6,897,224 B2
(45) Date of Patent: May 24, 2005

(54) QUINOLINE AND ISOQUINOLINE DERIVATIVES, A PROCESS FOR THEIR PRODUCTION AND THEIR USE AS INFLAMMATION INHIBITORS

(75) Inventors: Stefan Jaroch, Berlin (DE); Manfred Lehmann, Berlin (DE); Norbert Schmees, Berlin (DE); Markus Berger, Berlin (DE); Hartmut Rehwinkel, Berlin (DE); Konrad Krolikiewicz, Berlin (DE); Werner Skuballa, Berlin (DE); Heike Schäecke, Berlin (DE); Arndt. J. G. Schottelius, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/405,033

(22) Filed: Apr. 2, 2003

(65) Prior Publication Data

US 2004/0116694 A1 Jun. 17, 2004

Related U.S. Application Data

(60) Provisional application No. 60/369,583, filed on Apr. 4, 2002.

(30) Foreign Application Priority Data

Apr. 2, 2002 (DE) .......... 102 15 316

(51) Int. Cl.$^7$ .......... A61K 31/47; A61K 31/5377; C07D 215/40; C07D 217/24; C07D 265/36
(52) U.S. Cl. .......... 514/312; 514/313; 514/311; 514/307; 514/310; 514/235.2; 546/153; 546/157; 546/159; 546/171; 546/141; 546/143; 544/128; 544/105
(58) Field of Search .......... 546/153, 157, 546/159, 171, 141, 143; 544/128, 105; 514/312, 313, 311, 307, 310, 235.2

(56) References Cited

U.S. PATENT DOCUMENTS 6,323,199 B1 11/2001 Lehmann et al.
2002/0077356 A1 * 6/2002 Jaroch .......... 514/522

FOREIGN PATENT DOCUMENTS

WO      WO 0032584 A2    6/2000

OTHER PUBLICATIONS

Aoki et al., "Inhibitory Effect of a Novel Quinolinone Derivative, TA–270, on Asthmatic Inflammatory Responses in Sensitized Guinea Pigs," *European Journal of Pharmacology*, 409 (2000) 325–330.

Search Report for Appl. No. PCT/EP03/03298 completed Jun. 2003.

Written Opinion for Appl. No. PCT/EP03/03298 completed Dec. 2003.

* cited by examiner

*Primary Examiner*—Evelyn Mei Huang
(74) *Attorney, Agent, or Firm*—Millen, White, Zelano & Branigan, P.C.

(57) ABSTRACT

The invention relates to quinoline and isoquinoline derivatives of general formula I

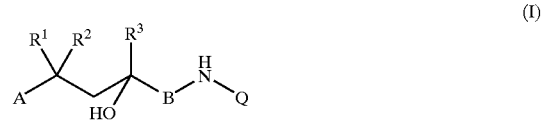

(I)

a process for their production and their use as inflammation inhibitors.

20 Claims, No Drawings

QUINOLINE AND ISOQUINOLINE DERIVATIVES, A PROCESS FOR THEIR PRODUCTION AND THEIR USE AS INFLAMMATION INHIBITORS

This application claims the benefit of the filing date of U.S. Provisional Application Ser. No. 60/369,583 filed Apr. 4, 2002.

The invention relates to quinoline and isoquinoline derivatives, a process for their production and their use as inflammation inhibitors.

From the prior art of DE 100 38 639 and WO02/10143, inflammation inhibitors of the general formula

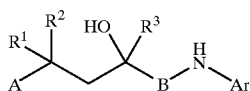
(I)

are known, whereby the Ar radical comprises phthalides, thiophthalides, benzoxazinones or phthalazinones. In the experiment, these compounds show dissociations of actions between anti-inflammatory actions and undesirable metabolic actions and are superior to the previously described, nonsteroidal glucocorticoids or have at least just as good an action.

The selectivity of the compounds of the prior art relative to the other steroid receptors, however, still requires improvement.

The object of this invention was therefore to make available compounds whose selectivity is improved relative to the other steroid receptors.

This object is achieved by the compounds according to the claims.

This invention therefore relates to compounds of general formula I

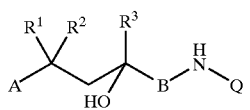
(I)

in which

A stands for an aryl group, a benzyl group or a phenethyl group, whereby the aryl, benzyl or phenethyl group optionally can be substituted by one or more radicals from the group $C_1$–$C_5$-alkyl, $C_1$–$C_5$-alkoxy, $C_1$–$C_5$-alkylthio, $C_1$–$C_5$-perfluoroalkyl, halogen, hydroxy, cyano, nitro, —O—$(CH_2)_n$—O—, —O—$(CH_2)_n$—$CH_2$—, —O—CH═CH—, or —$(CH_2)_{n+2}$—, whereby n=1 or 2, and the terminal oxygen atoms and/or carbon atoms are linked with directly adjacent ring-carbon atoms, or $NR^4R^5$, whereby $R^4$ and $R^5$, independently of one another, can be hydrogen, $C_1$–$C_5$-alkyl or (CO)—$C_1$–$C_5$-alkyl, $R^1$ and $R^2$, independently of one another, mean a hydrogen atom, a methyl or ethyl group or together with the carbon atom the chain of a $C_3$–$C_6$-cycloalkyl ring, $R^3$ means a $C_1$–$C_3$-alkyl group or a $C_1$–$C_3$-alkyl group that is optionally partially or completely fluorinated, B means a methylene group that is optionally substituted by a methyl or ethyl group, or a carbonyl group, and Q means a quinolinyl group or isoquinolinyl group that is linked via any position and that optionally can be substituted by one or more radicals from the group $C_1$–$C_5$-alkyl, which optionally can be substituted by 1–3 hydroxy groups and/or 1–3 $COOR^6$ groups, $C_1$–$C_5$-alkoxy, $C_1$–$C_5$-alkylthio, $C_1$–$C_5$-perfluoroalkyl, halogen, hydroxy, a carbonyl-oxygen atom, cyano, nitro or $NR^4R^5$, whereby $R^4$ and $R^5$, independently of one another, can be hydrogen, $C_1$–$C_5$-alkyl or (CO)—$C_1$–$C_5$-alkyl, $COOR^6$, whereby $R^6$ means hydrogen or a $C_1$–$C_5$-alkyl group, (CO)$NR^7R^8$, whereby $R^7$ and $R^8$, independently of one another, mean hydrogen or a $C_1$–$C_5$-alkyl group, or a $(C_1$–$C_5$-alkylene)-O—(CO)—$(C_1$–$C_5)$alkyl group, as well as their racemates or separately present stereoisomers and optionally their physiologically compatible salts.

As group A, the aryl group is preferred.

The aryl group comprises phenyl and naphthyl. Phenyl is preferred.

On the ring, the substituted aryl, benzyl or phenethyl groups carry 1–3 substituents, preferably 2 substituents, in addition to the linkage with the chain.

The following substitution patterns on ring A are a special subject of the invention: 2,5-disubstituted phenyl derivatives and 2,4-disubstituted phenyl derivatives, whereby the 1-position is occupied by the linkage to the chain.

Special subjects of the invention are compounds that on the aryl radical carry one or more substituents that are selected from the group $C_1$–$C_5$-alkyl, $C_1$–$C_5$-alkoxy, $C_1$–$C_5$-perfluoroalkyl, halogen, hydroxy, nitro, —O—$(CH_2)_n$—O—, —O—$(CH_2)_n$—$CH_2$—, —O—CH═CH—, and —$(CH_2)_{n+2}$—, whereby n=1 or 2, and the terminal oxygen atoms and/or carbon atoms are linked to directly adjacent ring-carbon atoms.

Quite especially preferred are compounds of formula I, in which A means a phenyl ring that is substituted by a hydroxy or methoxy group and a halogen group, in addition to the linkage with the chain.

The $C_1$–$C_5$-alkyl groups in A, $R^3$, $R^4$, $R^5$, $R^6$, $R^7$ and $R^8$ can be straight-chain or branched and can stand for a methyl, ethyl, n-propyl, iso-propyl, n-butyl, iso-butyl, tert-butyl or n-pentyl, 2,2-dimethylpropyl, 2-methylbutyl or 3-methylbutyl group. A methyl or ethyl group is preferred. They can optionally be substituted by 1–3 hydroxy groups and/or 1–3 $COOR^6$ groups. Hydroxy groups are preferred.

A $(C_1$–$C_5$-alkylene)-O—(CO)—$(C_1$–$C_5)$alkyl group is defined as, for example, a —$CH_2$—O—CO—$CH_3$ group.

For a partially or completely fluorinated $C_1$–$C_3$-alkyl group, the following partially or completely fluorinated groups are suitable: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred.

Alkyl radicals $R^1$ and $R^2$ together with the carbon atom of the chain can form a 3- to 6-membered ring. The cyclopropyl ring is preferred.

The $C_1$–$C_5$-alkoxy groups in A and Q can be straight-chain or branched and stand for a methoxy, ethoxy, n-propoxy, iso-propoxy, n-butoxy, iso-butoxy, tert-butoxy or n-pentoxy, 2,2-dimethylpropoxy, 2-methylbutoxy or 3-methylbutoxy group. A methoxy or ethoxy group is preferred.

The $C_1$–$C_5$-alkylthio groups in A and Q can be straight-chain or branched and stand for a methylthio, ethylthio, n-propylthio, iso-propylthio, n-butylthio, iso-butylthio, tert-butylthio or n-pentylthio, 2,2-dimethylpropylthio, 2-methylbutylthio or 3-methylbutylthio group. A methylthio group or an ethylthio group is preferred.

The designation halogen atom or halogen means a fluorine, chlorine, bromine or iodine atom. A fluorine, chlorine or bromine atom is preferred.

The NR$^4$R$^5$ group can mean, for example, NH$_2$, N(H)CH$_3$, N(CH$_3$)$_2$, N(H)(CO)CH$_3$, N(CH$_3$)(CO)CH$_3$, N[(CO)CH$_3$]$_2$, N(H)CO$_2$CH$_3$, N(CH$_3$)CO$_2$CH$_3$, or N(CO$_2$CH$_3$)$_2$.

As alkyl radicals R$^4$ and R$^5$, C$_1$–C$_3$-alkyl is preferred.

As acyl radicals R$^4$ and R$^5$, (CO)—C$_1$–C$_3$-alkyl is preferred.

For the NR$^7$R$^8$ group, for example, NH$_2$, N(H)CH$_3$, N(CH$_3$)$_2$, N(C$_2$H$_5$)$_2$, NH(C$_2$H$_5$), N(C$_3$H$_7$)$_2$, N(C$_4$H$_9$)$_2$, and N(C$_5$H$_{11}$)$_2$ are suitable.

For radical B, the unsubstituted methylene group and the carbonyl group are preferred. The methylene group is especially preferred.

Radical Q can be linked via any ring-carbon atom with the (NH) group of the chain. The 4-, 5- and 8-positions are preferred for the quinoline ring, and the 1-position is preferred for the isoquinoline ring.

The subject matter of the invention includes the compounds of general formula I, in which A stands for an aryl group, a benzyl group or a phenethyl group, whereby the aryl, benzyl or phenethyl group optionally can be substituted by one or more radicals from the group C$_1$–C$_5$-alkyl, C$_1$–C$_5$-alkoxy, C$_1$–C$_5$-alkylthio, C$_1$–C$_5$-perfluoroalkyl, halogen, hydroxy, cyano, nitro, —O—(CH$_2$)$_n$—O—, —O—(CH$_2$)$_n$—CH$_2$—, —O—CH=CH—, or —(CH$_2$)$_{n+2}$—, whereby n=1 or 2, and the terminal oxygen atoms and/or carbon atoms are linked with directly adjacent ring-carbon atoms, or NR$^4$R$^5$, whereby R$^4$ and R$^5$, independently of one another, can be hydrogen, C$_1$–C$_5$-alkyl or (CO)—C$_1$–C$_5$-alkyl, R$^1$ and R$^2$, independently of one another, mean a hydrogen atom, a methyl or ethyl group or together with the carbon atom mean the chain of a C$_3$–C$_6$-cycloalkyl ring, R$^3$ means a C$_1$–C$_3$-alkyl group or a C$_1$–C$_3$-alkyl group that is optionally partially or completely fluorinated, B means a methylene group that is optionally substituted by a methyl or ethyl group, or a carbonyl group, and Q means a quinolinyl group or isoquinolinyl group that is linked via any position and that optionally can be substituted by one or more radicals from the group C$_1$–C$_5$-alkyl, C$_1$–C$_5$-alkoxy, C$_1$–C$_5$-alkylthio, C$_1$–C$_5$-perfluoroalkyl, halogen, hydroxy, cyano, nitro or NR$^4$R$^5$, whereby R$^4$ and R$^5$, independently of one another, can be hydrogen, C$_1$–C$_5$-alkyl or (CO)—C$_1$–C$_5$-alkyl, as well as their racemates or separately present stereoisomers and optionally their physiologically compatible salts.

The subject matter of the invention includes compounds of general formula I in which Q means a quinolinyl group or an isoquinolinyl group that is linked via any position and that optionally can be substituted by one or more radicals from the group C$_1$–C$_5$-alkyl, which optionally can be substituted by 1–3 hydroxy groups or 1–3 COOR$^6$ groups, a carbonyl-oxygen atom, COOR$^6$, whereby R$^6$ means hydrogen or a C$_1$–C$_5$-alkyl group, (CO)NR$^7$R$^8$, whereby R$^7$ and R$^8$, independently of one another, mean hydrogen or a C$_1$–C$_5$-alkyl group, or a (C$_1$–C$_5$-alkyl)-O—(CO)—(C$_1$–C$_5$)alkyl group.

The subject matter of the invention includes compounds of general formula I in which Q represents a quinolinyl group that is substituted in one place.

The subject matter of the invention includes compounds in which B means a methylene group and Q means an optionally substituted quinolinyl group.

The subject matter of the invention includes compounds in which A means an optionally substituted phenyl group, Q means an optionally substituted quinolinyl group, and B means a methylene group.

The compounds of general formula I according to the invention can be present as different stereoisomers by the presence of asymmetry centers. Both the racemates and the separately present stereoisomers are part of the subject of this invention.

A special subject of this invention are the separately present stereoisomers, i.e., (+)-enantiomers and (−)-enantiomers.

The compounds according to the invention, if they contain a hydroxy group in α-position to the quinolinyl or isoquinolinyl-nitrogen atom, are also distinguished by the presence of a keto-enol-tautomerism. In terms according to the invention, both forms are part of the subject of the invention, even if, e.g., in the experimental part, only one of the two tautomeric forms has been cited.

The process for the production of the compounds of WO98/54159, WO00/32584 and WO02/10143 can also be used for the production of the compounds according to the invention. For the linkage of the quinoline or isoquinoline group that is characteristic of the compounds according to the invention, the following process steps can be implemented:

A1)

For B=CO

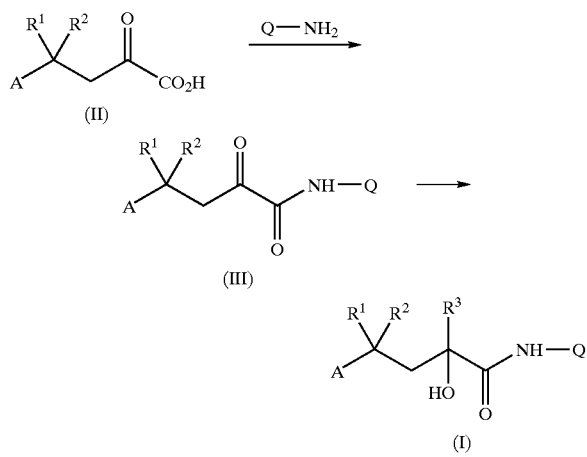

An α-keto acid of general formula (II), in which A, R$^1$ and R$^2$ have the meanings that are indicated for formula (I), is converted with an aminoquinoline, an aminoisoquinoline or a (partially)hydrogenated quinoline or isoquinoline derivative (Q-NH$_2$) into α-ketoamide (III), whereby A, R$^1$, and R$^2$ have the above-indicated meaning, in the way that is known to one skilled in the art. For example, α-ketoamide (III) is obtained with use of dehydrating coupling reagents, as they are known from peptide chemistry, e.g., dicyclohexylcarbodiimide, or by upstream conversion of the acid into an acid chloride, e.g., with thionyl chloride or POCl$_3$ and subsequent reaction with Q-NH$_2$.

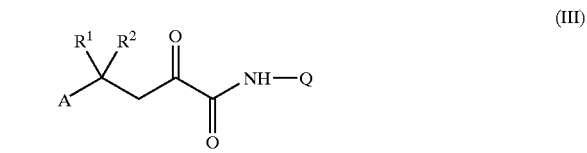

Compound (III) is reacted either with an alkyl metal compound, for example a Grignard reagent or a lithium alkyl, or by reaction with compound (IV),

whereby R³ has the above-indicated meaning and R⁹ refers to a $C_1$–$C_5$-alkyl group, in the presence of a catalyst, e.g., fluoride salts or bases, such as, for example, alkali carbonates (*J. Am. Chem. Soc.* 1989, 111, 393) to form title compound (I).

A2)

For B=CO

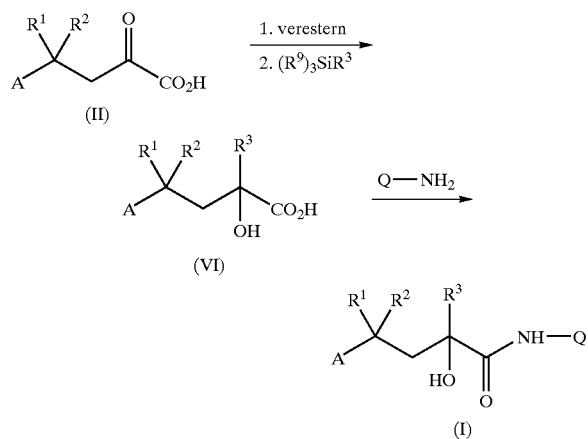

[Key: 1. verestern=1. esterification]

As an alternative, α-keto acids (II) can also be esterified to compounds (V)

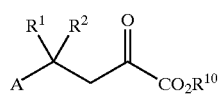

(V)

in which A, R¹, and R² are defined as described above and R¹⁰ is $C_1$–$C_4$-alkyl, according to commonly used methods, e.g., with thionyl chloride in methanol or ethanol or with methyl iodide and alkali carbonate, and can be converted from (III) to (I) in compound (VI) analogously to reaction sequence A1).

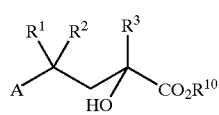

(VI)

The ester is saponified under standard conditions, for example aqueous alkali hydroxide solution, to acid (VI; R¹⁰=H). The latter is reacted in the coupling with an aminoquinoline or aminoisoquinoline or a (partially)-hydrogenated quinoline or isoquinoline derivative (Q-NH₂) with use of a standard activating reagent, e.g., thionyl chloride, optionally in the presence of a catalyst such as dimethylaminopyridine, to form title compound (I).

B)

For B=a methylene group that is optionally substituted by methyl or ethyl

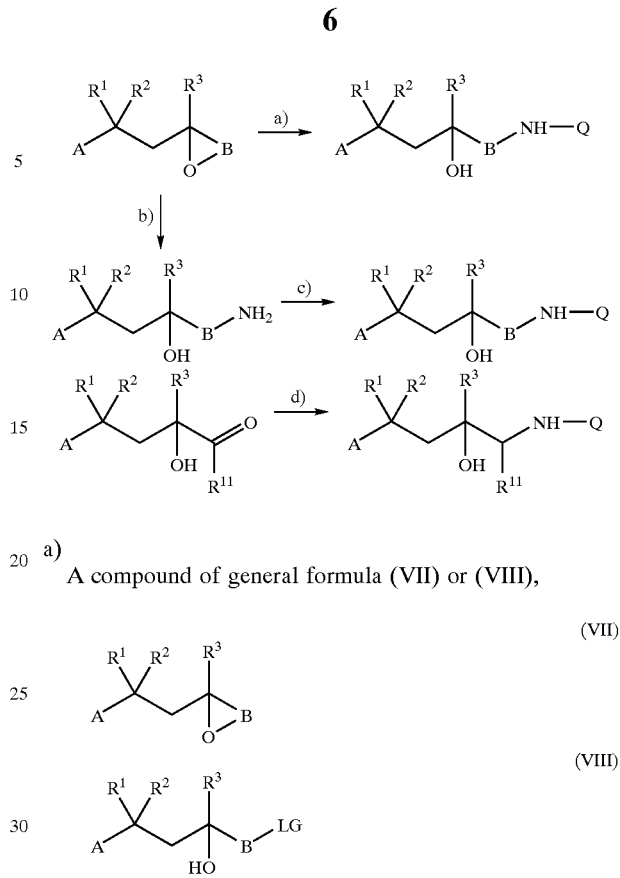

a)

A compound of general formula (VII) or (VIII),

(VII)

(VIII)

in which A, B and R¹, R², and R³ have the above-indicated meaning, and LG means any leaving group such as halide or sulfonate, is reacted with a compound of general formula (IX) or (X)

Q—NH—R¹²                             (IX)

Q—N=C=O                             (X)

in which R¹² means a hydrogen atom, a $C_1$–$C_5$-acyl group or alkoxy- or aryloxycarbonyl group, and Q has the above-indicated meaning, whereby radical R¹² is cleaved off or an intermediately formed oxazolidinone (cf., e.g., S. J. Brickner, D. K. Hutchinson, M. R. Barbachyn, P. R. Manninen, D. A. Ulanowicz, S. A. Garmon, K. C. Grega, S. K. Hendges, D. S. Toops, C. W. Ford, G. E. Zurenko *J. Med. Chem.* 1996, 39, 673) is cleaved with, for example, aqueous alkali hydroxides to obtain title compound (I).

b)

Another method consists in reacting compounds of formula (VII) or (VIII) with nitrogen nucleophiles, for example acid salts or ammonia, whereby in the first case, a reduction follows in the way that is known to one skilled in the art, e.g., with complex hydride reagents, such as lithium aluminum hydride, or by a transition metal-catalyzed hydrogenolysis to obtain compounds of formula (XI).

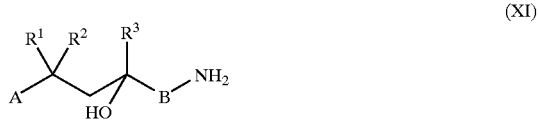

(XI)

As indicated above, radicals R¹–R³, A and B are equally important.

c)
Compound (XI) can be converted under base catalysis, e.g., in the presence of tertiary amine bases or alkali carbonates or alkali hydroxides, or under transition-metal catalysis, e.g., palladium catalysis (J. P. Wolfe, S. Wagaw, J.-F. Marcoux, S. L. Buchwald *Acc. Chem. Res.* 1998, 31, 805; J. F. Hartwig *Acc. Chem. Res.* 1998, 31, 852), with a halogenated quinoline or isoquinoline into title compound (I).

d)
Finally, title compound (I) can also be synthesized by reductive amination of a compound of formula (XII) with Q-NH$_2$, whereby, e.g., sodium cyanoborohydride or sodium triacetoxy borohydride can be considered as a reducing agent.

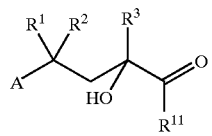

(XII)

$R^{11}$ means methyl or ethyl according to the substituents that are defined for the methylene group in B.

In the case that the compounds of general formula I are present as salts, this can be, for example, in the form of hydrochloride, sulfate, nitrate, phosphate, pivalate, maleate, fumarate, tartrate, benzoate, mesylate, citrate or succinate.

If the compounds according to the invention are present as racemic mixtures, they can be separated into the pure, optically active forms according to the methods of racemate separation that are familiar to one skilled in the art. For example, the racemic mixtures can be separated into pure isomers by chromatography on an even optically active carrier material (CHIRALPAK AD®). It is also possible to esterify the free hydroxy group in a racemic compound of general formula I with an optically active acid and to separate the diastereoisomeric esters that are obtained by fractionated crystallization or by chromatography and to saponify the separated esters in each case to the optically pure isomers. As optically active acid, for example, mandelic acid, camphorsulfonic acid or tartaric acid can be used.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses that code for the GR, are used for the binding studies. In comparison to the reference substance [$^3$H]-dexamethasone, the substances show a high to very high affinity to GR.

Moreover, the quinolines and isoquinolines of formula (I) that are described here show a high selectivity for the glucocorticoid receptor. Example 4 thus shows, e.g., the following profile: IC$_{50}$(GR)=0.6–1.3 nM; IC$_{50}$(MR), IC$_{50}$(PR), IC$_{50}$(AR)>1 μM.

The GR-mediated inhibition of the transcription of cytokines, adhesion molecules, enzymes and other pro-inflammatory factors is considered as an essential, molecular mechanism for the anti-inflammatory action of glucocorticoids. This inhibition is produced by an interaction of the GR with other transcription factors, e.g., AP-1 and NF-kappa-B (for an overview, see Cato, A. C. B. and Wade, E., BioEssays 18, 371–378, 1996).

The compounds of general formula I according to the invention inhibit the secretion of the cytokine IL-8, triggered by lipopolysaccharide (LPS), in the human monocyte cell line THP-1. The concentration of the cytokines was determined in the supernatant by means of commercially available ELISA kits.

The anti-inflammatory action of the compounds of general formula I was tested in the animal experiment by tests in the croton-oil-induced inflammation in rats and mice (J. Exp. Med. (1995), 182, 99–108). To this end, croton oil in ethanolic solution was administered topically to the animals' ears. The test substances were also administered topically or systemically at the same time or two hours before the croton oil. After 16–24 hours, the ear weight was measured as a measurement for the inflammatory edema, the peroxidase activity as a measurement for the invasions of granulocytes and the elastase activity as a measurement for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf. Hatz, H. J., Glucocorticoide: Immunologische Grundlagen, Pharmakologie und Therapierichtlinien [Glucocorticoids: Immunological Principles, Pharmacology and Therapy Guidelines], Wissenschaftliche Verlagsgesellschaft mbH, Stuttgart, 1998]. The reason for this is the stimulation of gluconeogenesis in the liver by induction of the enzymes that are responsible for this and by free amino acids that are produced from the degradation of proteins (catabolic action of glucocorticoids). A key enzyme of the catabolic metabolism in the liver is the tyrosine aminotransferase (TAT). The activity of this enzyme can be determined photometrically from liver homogenates and represents a good measurement for the undesirable metabolic actions of the glucocorticoids. For measurement of TAT induction, the animals are sacrificed 8 hours after the test substances are administered, the livers are removed, and the TAT activity in the homogenate is measured. In this test, at doses at which they have an anti-inflammatory action, the compounds of general formula I induce little or no tyrosine aminotransferase.

Based on their anti-inflammatory action and, in addition, anti-allergic, immunosuppressive and anti-proliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:

Chronic, obstructive lung diseases of any origin, primarily bronchial asthma

Bronchitis of different origins

All forms of restrictive lung diseases, primarily allergic alveolitis,

All forms of pulmonary edema, primarily toxic pulmonary edema

Sarcoidoses and granulomatoses, especially Boeck's disease (ii) Rheumatic diseases/autoimmune diseases/joint diseases that are accompanied by inflammatory, allergic and/or proliferative processes:

All forms of rheumatic diseases, especially rheumatoid arthritis, acute rheumatic fever, polymyalgia rheumatica Reactive arthritis Inflammatory soft-tissue diseases of other origins Arthritic symptoms in the case of degenerative joint diseases (arthroses)

Traumatic arthritides

Collagenoses of any origin, e.g., systemic lupus erythematodes, sclerodermia, polymyositis, dermatomyositis, Sjögren's syndrome, Still's syndrome, Felty's syndrome (iii) Allergies that are accompanied by inflammatory and/or proliferative processes:

All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (vasculitides)

Panarteritis nodosa, arteritis temperalis, erythema nodosum (v) Dermatological diseases that are accompanied by inflammatory, allergic and/or proliferative processes:

Atopic dermatitis (primarily in children)

Psoriasis

Pityriasis rubra pilaris

Erythematous diseases, triggered by different noxae, e.g., radiation, chemicals, burns, etc.

Bullous dermatoses

Diseases of the lichenoid group,

Pruritis (e.g., of allergic origin)

Seborrheal eczema

Rosacea

Pemphigus vulgaris

Erythema exudativum multiforme

Balanitis

Vulvitis

Hair loss such as alopecia areata

Cutaneous T-cell lymphoma (vi) Kidney diseases that are accompanied by inflammatory, allergic and/or proliferative processes:

Nephrotic syndrome

All nephritides (vii) Liver diseases that are accompanied by inflammatory, allergic and/or proliferative processes:

Acute liver cell decomposition

Acute hepatitis of different origins, e.g., viral, toxic, pharmaceutical agent-induced Chronic aggressive hepatitis and/or chronic intermittent hepatitis (viii) Gastrointestinal diseases that are accompanied by inflammatory, allergic and/or proliferative processes:

Regional enteritis (Crohn's disease)

Colitis ulcerosa

Gastritis

Reflux esophagitis

Ulcerative colitis of other origins, e.g., native sprue (ix) Proctologic diseases that are accompanied by inflammatory, allergic and/or proliferative processes:

Anal eczema

Fissures

Hemorrhoids

Idiopathic proctitis (x) Eye diseases that are accompanied by inflammatory, allergic and/or proliferative processes:

Allergic keratitis, uveitis, iritis

Conjunctivitis

Blepharitis

Optic neuritis

Chorioiditis

Sympathetic ophthalmia (xi) Diseases of the ear-nose-throat area that are accompanied by inflammatory, allergic and/or proliferative processes:

Allergic rhinitis, hay fever

Otitis extema, e.g., caused by contact dermatitis, infection, etc.

Otitis media (xii) Neurological diseases that are accompanied by inflammatory, allergic and/or proliferative processes:

Cerebral edema, primarily tumor-induced cerebral edema

Multiple sclerosis

Acute encephalomyelitis

Meningitis

Various forms of convulsions, e.g., infantile nodding spasms (xiii) Blood diseases that are accompanied by inflammatory, allergic and/or proliferative processes:

Acquired hemolytic anemia

Idiopathic thrombocytopenia (xiv) Tumor diseases that are accompanied by inflammatory, allergic and/or proliferative processes:

Acute lymphatic leukemia

Malignant lymphoma

Lymphogranulomatoses

Lymphosarcoma

Extensive metastases, mainly in breast, bronchial and prostate cancers (xv) Endocrine diseases that are accompanied by inflammatory, allergic and/or proliferative processes:

Endocrine orbitopathy

Thyreotoxic crisis

De Quervain's thyroiditis

Hashimoto's thyroiditis

Basedow's disease (xvi) Organ and tissue transplants, graft-versus-host disease (xvii) Severe shock conditions, e.g., anaphylactic shock, systemic inflammatory response syndrome (SIRS)

(xviii) Substitution therapy in:

Innate primary suprarenal insufficiency, e.g., congenital adrenogenital syndrome Acquired primary suprarenal insufficiency, e.g., Addison's disease, autoimmune adrenalitis, meta-infective tumors, metastases, etc.

Innate secondary suprarenal insufficiency, e.g., congenital hypopituitarism

Acquired secondary suprarenal insufficiency, e.g., meta-infective tumors, etc.

(xix) Vomiting that is accompanied by inflammatory, allergic and/or proliferative processes:

e.g., in combination with a 5-HT3 antagonist in cytostatic-agent-induced vomiting (xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

The invention additionally provides:
(i) The use of one of the compounds of general formula I according to the invention or mixture thereof for the production of a medication for treating a DISEASE;
(ii) A process for treating a DISEASE, said process comprises an administration of an amount of the compound according to the invention whereby the amount suppresses the disease and whereby the amount of compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 μg to 100,000 μg of the compound according to the invention per kg of body weight. In the case of larger mammals, for example the human, a recommended daily dose lies in the range of 1 μg to 100,000 μg per kg of body weight. Preferred is a dose of 10 to 30,000 μg per kg of body weight, and more preferred is a dose of 10 to 10,000 μg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles that are commonly used in galencials, fillers, substances that influence decomposition, binding agents, moisturizers, lubricants, absorbents, diluents, flavoring correctives, coloring agents, etc., and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%–20% in these preparations to achieve a sufficient pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixture thereof or pharmaceutically compatible salt thereof and a pharmaceutically compatible salt or pharmaceutically compatible adjuvants and vehicles.

The examples below are used for a more detailed explanation of the invention without intending that it be limited thereto. The syntheses of important precursors, which are not disclosed within the scope of the experiments, are already prior art and can be derived from, for example, WO 98/54159 and WO 02/10143.

EXPERIMENTS

Example 1

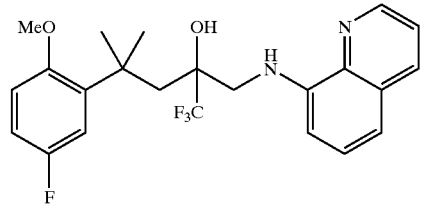

1-(Quinolin-8-ylamino)-4-(5-fluoro-2-methoxyphenyl)-4-methyl-2-(trifluoromethyl)pentan-2-ol 200 mg (0.68 mmol) of 2-[2-(5-fluoro-2-methoxyphenyl)-2-methylpropyl]-2-(trifluoromethyl)oxirane (WO 00/32584) and 99 mg (0.68 mmol) of 8-aminoquinoline are heated in 0.2 ml of 3,4,5,6-tetrahydro-2-(1H)-pyrimidone (DMPU) for 20 hours to 130° C. After the reaction mixture is purified on silica gel with hexane-ethyl acetate (0–20%), 230 mg of the product is obtained.

$^1$H-NMR (CDCl$_3$): δ=1.47 (s, 3H), 1.65 (s, 3H), 2.25 (d, 1H), 2.85 (d, 1H), 3.30 (AB-system, 2H), 3.85 (s, 3H), 6.13 (br., d, 1H), 6.80 (dd, 1H), 6.95 (ddd, 1H), 7.13 (d, 1H), 7.20 (dd, 1H), 7.32 (z, 1H), 7.45 (m, 1H), 8.18 (m, 1H), 8.72 (dd, 1H).

Example 2

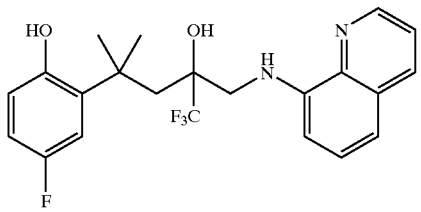

1-(Quinolin-8-ylamino)-4-(5-fluoro-2-hydroxyphenyl)-4-methyl-2-(trifluoromethyl)pentan-2-ol 200 mg (0.46 mmol) of 1-(quinolin-8-ylamino)-4-(5-fluoro-2-methoxyphenyl)-4-methyl-2-(trifluoromethyl) pentan-2-ol in 20 ml of $CH_2Cl_2$ is mixed at 0° C. with 9 ml of 1 M boron tribromide-$CH_2Cl_2$ solution. After 20 hours at room temperature, the batch is poured into saturated $NaHCO_3$ solution, stirred for 20 minutes and extracted with $CH_2Cl_2$. The combined organic extracts are washed with water, dried ($Na_2SO_4$) and concentrated by evaporation in a vacuum. Chromatography with hexane-ethyl acetate (0–25%) on silica gel yields 190 mg of the product.

$^1$H-NMR (CDCl$_3$): δ=1.48 (s, 3H), 1.62 (s, 3H), 2.20 (d, 1H), 3.18 (d, 1H), 3.35 (s, 2H), 6.45 (d, 1H), 6.52 (dd, 1H), 6.65 (ddd, 1H), 7.08 (dd, 1H), 7.15 (d, 1H), 7.35 (t, 1H), 7.50 (dd, 1H), 8.25 (d, 1H), 8.83 (dd, 1H).

Example 3

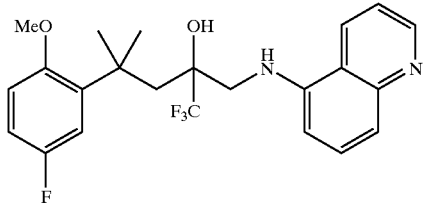

1-(Quinolin-5-ylamino)-4-(5-fluoro-2-methoxyphenyl)-4-methyl-2-(trifluoromethyl)pentan-2-ol Analogously to Example 1, 200 mg (0.48 mmol) of 2-[2-(5-fluoro-2-methoxyphenyl)-2-methylpropyl]-2-(trifluoromethyl)oxirane is reacted with 99 mg (0.68 mmol) of 5-aminoquinoline. After chromatography on silica gel with hexane-ethyl acetate (0–70%), 58 mg of the product is obtained.

$^1$H-NMR (CDCl$_3$): δ=1.47 (s, 3H), 1.56 (s, 3H), 2.38 (d, 1H), 2.78 (d, 1H), 3.15 (dd, 1H), 3.33 (dd, 1H), 3.85 (s, 3H), 4.65 (br., 1H), 6.10 (d, 1H), 6.80 (dd, 1H), 6.93 (ddd, 1H), 7.10 (dd, 1H), 7.37 (dd, 1H), 7.50 (t, 1H), 7.61 (d, 1H), 8.18 (d, 1H), 6.80 (dd, 1H).

Example 4

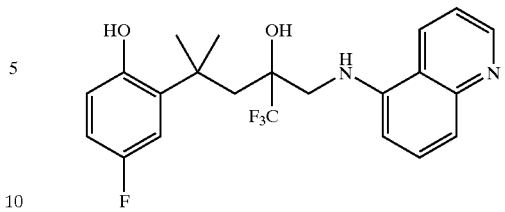

1-(Quinolin-5-ylamino)-4-(5-fluoro-2-methoxyphenyl)-4-methyl-2-(trifluoromethyl)pentan-2-ol Analogously to Example 2, 58 mg (0.13 mmol) of 1-(quinolin-5-ylamino)-4-(5-fluoro-2-methoxyphenyl)-4-methyl-2-(trifluoromethyl)pentan-2-ol in 6 ml of $CH_2Cl_2$ is reacted with 2.6 ml of 1 M boron tribormide-$CH_2Cl_2$ solution. After chromatography on silica gel with hexane-ethyl acetate (0–70%), 22 mg of the product is obtained.

$^1$H-NMR (CDCl$_3$): δ=1.48 (s, 3H), 1.54 (s, 3H), 2.45 (d, 1H), 2.82 (d, 1H), 3.20 (dd, 1H), 3.40 (dd, 1H), 5.05 (br., 1H), 6.25 (d, 1H), 6.70 (m, 1H), 6.85 (dd, 1H), 6.95 (dd, 1H), 7.45 (dd, 1H), 7.53 (d, 1H), 7.58 (d, 1H), 8.32 (d, 1H), 8.68 (d, 1H).

Example 5

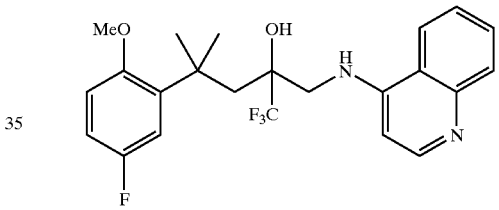

1-(Quinolin-4-ylamino)-4-(5-fluoro-2-methoxyphenyl)-4-methyl-2-(trifluoromethyl)pentan-2-ol 1-Amino-4-(5-fluoro-2-methoxyphenyl)-4-methyl-2-(trifluoromethyl)propan-2-ol 1.0 g (3.4 mmol) of 2-[2-(5-fluoro-2-methoxyphenyl-2-methylpropyl]-2-(trifluoromethyl)oxirane in 68 ml of THF is refluxed with 1.1 g of sodium azide and 180 mg of ammonium chloride in 14 ml of water and 26 ml of ethanol for 6 hours. The batch is concentrated by evaporation, diluted with ether, washed with water, dried ($Na_2SO_4$) and concentrated by evaporation. Chromatography on silica gel with hexane-ethyl acetate (0–15%) yields 950 mg of 1-azido-4-(5-fluoro-2-methoxphenyl)-4-methyl-2-(trifluoromethyl)propan-2-ol. The latter is dissolved in 29 ml of THF and mixed in portions at 0° C. with 270 mg of lithium aluminum hydride. After 1 hour, the batch is treated with ethyl acetate and water and filtered on Celite. The ethyl acetate phase is dried ($Na_2SO_4$) and concentrated by evaporation in a vacuum. 920 mg of amine is obtained.

$^1$H-NMR (CDCl$_3$): δ=1.4 (s, 3H), 1.5 (s, 3H), 2.15 (d, 1H), 2.45 (d, 1H), 2.55 (d, 1H), 2.75 (d, 1H), 2.80 (m), 3.8 (s, 3H), 6.8 (dd, 1H), 6.9 (td, 1H), 7.05 (dd, 1H).

1-(Quinolin-4-ylamino)-4-(5-fluoro-2-methoxyphenyl)-4-methyl-2-(trifluoromethyl)pentan-2-ol 500 mg (1.6 mmol) of 1-amino-4-(5-fluoro-2-methoxyphenyl)-4-methyl-2-(trifluoromethyl)propan-2-ol, 265 mg (1.6 mmol) of 4-chloroquinoline and 183 mg (1.6 mmol) of diazabicyclo-[2.2.2]octane are heated for 3 hours to 150° C. The batch is dissolved in $CH_2Cl_2$ and water. The aqueous phase is extracted with $CH_2Cl_2$, the combined organic extracts are washed with water, dried ($Na_2SO_4$) and concentrated by evaporation in a vacuum. Chromatography on silica gel with $CH_2Cl_2$-methanol (0–10%) yields 305 mg of product.

$^1$H-NMR ($D_6$-DMSO): δ=1.40 (s, 3H), 1.57 (s, 3H), 2.10 (d, 1H), 2.88 (d, 1H), 3.05 (dd, 1H), 3.15 (dd, 1H), 3.80 (s, 3H), 5.96 (d, 1H), 6.00 (s, 1H), 6.26 (br. t, 1H), 6.98 (d, 1H), 7.02 (td, 1H), 7.10 (dd, 1H), 7.45 (t, 1H), 7.60 (t, 1H), 7.77 (d, 1H), 7.95 (d, 1H), 8.30 (d, 1H).

Example 6

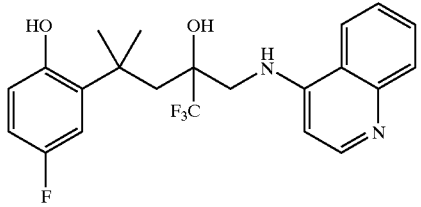

1-(Quinolin-4-ylamino)-4-(5-fluoro-2-hydroxyphenyl)-4-methyl-2-(trifluoromethyl)pentan-2-ol Analogously to Example 2, 200 mg (0.46 mmol) of 1-(quinolin-4-ylamino)-4-(5-fluoro-2-methoxyphenyl)-4-methyl-2-(trifluoromethyl)pentan-2-ol and 9 ml of 1 M boron tribromide-$CH_2Cl_2$ solution are reacted. After chromatography on silica gel with $CH_2Cl_2$-methanol (0–15%), 138 mg of product is obtained.

$^1$H-NMR ($D_6$-DMSO): δ=1.40 (s, 3H), 1.58 (s, 3H), 1.95 (d, 1H), 3.00–3.50 (m, 3H), 6.05 (m+d, 2H), 6.65 (br., 1H), 6.80 (dd, 1H), 6.86 (td, 1H), 7.05 (dd, 1H), 7.50 (t, 1H), 7.65 (t, 1H), 7.80 (d, 1H), 8.02 (d, 1H), 8.32 (d, 1H), 9.82 (br., 1H).

Example 7

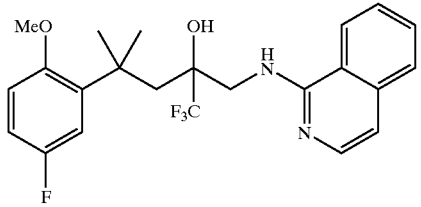

4-(5-Fluoro-2-methoxyphenyl)-1-(isoquinolin-1-ylamino)-4-methyl-2-(trifluoromethyl)pentan-2-ol Analogously to Example 1, 200 mg (0.68 mmol) of 2-[2-(5-fluoro-2-methoxyphenyl)-2-methylpropyl]-2-(trifluoromethyl)oxirane and 99 mg (0.68 mmol) of 1-aminoisoquinoline are reacted. After chromatography on silica gel with hexane-ethyl acetate (0–60%), 65 mg of product is obtained.

$^1$H-NMR (CDCl$_3$): δ=1.45 (s, 3H), 1.72 (s, 3H), 2.40 (d, 1H), 3.00 (d, 1H), 3.40 (d, 1H), 3.88 (s, 3H), 4.23 (d, 1H), 6.40 (d, 1H), 6.63 (d, 1H), 6.82 (dd, 1H), 6.89 (td, 1H), 7.15 (dd, 1H), 7.45 (d, 1H), 7.55 (t, 1H), 7.65 (t, 1H), 8.45 (br., 1H).

Example 8

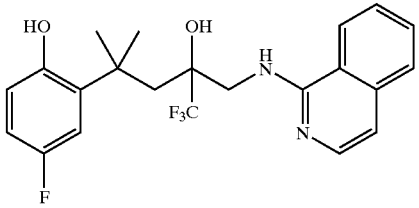

4-(5-Fluoro-2-hydroxyphenyl)-1-(isoquinoline-1-ylamino)-4-methyl-2-(trifluoromethyl)pentan-2-ol Analogously to Example 2, 65 mg (0.15 mmol) of 4-(5-fluoro-2-methoxyphenyl)-1-(isoquinolin-1-ylamino)-4-methyl-2-(trifluoromethyl)pentan-2-ol is reacted with 2.7 ml of 1 M boron tribromide-$CH_2Cl_2$ solution. After chromatography on silica gel with hexane-ethyl acetate (0–80%), 33 mg of the product is obtained.

$^1$H-NMR (CDCl$_3$): δ=1.40 (s, 3H), 1.60 (s, 3H), 2.00 (d, 1H), 2.87 (d, 1H), 3.53 (d, 1H), 4.23 (d, 1H), 6.25 (d, 1H), 6.70–6.90 (m, 3H), 7.00 (dd, 1H), 7.42 (t, 1H), 7.48 (d, 1H), 7.58 (t, 1H), 8.05 (br., 1H), 8.22 (d, 1H), 9.80 (br., 2H).

Example 9

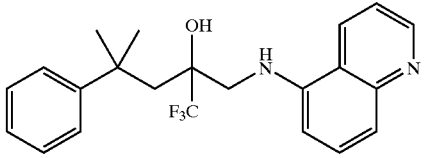

1-(Quinolin-5-ylamino)-4-methyl-4-phenyl-2-(trifluoromethyl)pentan-2-ol 2-(2-Methyl-2-phenylpropyl)-2-(trifuoromethyl)oxirane 10.4 g of 4-methyl-2-oxo-4-phenylpentanoic acid (WO98/54159) in 250 ml of dimethylformamide is mixed at −5° C. with 4.1 ml of thionyl chloride and after 15 minutes with 4 ml of methanol. After 15 hours at room temperature, the batch is diluted with water and extracted with ethyl acetate. The organic extracts are washed with water, dried ($Na_2SO_4$) and concentrated by evaporation, whereby 9.3 g of 4-methyl-2-oxo-4-phenylpentanoic acid-methyl ester is obtained. The latter is mixed in 558 ml of DMF at −5° C. with 15.5 ml (104.63 mmol) of (trifluoromethyl) trimethylsilane and 20.5 g (63.28 mmol) of cesium carbonate and stirred for 16 hours at room temperature. Water is added, extracted with ethyl acetate, the organic phase is washed with water and dried ($Na_2SO_4$). The intermediate product that is concentrated by evaporation is taken up in 200 ml of THF and 50 ml of a 1 M solution of tetrabutylammonium fluoride in THF is added. It is stirred for 2 hours, water is added, extracted with ethyl acetate, the organic phase is washed with water and dried ($Na_2SO_4$). After chromatography on silica gel with hexane-ethyl acetate (0–30%), 8.35 g of 2-hydroxy-4-methyl-4-phenyl-2-(trifluoromethyl)pentanoic acid-methyl ester is obtained. The ester (8.3 g, 28.59 mmol) is dissolved in 180 ml of THF, and 1.52 g (36.20 mmol) of lithium aluminum hydride is added in small portions over a period of 2.5 hours. After complete conversion, 5 ml of ethyl acetate is added in drops, and after another 10 minutes, 10 ml of water is carefully added. The formed precipitate is filtered out and washed carefully with ethyl acetate. After chromatography on silica gel with hexane-ethyl acetate (0–35%), 5.40 g of 4-methyl-4-phenyl-2-(trifluoromethyl)pentane-1,2-diol is obtained. 5.6 g (21.35 mmol) of triphenylphosphine and, while being cooled with ice, 4.3 ml (27.31 mmol) of azodicarboxylic acid-diethyl ester are added to diol (5.40 g, 20.59 mmol) in 43 ml of THF. The reaction mixture is refluxed for 3 hours and, after cooling, it is concentrated by evaporation. After chromatography on silica gel with hexane-ethyl acetate (0–15%), 4.18 g of product is obtained.

$^1$H-NMR (CDCl$_3$): δ=1.37 (s, 3H), 1.41 (s, 3H), 2.20 (m, 1H), 2.27 (d, 1H), 2.55 (d, 1H), 2.67 (d, 1H), 7.18–7.35 (m, 5H).

1-(Quinolin-5-ylamino)-4-methyl-4-phenyl-2-(trifluoromethyl)pentan-2-ol

Analogously to Example 1, 300 mg (1.22 mmol) of 2-(2-methyl-2-phenylpropyl)-2-(trifluoromethyl)oxirane and 882 mg (6.12 mmol) of 5-aminoquinoline are reacted. After chromatography on silica gel with hexane-ethyl acetate (0–75%), 85 mg of product is obtained.

$^1$H-NMR (CDCl$_3$): δ=1.45 (s, 3H), 1.60 (s, 3H), 2.30 (d, 1H), 2.36 (d, 1H), 3.02 (dd, 1H), 3.05 (s, 1H), 3.25 (dd, 1H), 4.24 (dd, 1H), 6.11 (d, 1H), 7.28–7.56 (m, 8H), 8.04 (d, 1H), 8.86 (dd, 1H).

Example 10

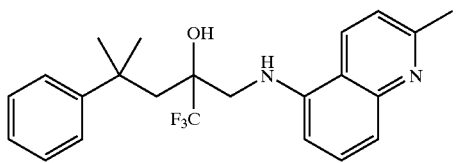

4-Methyl-1-(2-methylquinolin-5-ylamino)-4-phenyl-2-(trifluoromethyl)pentan-2-ol

Analogously to Example 1, 500 mg (2.05 mmol) of 2-(2-methyl-2-phenylpropyl)-2-(trifluoromethyl)oxirane and 650 mg (4.10 mmol) of 5-amino-2-methylquinoline are reacted. After chromatography on silica gel with hexane-ethyl acetate (0–70%), 485 mg of product is obtained.

$^1$H-NMR (CDCl$_3$): δ=1.44 (s, 3H), 1.59 (s, 3H), 2.30 (d, 1H), 2.35 (d, 1H), 2.72 (s, 3H), 3.01 (dd, 1H), 3.04 (s, 1H), 3.23 (dd, 1H), 4.18 (dd, 1H), 6.04 (d, 1H), 7.21 (d, 1H), 7.30 (dt, 1H), 7.37–7.51 (m, 6H), 7.92 (d, 1H).

Example 11

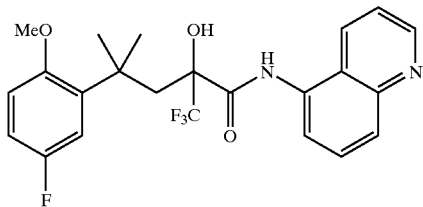

N-(Quinolin-5-yl)-4-(5-fluoro-2-methoxyphenyl)-2-hydroxy-4-methyl-2-(trifluoromethyl)pentanoic acid amide 540 mg (2.13 mmol) of 4-(5-fluoro-2-methoxyphenyl)-4-methyl-2-oxopentanoic acid (WO 00/32584) in 15 ml of DMF is mixed at −5° C. under argon with 0.18 ml of thionyl chloride. After 20 minutes of stirring at −3° C. to +3° C., 470 mg (3.26 mmol) of 5-aminoquinoline is added. It is allowed to heat to room temperature, stirred for another 16 hours, mixed with 10% citric acid, extracted with ethyl acetate, the organic phase is washed with water and dried (Na$_2$SO$_4$). After chromatography on silica gel with hexane-ethyl acetate (0–75%), 680 mg of N-(quinolin-4-yl)-4-(5-fluoro-2-methoxyphenyl)-4-methyl-2-oxopentanoic acid amide is obtained, which is dissolved in 22 ml of DMF and cooled to 0° C. The solution is mixed with 1.80 ml of (trifluoromethyl)trimethylsilane and 2.43 g of cesium carbonate and stirred for 16 hours at room temperature. Water is added, extracted with ethyl acetate, the organic phase is washed with water and dried on sodium sulfate. The intermediate product that is concentrated by evaporation is taken up in 10 ml of THF, and 5.5 ml of a 1 M solution of tetrabutylammonium fluoride is added. It is stirred for 1.5 hours, water is added, extracted with ethyl acetate, the organic phase is washed with water and dried on sodium sulfate. After chromatography on silica gel with hexane-ethyl acetate (0–70%), 420 mg of product is obtained.

$^1$H-NMR (CDCl$_3$): δ=1.44 (s, 3H), 1.46 (s, 3H), 2.80 (d, 1H), 3.10 (d, 1H), 3.57 (s, 1H), 3.89 (s, 3H), 6.81 (dd, 1H), 6.89 (m, 1H), 6.99 (dd, 1H), 7.45 (dd, 1H), 7.73 (t, 1H), 7.95 (d, 1H), 7.99 (d, 1H), 8.00 (d, 1H), 8.83 (br., 1H), 8.95 (dd, 1H).

Example 12

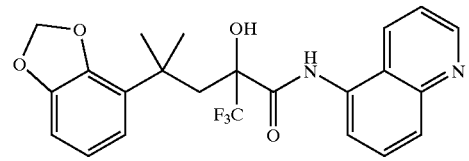

4-(1,3-Benzodioxol-4-yl)-N-(quinolin-5-yl)-2-hydroxy-4-methyl-2-(trifluoromethyl)pentanamide 1,3-Benzodioxol-4-carboxylic acid-methyl ester:

50 g of 2,3-dihydroxybenzoic acid in 450 ml of methanol is mixed at room temperature drop by drop with 50 ml of thionyl chloride. Then, the solution is heated for 5 hours to 60° C. and stirred overnight at room temperature. The solvent is completely removed in a vacuum, and the remaining oil is taken up in diethyl ether and extracted with saturated bicarbonate solution. After washing with brine, drying with sodium sulfate and removal of the solvent in a vacuum, 46 g of 2,3-dihydroxybenzoic acid methyl ester is obtained. The latter is mixed in 575 ml of DMF and 20.2 ml of dibromomethane with 56.7 g of potassium carbonate, and it is heated for 5 hours under argon to 100° C. Then, it is stirred overnight at room temperature. It is then mixed with water and extracted three times with ethyl acetate. The organic phase is washed several times with water and dried on sodium sulfate. The solvent is removed in a vacuum, and 50.2 g of 1,3-benzodioxole-4-carboxylic acid-methyl ester is obtained as a brown solid. Flash point: 55–57° C.

4-(1,3-Benzodioxol-4-yl)-4-methyl-2-oxopentanoic acid 4.76 g of 1,3-benzodioxole-4-carboxylic acid-methyl ester in 65 ml of dry THF is added in drops at room temperature to a solution of 21 ml of 3 M methylmagnesium chloride in THF under argon. It is stirred for 3 hours and then slowly mixed with 1N hydrochloric acid. After extraction with ethyl acetate and after the organic phase is washed with water, it is dried with sodium sulfate, and the solvent is removed in a vacuum. 5.0 g of 1-(1,3-benzodioxol-4-yl)-1-methyl ethanol is obtained as a brown oil. 3.6 g and 5.4 g of 2-(trimethylsilyloxy)-acrylic acid ethyl ester in 80 ml of dichloromethane are mixed at −70° C. with 18 ml of tin tetrachloride. After 15 minutes of stirring at −70° C., the solution is poured onto semi-saturated sodium carbonate solution, mixed with ethyl acetate and vigorously stirred. The phases are separated, and the water phase is extracted twice with ethyl acetate. The organic phase is washed with brine, dried with sodium sulfate, and the solvent is removed in a vacuum. A yellow oil that is mixed with 60 ml of 1N sodium hydroxide solution and 120 ml of methanol and stirred for 3 hours at room temperature is obtained. The methanol is removed in a vacuum, and the water phase is extracted with diethyl ether. Then, the water phase is acidified by adding 120 ml of 1N hydrochloric acid and extracted 3 times with diethyl ether. The ether phase is dried, and the solvent is removed in a vacuum. 4.2 g of 4-(1,3-benzodioxol-4-yl)-4-methyl-2-oxopentanoic acid is obtained as a yellow oil. MS (EI): M$^+$=250 (M=250)

4-(1,3-Benzodioxol-4-yl)-N-(quinolin-5-yl)-4-methyl-2-oxopentanamide 100 mg of 4-(1,3-benzodioxol-4-yl)-4-methyl-2-oxopentanoic acid in 1 ml of dimethyl acetamide is mixed at 0° C. with 0.034 ml of thionyl chloride and stirred for 20 minutes. Then, 61 mg of 5-aminoquinoline is added, and it is stirred overnight at room temperature. It is added to sodium bicarbonate solution and extracted 3 times with ethyl acetate. It is washed with brine, dried, and the solvent is removed in a vacuum. The remaining oil is separated by thick-layer chromatography (silica gel, acetone/hexane 1:1). 25 mg of 4-(1,3-benzodioxol-4-yl)-N-(quinolin-5-yl)-4-methyl-2-oxopentanamide is obtained as a yellow foam. MS (EI): M$^+$=376.3 (M=376.4).

4-(1,3-Benzodioxol-4-yl)-N-(quinolin-5-yl)-2-hydroxy-4-methyl-2-(trifluoromethyl)pentanamide 22 mg of 4-(1,3-benzodioxol-4-yl)-N-(quinolin-5-yl)-4-methyl-2-oxopentanamide and 0.04 ml of trifluoromethyltrimethylsilane in 1 ml of DMF are mixed at 0° C. with 11 mg of cesium carbonate. After 2 hours, a spatula-tip full of tetrabutylammonium fluoride is added, and after another 20 minutes, the reaction is added to water. It is extracted 3 times with ethyl acetate, washed with water and brine, dried, and the solvent is removed in a vacuum. The remaining oil is separated by chromatography on silica gel. 11 mg of 4-(1,3-benzodioxol-4-yl)-N-(quinolin-5-yl)-2-hydroxy-4-methyl-2-(trifluoromethyl)pentanamide is obtained as a solid. Flash point: 164–167° C.

Example 13

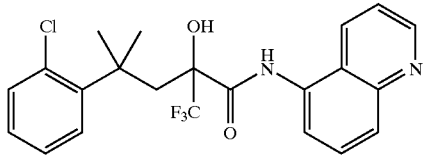

N-(Quinolin-5-yl)-4-(2-chlorophenyl)-2-hydroxy-4-methyl-2-(trifluoromethyl)pentanamide N-(Quinolin-5-yl)-4-(2-chlorophenyl)-4-methyl-2-oxopentanamide According to the instructions for 4-(1,3-benzodioxol-4-yl)-N-(quinolin-5-yl)-4-methyl-2-oxopentanamide after chromatography on silica gel, 152 mg of N-(quinolin-5-yl)-4-(2-chlorophenyl)-4-methyl-2-oxopentanamide is obtained from 200 mg of 4-(2-chlorophenyl)-4-methyl-2-oxopentanoic acid (WO00/32584). MS (EI): M$^+$=366, 368 (3:1); (M=366.8).

N-(Quinolin-5-yl)-4-(2-chlorophenyl)-2-hydroxy-4-methyl-2-(trifluoromethyl)-pentanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 82 mg of N-(quinolin-5-yl)-4-(2-chlorophenyl)-2-hydroxy-4-methyl-2-(trifluoromethyl)pentanamide is obtained from 142 mg of N-(quinolin-5-yl)-4-(2-chlorophenyl)-4-methyl-2-oxopentanamide. Flash point: 210–214° C.

Example 14

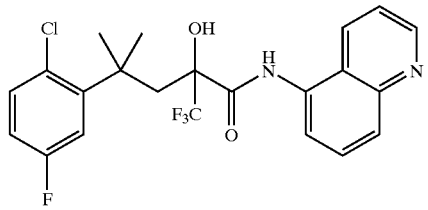

N-(Quinolin-5-yl)-4-(2-chloro-5-fluorophenyl)-2-hydroxy-4-methyl-2-(trifluoromethyl)pentanamide N-(Quinolin-5-yl)-4-(2-chloro-5-fluorophenyl)-4-methyl-2-oxopentanamide According to the instructions for 4-(1,3-benzodioxol-4-yl)-N-(quinolin-5-yl)-4-methyl-2-oxopentanamide (Example 12) after chromatography on silica gel, 400 mg of N-(quinolin-5-yl)-4-(2-chloro-5-fluorophenyl)-4-methyl-2-oxopentanamide is obtained from 520 mg of 4-(2-chloro-5-fluorophenyl)-4-methyl-2-oxopentanoic acid (WO 02/10143). Flash point: 145–146° C.

N-(Quinolin-5-yl)-4-(2-chloro-5-fluorophenyl)-2-hydroxy-4-methyl-2-(trifluoromethyl)pentanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 60 mg of N-(quinolin-5-yl)-4-(2-chloro-5-fluorophenyl)-2-hydroxy-4-methyl-2-(trifluoromethyl)pentanamide is obtained from 384 mg of N-(quinolin-5-yl)-4-(2-chloro-5-fluorophenyl)-4-methyl-2-oxopentanamide. Flash point 188–189° C.

Example 15

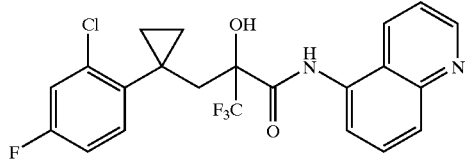

N-(Quinolin-5-yl)-3-[1-(2-chloro-4-fluorophenyl)-cyclopropyl]-2-hydroxy-2-(trifluoromethyl) propanamide N-(Quinolin-5-yl)-3-[1-(2-chloro-4-fluorophenyl)-cyclopropyl]-2-oxopropanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 535 mg of N-(quinolin-5-yl)-3-[1-(2-chloro-4-fluorophenyl)-cyclopropyl]-2-oxopropanamide is obtained as a foam from 512 mg of 3-[1-(2-chloro-4-fluorophenyl)-cyclopropyl]-2-oxopropionic acid (WO 02/10143).

N-(Quinolin-5-yl)-3-[1-(2-chloro-4-fluorophenyl)-cyclopropyl]-2-hydroxy-2-(trifluoromethyl)propanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 200 mg of N-(quinolin-5-yl)-3-[1(-2-chloro-4-fluorophenyl)-cyclopropyl]-2-hydroxy-2-(trifluoromethyl)pentanamide is obtained from 535 mg of N-(quinolin-5-yl)-3-[1-(2-chloro-4-fluorophenyl)-cyclopropyl]-2-oxopropanamide. Flash point: 220–221° C.

Example 16

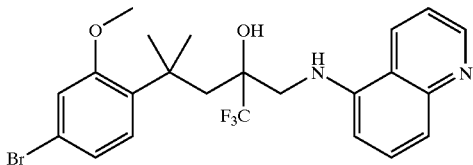

4-(4-Bromo-2-methoxyphenyl)-1-(quinolin-5-ylamino)-2-hydroxy-4-methyl-2-(trifluoromethyl)pentan-2-ol Analogously to Example 1, 200 mg of 2-[2-(4-bromo-2-methoxyphenyl)-2-methylpropyl]-2-(trifluoromethyl)oxirane (WO 00/32585) and 5-aminoquinoline are reacted. After chromatography on silica gel with hexane-ethyl acetate (1+1), 43 mg of 4-(4-bromo-2-methoxyphenyl)-1-(quinolin-5-ylamino)-2-hydroxy-4-methyl-2-(trifluoromethyl)pentan-2-ol is obtained. Flash point: 181° C.

Example 17

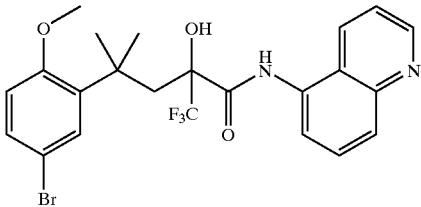

4-(5-Bromo-2-methoxyphenyl)-N-(quinolin-5-yl)-2-hydroxy-4-methyl-2-(trifluoromethyl)pentanamide 1-(5-Bromo-2-methoxyphenyl)-1-methylethanol 62 ml of a 3 M methylmagnesium bromide solution in tetrahydrofuran is added in drops within one hour at 0 C. into 18.6 g of 5-bromo-2-methoxybenzoic acid methyl ester and 180 ml of diethyl ether. After 16 hours at room temperature and while being cooled with ice, it is mixed with saturated ammonium chloride solution and ethyl acetate. The ethyl acetate phase is washed with water, dried (Na$_2$SO$_4$) and concentrated by evaporation. After bulb tube distillation (boiling point: 140° C./0.04 hPa), 16.7 g of crystalline 1-(5-bromo-2-methoxyphenyl)-1-methylethanol is obtained. Flash point: 66–68° C.

4-(5-Bromo-2-methoxyphenyl)-4-methyl-2-oxopentanoic acid-ethyl ester 9.8 g of 1-(5-bromo-2-methoxyphenyl)-1-methylethanol and 15.24 g of 2-(trimethylsilyloxy)-acrylic acid ethyl ester in 150 ml of dichloromethane are mixed at −70° C. with 5.6 ml of tin tetrachloride. After 20 minutes at −70° C., the solution is poured onto a semi-saturated potassium carbonate solution and mixed with dichloromethane. The dichloromethane phase is washed with potassium carbonate solution, 1 M hydrochloric acid and water, dried (Na$_2$SO$_4$) and concentrated by evaporation. After bulb tube distillation, 5.2 g of 4-(5-bromo-2-methoxyphenyl)-4-methyl-2-oxopentanoic acid-ethyl ester is obtained. Boiling point: 160° C./0.04 hPa.

4-(5-Bromo-2-methoxyphenyl)-4-methyl-2-oxopentanoic acid 4-(5-Bromo-2-methoxyphenyl)-4-methyl-2-oxopentanoic acid-ethyl ester in 30 ml of methanol and 12 ml of 1 M sodium hydroxide solution are stirred for 1 hour at room temperature, and the methanol is distilled off. It is mixed with water and hexane, the water phase is acidified with dilute hydrochloric acid while being cooled with ice, and it is mixed with ethyl acetate. The ethyl acetate phase is washed with water, dried (Na$_2$SO$_4$) and concentrated by evaporation. After crystallization from hexane, 1.8 g of 4-(5-bromo-2-methoxyphenyl)-4-methyl-2-oxopentanoic acid is obtained. Flash point: 80° C.

4-(5-Bromo-2-methoxyphenyl)-N-(quinolin-5-yl)-4-methyl-2-oxopentanamide

According to the instructions for 4-(1,3-benzodioxol-4-yl)-N-(quinolin-5-yl)-4-methyl-2-oxopentanamide (Example 12) after chromatography on silica gel, 730 mg of 4-(5-bromo-2-methoxyphenyl)-N-(quinolin-5-yl)-4-methyl-2-oxopentanamide is obtained from 630 mg of 4-(5-bromo-2-methoxyphenyl)-4-methyl-2-oxopentanoic acid. Flash point: 133–135° C.

4-(5-Bromo-2-methoxyphenyl)-N-(quinolin-5-yl)-2-hydroxy-4-methyl-2-(trifluoromethyl)pentanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 484 mg of 4-(5-bromo-2-methoxyphenyl)-N-(quinolin-5-yl)-2-hydroxy-4-methyl-2-(trifluoromethyl)pentanamide is obtained from 617 mg of 4-(5-bromo-2-methoxyphenyl)-N-(quinolin-5-yl)-4-methyl-2-oxopentanamide. Flash point: 243–245° C.

Example 18

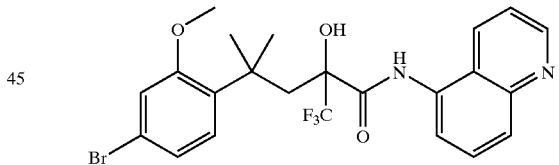

4-(4-Bromo-2-methoxyphenyl)-N-(quinolin-5-yl)-2-hydroxy-4-methyl-2-(trifluoromethyl)pentanamide 4-(4-Bromo-2-methoxyphenyl)-N-(quinolin-5-yl)-4-methyl-2-oxopentanamide According to the instructions for 4-(1,3-benzodioxol-4-yl)-N-(quinolin-5-yl)-4-methyl-2-oxopentanamide (Example 12) after chromatography on silica gel, 363 mg of 4-(4-bromo-2-methoxyphenyl)-N-(quinolin-5-yl)-4-methyl-2-oxopentanamide is obtained from 630 mg of 4-(4-bromo-2-methoxyphenyl)-4-methyl-2-oxopentanoic acid (WO 98/54159). Flash point: 114–115° C.

4-(4-Bromo-2-methoxyphenyl)-N-(quinolin-5-yl)-2-hydroxy-4-methyl-2-(trifluoromethyl)pentanamide According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 280 mg of 4-(4-bromo-2- methoxyphenyl)-N-(quinolin-5-yl)-2-hydroxy-4-methyl-2-(trifluoromethyl)pentanamide is obtained from 528 mg of 4-(4-bromo-2-methoxyphenyl)-N-(quinolin-5-yl)-4-methyl-2-oxopentanamide. Flash point: 208–209° C.

Example 19

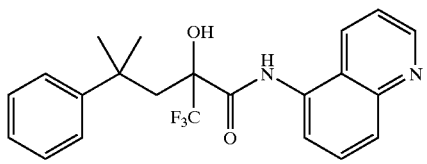

N-(Quinolin-5-yl)-)-2-hydroxy-4-methyl-4-phenyl-2-(trifluoromethyl)pentanamide

N-(Quinolin-5-yl)-)-4-methyl-2-oxo-4-phenylpentanamide

According to the instructions for 4-(1,3-benzodioxol-4-yl)-N-(quinolin-5-yl)-4-methyl-2-oxopentanamide (Example 12) after chromatography on silica gel, 370 mg of N-(quinolin-5-yl)-)-4-methyl-2-oxo-4-phenylpentanamide is obtained from 515 mg of 4-methyl-2-oxo-4-phenylpentanoic acid (WO98/54159). Flash point: 98–99° C.

N-(Quinolin-5-yl)-)-2-hydroxy-4-methyl-4-phenyl-2-(trifluoromethyl)pentanamide

According to the instructions for 4-(1,3-benzodioxol-4-yl)-N-(quinolin-5-yl)-2-hydroxy-4-methyl-2-(trifluoromethyl)pentanamide (Example 12) after chromatography on silica gel, 85 mg of N-(quinolin-5-yl)-2-hydroxy-4-methyl-4-phenyl-2-(trifluoromethyl)pentanamide is obtained from 200 mg of N-(quinolin-5-yl)-4-methyl-2-oxo-4-phenylpentanamide. Flash point: 181–182° C.

Example 20

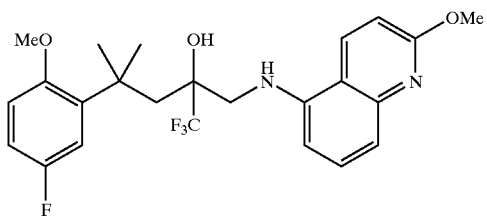

4-(5-Fluoro-2-methoxyphenyl)-1-(2-methoxyquinolin-5-ylamino)-4-methyl-2-(trifluoromethyl)pentan-2-ol 5-Nitroquinoline-1-oxide A solution of 25.5 g (146 mmol) of 5-nitroquinoline in 544 ml of acetic acid and 272 ml of 30% aqueous $H_2O_2$ solution are heated for 100 minutes to 62–69° C. The reaction mixture is poured onto saturated NaCl solution and extracted with ethyl acetate. The combined extracts are concentrated by evaporation to about 50 ml with the addition of toluene. Column chromatography on silica gel with ethyl acetate-MeOH yields 12.3 g of the product as a yellow solid.

H-NMR (CDCl$_3$): δ=7.5 (dd, 1H), 7.85 (t, 1H), 8.45 (d, 1H), 8.5 (d, 1H), 8.6 (d, 1H), 9.15 (d, 1H).

2-Methoxy-5-nitroquinoline

A suspension of 1 g (5 mmol) of 5-nitroquinoline-1-oxide, 1.23 g (6.4 mmol) of toluenesulfonic acid chloride and 1.4 ml (9.9 mmol) of triethylamine in 30 ml of MeOH is stirred for 20 hours at room temperature. The solid is suctioned off and washed with MeOH: 565 mg of light yellow product.

H-NMR (CDCl$_3$): δ=4.1 (s, 3H), 7.15 (d, 1H), 7.7 (t, 1H), 8.15 (d, 2H), 8.8 (d, 1H).

5-Amino-2-methoxyquinoline 550 mg (2.7 mmol) of 2-methoxy-5-nitroquinoline is stirred in 15 ml of ethyl acetate in the presence of 138 mg of 10% Pd—C for 5 hours in a hydrogen atmosphere. The batch is filtered, and the filtrate is concentrated by evaporation: 520 mg of a light yellow oil.

H-NMR (CDCl$_3$): δ=4.05 (s, 3H), 6.65 (d, 1H), 6.85 (d, 1H), 7.3 (d, 1H), 7.4 (t, 1H), 8.0 (d, 1H).

4-(5-Fluoro-2-methoxyphenyl)-2-hydroxy-4-methyl-2-(trifluoromethyl)pentanal 1.5 g (4.8 mmol) of 4-(5-fluoro-2-methoxyphenyl)-4-methyl-2-trifluoromethylpentane-1,2-diol and 3.4 ml (24.4 mmol) of triethylamine in 17 ml of DMSO and 53 ml of CH$_2$Cl$_2$ are mixed at 10° C. in portions with 3 g (18.9 mmol) of pyridine-sulfur trioxide complex. After 3 hours at 12–18° C., it is hydrolyzed while being cooled with ice with saturated NH$_4$Cl solution, and it is extracted with ethyl acetate. The combined extracts are dried (Na$_2$SO$_4$) and concentrated by evaporation: 1.57 g of the product as a light yellow oil.

H-NMR (CDCl$_3$): δ=1.4 (s, 3H), 1.5 (s, 3H), 2.25 (d, 1H), 3.4 (d, 1H), 3.6 (br., 1H), 3.85 (s, 3H), 6.8 (dd, 1H), 6.85–7.0 (m, 2H), 9.05 (s, 1H).

4-(5-Fluoro-2-methoxyphenyl)-1-(2-methoxyquinolin-5-ylamino)-4-methyl-2-(trifluoromethyl)pentan-2-ol 300 mg (0.97 mmol) of 4-(5-fluoro-2-methoxyphenyl)-2-hydroxy-4-methyl-2-(trifluoromethyl)pentanal and 202 mg (1.16 mmol) of 5-amino-2-methoxyquinoline in 10 ml of acetic acid are refluxed for 5 hours. It is allowed to cool to room temperature, 640 mg (3 mmol) of sodium triacetoxy borohydride is added thereto, and it is stirred for 15 hours at room temperature. After toluene is added, the batch is concentrated by evaporation, the residue is taken up in ethyl acetate, washed with saturated NaHCO$_3$ solution, dried and concentrated by evaporation. Column chromatography on silica gel with hexane-ethyl acetate yields 146 mg of the product as a colorless oil.

H-NMR (CDCl$_3$): δ=1.45 (s, 3H), 1.55 (s, 3H), 2.3 (d, 1H), 2.8 (d, 1H), 3.1 (d, 1H), 3.2 (s, 1H), 3.3 (d, 1H), 3.85 (s, 3H), 4.05 (s, 3H), 5.95 (m, 1H), 6.8 (m, 2H), 6.9 (td, 1H), 7.1 (dd, 1H), 7.35 (m, 2H), 7.85 (d, 1H).

MS (ES): m/e=467.

Example 21

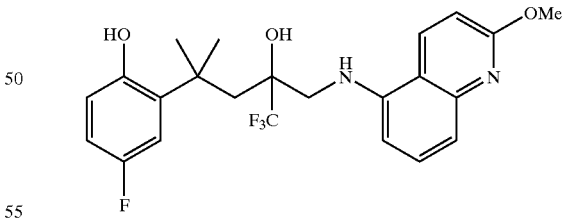

4-(5-Fluoro-2-hydroxyphenyl)-1-(2-methoxyquinolin-5-ylamino)-4-methyl-2-(trifluoromethyl)pentan-2-ol 100 mg (0.21 mmol) of 4-(5-fluoro-2-methoxyphenyl)-1-(2-methoxyquinolin-5-ylamino)-4-methyl-2-(trifluoromethyl)pentan-2-ol in 9 ml of CH$_2$Cl$_2$ is mixed at room temperature with 4 ml of 1M boron tribromide-CH$_2$Cl$_2$ solution. After 15 hours at room temperature, the batch is poured into saturated NaHCO$_3$ solution, stirred for 10 minutes and extracted with ethyl acetate. The combined organic extracts are dried (Na₂SO₄) and concentrated by evaporation in a vacuum. Chromatography on silica gel with hexane/ethyl acetate yields 73 mg of the product.

H-NMR (CDCl₃): δ=1.5 (s, 3H), 1.6 (s, 3H), 2.35 (d, 1H), 2.8 (d, 1H), 3.2 (d, 1H), 3.3 (br., 1H), 3.4 (d, 1H), 4.05 (s, 3H), 6.0 (m, 1H), 6.7 (dd, 1H), 6.8 (td, 1H), 6.85 (d, 1H), 7.1 (dd, 1H), 7.35 (m, 2H), 7.95 (d, 1H).

MS (ES): m/e=453.

Example 22

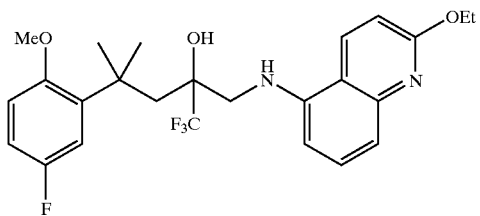

1-(2-Ethoxyquinolin-5-ylamino)-4-(5-fluoro-2-methoxyphenyl)-4-methyl-2-(trifluoromethyl)pentan-2-ol 2-Ethoxy-5-nitroquinoline A suspension of 1 g (5 mmol) of 5-nitroquinoline-1-oxide, 1.23 g (6.4 mmol) of toluenesulfonic acid chloride and 1.4 ml (9.9 mmol) of triethylamine in 30 ml of EtOH is stirred for 60 hours at room temperature. The solid is suctioned off and washed with EtOH: 870 mg of product.

H-NMR (CDCl₃): δ=1.45 (t, 3H), 4.55 (q, 2H), 7.1 (d, 1H), 7.65 (t, 1H), 8.1 (d, 2H), 8.8 (d, 1H).

5-Amino-2-ethoxyquinoline 860 mg (3.9 mmol) of 2-ethoxy-5-nitroquinoline is stirred in 25 ml of ethyl acetate in the presence of 235 mg of 10% Pd—C for 4.5 hours in a hydrogen atmosphere. The batch is filtered, and the filtrate is concentrated by evaporation: 720 mg of a light yellow oil.

H-NMR (CDCl₃): δ=1.45 (t, 3H), 4.5 (q, 2H), 6.65 (d, 1H), 6.85 (d, 1H), 7.3 (d, 1H), 7.4 (t, 1H), 8.0 (d, 1H).

1-(2-Ethoxyquinolin-5-ylamino)-4-(5-fluoro-2-methoxyphenyl)-4-methyl-2-(trifluoromethyl)pentan-2-ol Analogously to Example 20, 500 mg (1.6 mmol) of 4-(5-fluoro-2-methoxyphenyl)-2-hydroxy-4-methyl-2-(trifluoromethyl)pentanal and 363 mg (1.9 mmol) of 5-amino-2-ethoxyquinoline are reacted to form 338 mg of the product.

H-NMR (CDCl₃): δ=1.4 (t, 3H), 1.45 (s, 3H), 1.65 (s, 3H), 2.3 (d, 1H), 2.8 (d, 1H), 3.1 (d, 1H), 3.2 (s, 1H), 3.3 (d, 1H), 3.85 (s, 3H), 4.55 (q, 2H), 5.95 (m, 1H), 6.8 (m, 2H), 6.95 (td, 1H), 7.1 (dd, 1H), 7.35 (m, 2H), 7.85 (d, 1H).

MS (ES): m/e=481.

Example 23

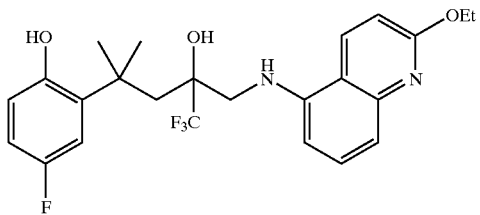

1-(2-Ethoxyquinolin-5-ylamino)-4-(5-fluoro-2-hydroxyphenyl)-4-methyl-2-(trifluoromethyl)pentan-2-ol Analogously to Example 21, 200 mg (0.42 mmol) of 1-(2-ethoxyquinolin-5-ylamino)-4-(5-fluoro-2-methoxyphenyl)-4-methyl-2-(trifluoromethyl)pentan-2-ol is converted into 172 mg of product.

H-NMR (CDCl₃): δ=1.45 (t, 3H), 1.5 (s, 3H), 1.6 (s, 3H), 2.35 (d, 1H), 2.8 (d, 1H), 3.2 (d, 1H), 3.3 (br., 1H), 3.4 (d, 1H), 4.5 (q, 2H), 6.0 (m, 1H), 6.7 (dd, 1H), 6.8 (m, 3H), 7.1 (dd, 1H), 7.35 (m, 2H), 7.95 (d, 1H).

MS (ES): m/e=467.

Example 24

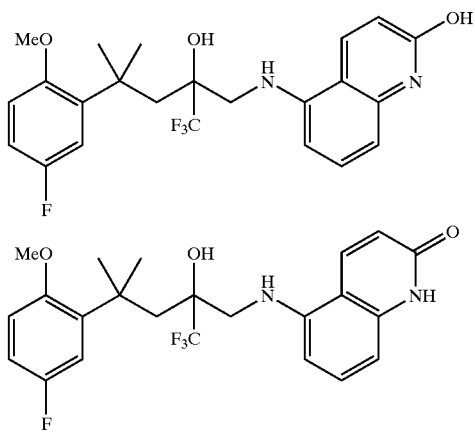

4-(5-Fluoro-2-methoxyphenyl)-1-(2-hydroxyquinolin-5-ylamino)-4-methyl-2-(trifluoromethyl)pentan-2-ol/4-(5-Fluoro-2-methoxyphenyl)-1-(2-quinolon-5-ylamino)-4-methyl-2-(trifluoromethyl)pentan-2-ol 5-Amino-2-quinolone 1.45 g (8.3 mmol) of 5-amino-2-methoxyquinoline is refluxed in 29 ml of 6N HCl for 4.5 hours. It is allowed to cool to room temperature, diluted with water, made basic with NaHCO₃, extracted with ethyl acetate, the combined organic extracts are dried (Na₂SO₄) and concentrated by evaporation. Purification of the residue by chromatography on silica gel with hexane-ethyl acetate yields 670 mg of a yellow solid.

H-NMR ([D]₆-DMSO): δ=5.85 (s, 2H), 6.25 (d, 1H), 6.35 (d, 1H), 6.45 (d, 1H), 7.1 (t, 1H), 8.1 (d, 1H), 11.4 (br.s, 1H).

4-(5-Fluoro-2-methoxyphenyl)-1-(2-hydroxyquinolin-5-ylamino)-4-methyl-2-(trifluoromethyl)pentan-2-ol/4-(5-Fluoro-2-methoxyphenyl)-]-(2-quinolon-5-ylamino)-4-methyl-2-(trifluoromethyl)pentan-2-ol Analogously to Example 20, 226 mg (0.73 mmol) of 4-(5-fluoro-2-methoxyphenyl)-2-hydroxy-4-methyl-2-(trifluoromethyl)pentanal and 140 mg (0.87 mmol) of 5-amino-2-quinolone are reacted to form 200 mg of the product.

H-NMR ([D]₆-DMSO): δ=1.35 (s, 3H), 1.55 (s, 3H), 2.05 (d, 1H), 2.8–3.05 (m, 3H), 3.8 (s, 3H), 5.3 (m, 1H), 5.7 (d, 1H), 5.9 (s, 1H), 6.35 (d, 1H), 6.55 (d, 1H), 6.9–7.15 (m, 3H), 7.85 (d, 1H), 11.5 (br.s, 1H).

MS (ES): m/e=453.

Example 25

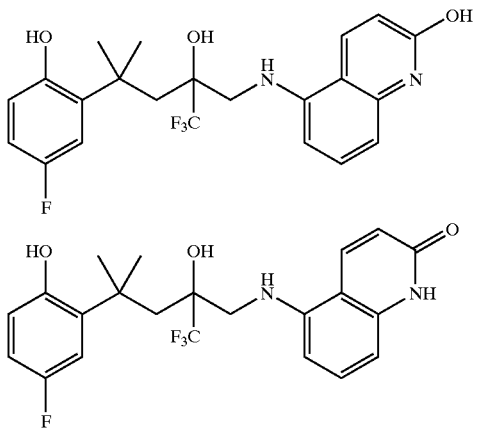

4-(5-Fluoro-2-hydroxyphenyl)-1-(2-hydroxyquinolin-5-ylamino)-4-methyl-2-(trifluoromethyl)pentan-2-ol/4-(5-Fluoro-2-hydroxyphenyl)-1-(2-quinolon-5-ylamino)-4-methyl-2-(trifluoromethyl)pentan-2-ol Analogously to Example 21, 140 mg (0.31 mmol) of 4-(5-fluoro-2-methoxyphenyl)-1-(2-hydroxyquinolin-5-ylamino)-4-methyl-2-(trifluoromethyl)pentan-2-ol is converted into 32 mg of product.

H-NMR ([D]$_6$-DMSO): δ=1.4 (s, 3H), 1.55 (s, 3H), 1.9 (d, 1H), 2.8–3.1 (m, 3H), 5.25 (m, 1H), 5.65 (d, 1H), 5.9 (s, 1H), 6.35 (d, 1H), 6.55 (d, 1H), 6.75 (dd, 1H), 6.85 (td, 1H), 7.0 (d, 1H), 7.1 (t, 1H), 7.85 (d, 1H), 9.75 (br. s, 1H), 11.5 (br.s, 1H).

MS (ES): m/e=439.

Example 26

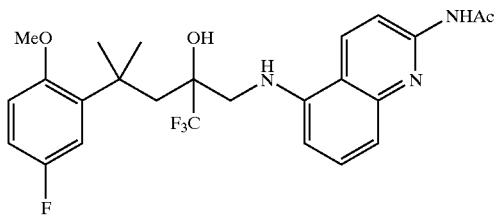

1-(2-Acetylaminoquinolin-5-ylamino)-4-(5-fluoro-2-methoxyphenyl)-4-methyl-2-(trifluoromethyl)pentan-2-ol 2-Chloro-5-nitroquinoline 69 ml of 96% sulfuric acid is carefully added in drops to 84 ml of 100% nitric acid. While being cooled with ice, 25 g (152 mmol) of 2-chloroquinoline is added thereto, and the batch is heated for 1 hour to 60° C. After cooling to room temperature, the batch is carefully incorporated into an ice/water mixture. After 15 minutes of stirring, the solid is washed with water and dried in a vacuum at 40° C. Column chromatography on silica gel with hexane-ethyl acetate yields 10.7 g of a white solid.

H-NMR (CDCl$_3$): δ=7.65 (d, 1H), 7.85 (t, 1H), 8.35 (d, 1H), 8.4 (d, 1H), 9.0 (d, 1H).

2-Amino-5-nitroquinoline 450 mg (2.2 mmol) of 2-chloro-5-nitroquinoline, 10 ml of 25% ammonia water and 10 ml of THF are stirred in a pressure vessel for 8 hours at 120° C. The batch is diluted with NaCl solution and extracted with ethyl acetate. The combined organic phases are dried (Na$_2$SO$_4$) and concentrated by evaporation: 370 mg of product.

H-NMR ([D]$_6$-DMSO): δ=6.9 (br. s, 2H), 7.0 (d, 1H), 7.65 (t, 1H), 7.8 (d, 1H), 7.9 (d, 1H), 8.35 (d, 1H).

2-Acetylamino-5-nitroquinoline 360 mg (1.9 mmol) of 2-amino-5-nitroquinoline is stirred with 4 ml (50 mmol) of pyridine and 2 ml (21 mmol) of acetic anhydride for 15 hours at room temperature. The batch is poured into saturated NaHCO$_3$ solution, stirred for 30 minutes, diluted with saturated NaCl solution and extracted with ethyl acetate. The extracts are dried (Na$_2$SO$_4$) and concentrated by evaporation: 410 mg of a yellow solid.

H-NMR (CDCl$_3$): δ=2.3 (s, 3H), 7.75 (t, 1H), 8.1 (d, 1H), 8.2 (br. 1H), 8.25 (d, 1H), 8.65 (d, 1H), 9.0 (d, 1H).

2-Acetylamino-5-aminoquinoline 400 mg (1.7 mmol) of 2-acetylamino-5-nitroquinoline and 105 mg of 10% Pd—C are stirred in 20 ml of ethyl acetate-MeOH (3:1) for 4 hours in a hydrogen atmosphere at room temperature. The batch is filtered, concentrated by evaporation and purified by column chromatography on silica gel with hexane-ethyl acetate: 210 mg of product.

H-NMR ([D]$_6$-DMSO): δ=2.15 (s, 3H), 5.9 (s, 2H), 6.6 (d, 1H), 6.95 (d, 1H), 7.35 (t, 1H), 8.1 (d, 1H), 8.5 (d, 1H).

1-(2-Acetylaminoquinolin-5-ylamino)-4-(5-fluoro-2-methoxyphenyl)-4-methyl-2-(trifluoromethyl)pentan-2-ol Analogously to Example 20, 263 mg (0.86 mmol) of 4-(5-fluoro-2-methoxyphenyl)-2-hydroxy-4-methyl-2-(trifluoromethyl)pentanal and 205 mg (1.0 mmol) of 2-acetylamino-5-aminoquinoline are reacted to form 197 mg of product.

H-NMR (CDCl$_3$): δ=1.45 (s, 3H), 1.55 (s, 3H), 2.25 (s, 3H), 2.3 (d, 1H), 2.8 (d, 1H), 3.15 (dd, 1H), 3.2 (br., 1H), 3.3 (dd, 1H), 3.85 (s, 3H), 4.3 (br., 3H), 5.95 (d, 1H), 6.8 (dd, 2H), 6.9 (td, 1H), 7.1 (dd, 1H), 7.2 (d, 1H), 7.4 (t, 1H), 8.0 (d, 1H), 8.3 (m, 2H).

MS (ES): m/e=494.

Example 27

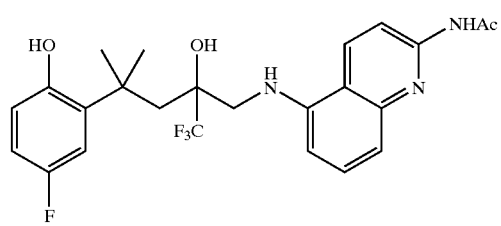

1-(2-Acetylaminoquinolin-5-ylamino)-4-(5-fluoro-2-hydroxyphenyl)-4-methyl-2-(trifluoromethyl)pentan-2-ol Analogously to Example 21, 100 mg (0.20 mmol) of 1-(2-acetylaminoquinolin-5-ylamino)-4-(5-fluoro-2-methoxyphenyl)-4-methyl-2-(trifluoromethyl)pentan-2-ol is converted into 79 mg of product.

H-NMR (CDCl$_3$): δ=1.5 (s, 3H), 1.6 (s, 3H), 2.2 (s, 3H), 2.35 (d, 1H), 2.85 (d, 1H), 3.2 (dd, 1H), 3.35 (dd, 1H), 4.4 (br., 3H), 6.05 (d, 1H), 6.6 (dd, 2H), 6.75 (td, 1H). 7.1 (dd, 1H), 7.15 (d, 1H), 7.4 (t, 1H), 7.95 (d, 1H), 8.2 (d, 1H), 8.35 (br. 1H).

MS (ES): m/e=480.

Example 28

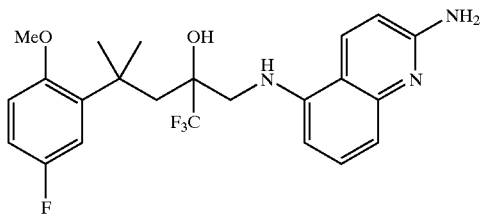

1-(2-Aminoquinolin-5-ylamino)-4-(5-fluoro-2-methoxyphenyl)-4-methyl-2-(trifluoromethyl)pentan-2-ol A solution of 535 mg (1.05 mmol) of 1-(2-acetylaminoquinolin-5-ylamino)-4-(5-fluoro-2-methoxyphenyl)-4-methyl-2-(trifluoromethyl)pentan-2-ol in 18 ml of EtOH-THF (2:1) is refluxed with 12 ml of 3N sodium hydroxide solution for 90 minutes. The batch is diluted with saturated NaCl and extracted with ethyl acetate. The extracts are dried ($Na_2SO_4$) and concentrated by evaporation in a vacuum. Column chromatography on silica gel with ethyl acetate yields 380 mg of the product as a yellow oil.

H-NMR ($[D]_6$-DMSO): δ=1.35 (s, 3H), 1.55 (s, 3H), 2.05 (d, 1H), 2.7–3.0 (m, 3H), 3.8 (s, 3H), 5.05 (m, 1H), 5.55 (d, 1H), 6.05 (br., 1H), 6.25 (s, 2H), 6.6 (d, 1H), 6.75 (d, 1H), 6.9–7.2 (m, 3H), 7.85 (d, 1H).

MS (ES): m/e=452.

Example 29

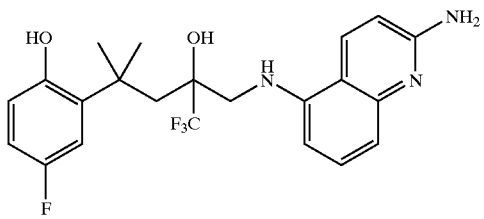

1-(2-Aminoquinolin-5-ylamino)-4-(5-fluoro-2-hydroxyphenyl)-4-methyl-2-(trifluoromethyl)pentan-2-ol Analogously to Example 28, 48 mg (0.1 mmol) of 1-(2-acetylaminoquinolin-5-ylamino)-4-(5-fluoro-2-hydroxyphenyl)-4-methyl-2-(trifluoromethyl)pentan-2-ol is converted into 21 mg of product.

H-NMR ($[D]_6$-DMSO): δ=1.4 (s, 3H), 1.55 (s, 3H), 1.95 (d, 1H), 2.85 (dd, 1H), 3.05 (d, 1H), 5.05 (m, 1H), 5.6 (d, 1H), 6.25 (s, 2H), 6.6 (d, 1H), 6.7 (m, 2H), 6.8 (m, 1H), 6.95 (dm, 1H), 7.1 (t, 1H), 7.85 (d, 1H).

MS (ES): m/e=438.

Example 30

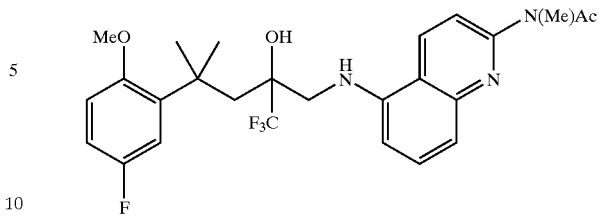

1-(2-(Acetyl(methyl)amino)quinolin-5-ylamino)-4-(5-fluoro-2-methoxyphenyl)-4-methyl-2-(trifluoromethyl)pentan-2-ol 2-Methylamino-5-nitroquinoline 1.0 g (4.8 mmol) of 2-chloro-5-nitroquinoline and 20 ml of 2 M methanolic methylamine solution are heated in a pressure vessel for 8 hours to 120° C. The batch is concentrated by evaporation after the addition of toluene. The residue is purified by column chromatography on silica gel with hexane-ethyl acetate: 580 mg of product.

H-NMR ($CDCl_3$): δ=3.1 (d, 3H), 4.95 (br., 1H), 6.8 (d, 1H), 7.55 (t, 1H), 7.95 (2d, 2H), 8.6 (d, 1H).

2-Acetyl(methyl)amino-5-nitroquinoline 580 mg (2.4 mmol) of 2-methylamino-5-nitroquinoline is stirred with 4 ml (50 mmol) of pyridine and 2 ml (21 mmol) of acetic anhydride for 15 hours at room temperature and stirred for 4.5 hours at 60° C. The batch is diluted with ethyl acetate, poured into saturated $NaHCO_3$ solution, stirred for 30 minutes, and extracted with ethyl acetate. The extracts are dried ($Na_2SO_4$) and concentrated by evaporation. The residue is purified on silica gel with hexane-ethyl acetate: 660 mg of a yellow solid.

H-NMR ($CDCl_3$): δ=2.35 (s, 3H), 3.6 (s, 3H), 7.75 (t, 1H), 7.9 (d, 1H), 8.25 (d, 1H), 8.3 (d, 1H), 9.0 (d, 1H).

2-Acetyl(methyl)amino-5-aminoquinoline 650 mg (2.7 mmol) of 2-acetyl(methyl)amino-5-nitroquinoline and 161 mg of 10% Pd—C are stirred in 25 ml of ethyl acetate for 2 hours in a hydrogen atmosphere at room temperature. The batch is filtered and concentrated by evaporation: 490 mg of product.

H-NMR ($CDCl_3$): δ=2.2 (s, 3H), 3.5 (s, 3H), 4.2 (br., 2H), 6.8 (d, 1H), 7.4 (d, 1H), 7.45 (d, 1H), 7.5 (t, 1H), 8.2 (d, 1H).

1-(2-(Acetyl(methyl)amino)quinolin-5-ylamino)-4-(5-fluoro-2-methoxyphenyl)-4-methyl-2-(trifluoromethyl)pentan-2-ol Analogously to Example 20, 576 mg (1.9 mmol) of 4-(5-fluoro-2-methoxyphenyl)-2-hydroxy-4-methyl-2-(trifluoromethyl)pentanal and 480 mg (2.2 mmol) of 2-acetyl(methyl)amino-5-aminoquinoline are reacted to form 330 mg of product.

H-NMR ($CDCl_3$): δ=1.45 (s, 3H), 1.55 (s, 3H), 2.2 (s, 3H), 2.4 (d, 1H), 2.75 (d, 1H), 3.15 (dd, 1H), 3.2 (s, 1H), 3.35 (dd, 1H), 3.5 (s, 3H), 3.85 (s, 3H), 4.3 (m, 1H), 6.1 (d, 1H), 6.8 (dd, 1H), 6.95 (td, 1H), 7.1 (dd, 1H), 7.3–7.5 (m, 3H), 8.0 (d, 1H).

MS (ES): m/e=508.

Example 31

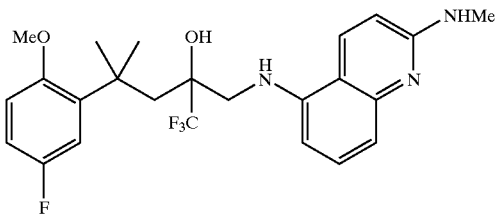

4-(5-Fluoro-2-methoxyphenyl)-4-methyl-1-(2-(methylamino)quinolin-5-ylamino)-2-(trifluoromethyl)pentan-2-ol Analogously to Example 28, 83 mg (0.16 mmol) of 1-(2-(acetyl(methyl)amino)quinolin-5-ylamino)-4-(5-fluoro-2-methoxyphenyl)-4-methyl-2-(trifluoromethyl) pentan-2-ol is converted into 48 mg of product.

H-NMR (CDCl$_3$): δ=1.4 (t, 3H), 1.5 (s, 3H), 2.2 (d, 1H), 2.75 (d, 1H), 2.95 (d, 3H), 3.0 (m, 1H), 3.2 (m, 1H), 3.8 (s, 3H), 4.0 (m, 1H), 5.05 (br., 1H), 5.75 (d, 1H), 6.5 (d, 2H), 6.75 (dd, 1H), 6.9 (td, 1H), 7.05 (dd, 1H), 7.1 (m, 1H), 7.2 (m, 1H), 7.65 (d, 1H).

MS (ES): m/e=466.

Example 32

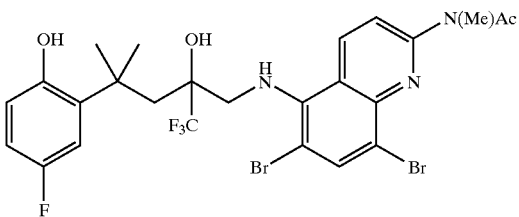

1-(2-(Acetyl(methyl-amino)-6,8-dibromoquinolin-5-ylamino)-4-(5-fluoro-2-hydroxyphenyl)-4-methyl-2-(trifluoromethyl)pentan-2-ol 200 mg (0.39 mmol) of 1-(2-(acetyl(methyl)amino) quinolin-5-ylamino)-4-(5-fluoro-2-methoxyphenyl)-4-methyl-2-(trifluoromethyl)pentan-2-ol in 17 ml of CH$_2$Cl$_2$ is mixed at 0° C. with 7.6 ml of 1M boron tribromide-CH$_2$Cl$_2$ solution. After 15 hours at room temperature, 7.6 ml of 1M boron tribromide-CH$_2$Cl$_2$ solution is added once more and stirred for 20 hours at room temperature. The batch is poured into saturated NaHCO$_3$ solution, diluted with NaCl solution and ethyl acetate, stirred for 15 minutes and extracted with ethyl acetate. The combined organic extracts are dried (Na$_2$SO$_4$) and concentrated by evaporation. Chromatography with hexane-ethyl acetate on silica gel yields 98 mg of the product.

H-NMR (CDCl$_3$): δ=1.4 (t, 3H), 1.55 (s, 3H), 2.3 (d, 1H), 2.45 (s, 3H), 2.6 (d, 1H), 2.95 (t, 1H), 3.25 (dd, 1H), 3.65 (s, 3H), 3.95 (s, 1H), 4.1 (m, 1H), 5.7 (br. s, 1H), 6.45 (dd, 1H), 6.6 (td, 1H), 6.9 (dd, 1H), 7.6 (d, 1H), 7.95 (d, 1H), 8.05 (s, 1H).

MS (ES): m/e=650, 652, 654 (1:2:1).

Example 33

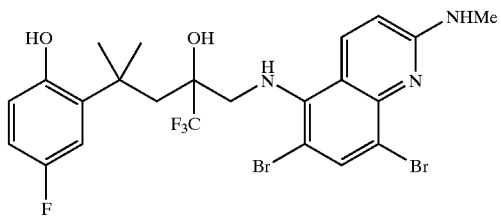

1-(6,8-Dibromo-2-(methylamino)quinolin-5-ylamino)-4-(5-fluoro-2-hydroxyphenyl)-4-methyl-2-(trifluoromethyl)pentan-2-ol Analogously to Example 28, 100 mg (0.15 mmol) of 1-(2-(acetyl(methyl)amino)-6,8-dibromoquinolin-5-ylamino)-4-(5-fluoro-2-hydroxyphenyl)-4-methyl-2-(trifluoromethyl)pentan-2-ol is converted into 97 mg of product.

H-NMR ([D]$_6$-DMSO): δ=1.3 (s, 3H), 1.5 (s, 3H), 1.95 (d, 1H), 2.95 (d, 3H), 3.0 (d, 1H), 3.15 (dd, 1H), 4.4 (m, 1H), 6.15 (s, 1H), 6.65 (m, 2H), 6.75 (td, 1H), 6.85 (dd, 1H), 7.35 d, 1H), 7.55 (d, 1H), 7.8 (s, 1H), 9.55 (s, 1H).

Example 34

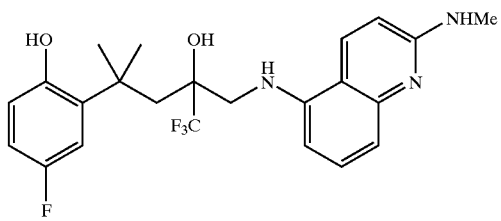

4-(5-Fluoro-2-hydroxyphenyl)-4-methyl-1-(2-(methylamino)quinolin-5-ylamino)-2-(trifluoromethyl)pentan-2-ol 45 mg (0.07 mmol) of 1-(6,8-dibromo-2-(methylamino) quinolin-5-ylamino)-4-(5-fluoro-2-hydroxyphenyl)-4-methyl-2-(trifluoromethyl)pentan-2-ol and 50 mg of 10% Pd—C are stirred in 2 ml for 90 minutes under hydrogen atmosphere. The batch is filtered and concentrated by evaporation. Column chromatography on silica gel with ethyl acetate-MeOH yields 19 mg of the product.

H-NMR ([D]$_6$-DMSO): δ=1.4 (s, 3H), 1.55 (s, 3H), 1.9 (d, 1H), 2.8 (d, 3H und m, 1H), 3.05 (d, 1H), 3.15 (d, 1H), 4.95 (m, 1H), 5.6 (d, 1H), 5.95 (s, 1H), 6.6 (d, 1H), 6.75 (dd, 1H), 6.8 (d, 1H), 6.85 (td, 1H), 7.0 (dd, 1H), 7.05 (t, 1H), 7.8 (d, 1H), 9.7 (s, 1H).

MS (ES): m/e=452.

Example 35

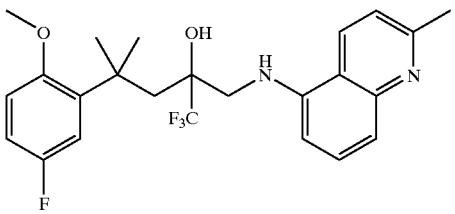

4-(5-Fluoro-2-methoxyphenyl)-4-methyl-1-(2-methylquinolin-5-ylamino)-2-(trifluoromethyl)pentan-2-ol

300 mg (0.97 mmol) of 4-(5-fluoro-2-methoxyphenyl)-2-hydroxy-4-methyl-2-(trifluoromethyl)pentanal and 184 mg (1.16 mmol) of 5-amino-2-methylquinoline are heated in 10 ml of acetic acid over 6 hours to 125° C. After cooling to room temperature, it is mixed with 320 mg (1.51 mmol) of sodium triacetoxy borohydride, and it is allowed to stir for 16 hours. After the addition of another 320 mg (1.51 mmol) of sodium triacetoxy borohydride and 2 hours of stirring, toluene is added, and it is concentrated by evaporation in a vacuum. The residue is taken up in ethyl acetate, the organic phase is washed with saturated sodium bicarbonate and saturated sodium chloride solution, and it is dried on sodium sulfate. After chromatography on silica gel with hexane-ethyl acetate (0–60%), 221 mg of the product is obtained.

$^1$H-NMR (CDCl$_3$); δ=1.46 (s, 3H), 1.57 (s, 3H), 2.33 (d, 1H), 2.72 (s, 3H), 2.78 (d, 1H), 3.12 (dd, 1H), 3.30 (dd, 1H), 3.84 (s, 3H), 4.23 (br., 1H), 6.01 (d, 1H), 6.80 (dd, 1H), 6.94 (ddd, 1H), 7.12 (dd, 1H), 7.21 (d, 1H), 7.41 (t, 1H), 7.46 (d, 1H), 7.88 (d, 1H).

Example 36

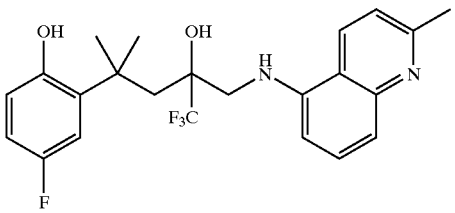

4-(5-Fluoro-2-hydroxyphenyl)-4-methyl-1-(2-methylquinolin-5-ylamino)-2-(trifluoromethyl)-pentan-2-ol

Analogously to Example 35, 153 mg (0.34 mmol) of 4-(5-fluoro-2-methoxyphenyl)-4-methyl-1-(2-methylquinolin-5-ylamino)-2-(trifluoromethyl)-pentan-2-ol in 17 ml of CH$_2$Cl$_2$ is reacted with 6.8 ml of 1M boron tribromide-CH$_2$Cl$_2$ solution. After chromatography on silica gel with hexane-ethyl acetate (0–55%), 99 mg of the product is obtained.

$^1$H-NMR (CDCl$_3$); δ=1.51 (s, 3H), 1.59 (s, 3H), 2.41 (d, 1H), 2.70 (s, 3H), 2.80 (d, 1H), 3.24 (dd, 1H), 3.42 (dd, 1H), 4.32 (br, 1H), 6.06 (d, 1H), 6.63 (dd, 1H), 6.80 (ddd, 1H), 7.09 (dd, 1H), 7.18 (d, 1H), 7.35 (t, 1H), 7.42 (d, 1H), 7.87 (d, 1H).

Example 37

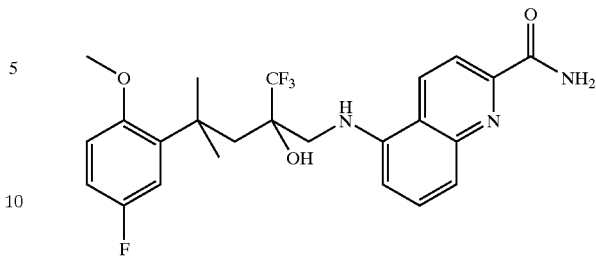

5-[4-(5-Fluoro-2-methoxyphenyl)-2-hydroxy-4-methyl-2-trifluoromethylpentylamino]quinoline-2-carboxylic acid amide

5-Aminoquinoline-2-carboxylic acid amide 840 mg (4.16 mmol) of 5-aminoquinoline-2-carboxylic acid methyl ester is dissolved in 70 ml of a 7N methanolic ammonia solution. It is stirred for 3.5 hours at 40° C., then for 20 hours at room temperature. After the solvent is removed in a vacuum, the purification is carried out on silica gel with hexane-ethyl acetate (0–100%) as well as with ethyl acetate-methanol (0–10%). 690 mg (88% of theory) of the product is obtained.

$^1$H-NMR (DMSO-d$_6$): δ=6.11 (s, 2H), 6.78 (d, 1H), 7.27 (d, 1H), 7.51 (t, 1H), 7.70 (s, 1H), 7.96 (d, 1H), 8.20 (s, 1H), 8.68 (d, 1H).

5-[4-(5-Fluoro-2-methoxyphenyl)-2-hydroxy-4-methyl-2-trifluoromethyl-pentylidenamino]-quinoline-2-carboxylic acid amide A solution that consists of 290 mg (1.55 mmol) of 5-aminoquinoline-2-carboxylic acid amide, 616 mg (2.0 mmol) of 4-(5-fluoro-2-methoxyphenyl)-2-hydroxy-4-methyl-2-trifluoromethyl-pentanal and 3.80 ml of concentrated acetic acid in 30 ml of toluene is refluxed for 20 hours in a water separator. Then, the solvent is removed in a vacuum. After the residue is purified on silica gel with hexane/ethyl acetate (0–70%), 438 mg (59% of theory) of the product is obtained.

$^1$H-NMR (300 MHz, DMSO-d$_6$): δ=1.33 (s, 3H), 1.53 (s, 3H), 2.20 (d, 1H), 3.33 (d, 1H), 3.77 (s, 3H), 6.31 (s, 1H), 6.48–6.55 (m, 1H), 6.70–6.75 (m, 3H), 7.59 (s, 1H), 7.70 (t, 1H), 7.82 (br, 1H), 7.98 (d, 1H), 8.31 (br, 1H), 8.82 (d, 1H).

5-[4-(5-Fluoro-2-methoxyphenyl)-2-hydroxy-4-methyl-2-trifluoromethylpentylamino]quinoline-2-carboxylic acid amide 253 mg (0.53 mmol) of 5-[4-(5-fluoro-2-methoxyphenyl)-2-hydroxy-4-methyl-2-trifluoromethylpentylidenamino]quinoline-2-carboxylic acid amide is dissolved in 10 ml of tetrahydrofuran-methanol (50%) and mixed with 101 mg (2.65 mmol) of sodium borohydride. After 20 hours, the solvent is removed in a vacuum. The subsequent recrystallization of the residue from ethyl acetate-methanol and purification of the mother liquor that is concentrated by evaporation on silica gel with hexane-ethyl acetate (0–50%) yield 116 mg (46% of theory) of the product.

$^1$H-NMR (300 MHz, DMSO-d$_6$): δ=1.38 (s, 3H), 1.56 (s, 3H), 2.05 (d, 1H), 2.91–2.96 (m, 2H), 3.07 (d, 1H), 3.78 (s, 3H), 5.59 (t, 1H), 5.99 (s, 1H), 6.02 (d, 1H), 6.91–7.06 (m, 2H), 7.08 (dd, 1H), 7.32 (d, 1H), 7.46 (t, 1H), 7.72 (br, 1H), 8.03 (d, 1H), 8.21 (br, 1H), 8.49 (d, 1H).

Example 38

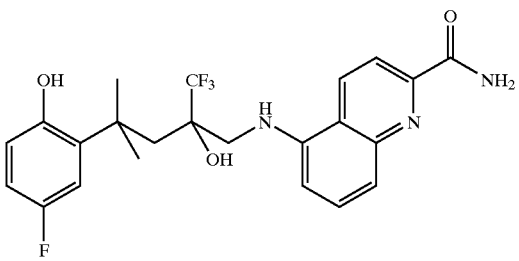

5-[4-(5-Fluoro-2-hydroxyphenyl)-2-hydroxy-4-methyl-2-trifluoromethylpentylamino]quinoline-2-carboxylic acid amide 220 mg (0.46 mmol) of 5-[4-(5-fluoro-2-methoxyphenyl)-2-hydroxy-4-methyl-2-trifluoromethylpentylamino]quinoline-2-carboxylic acid amide is dissolved in 5.0 ml of dichloromethane and mixed with 9.2 ml of a 1N boron tribromide solution in dichloromethane. After 20 hours at room temperature, the reaction is halted by adding methanol. The solvent is removed in a vacuum, the residue is taken up in saturated sodium bicarbonate solution and ethyl acetate, extracted with ethyl acetate, and the combined organic phases are dried on sodium sulfate. After removal of the solvent and purification on silica gel with hexane-ethyl acetate (0–100%), 60 mg (28% of theory) of the product is obtained.

$^1$H-NMR (300 MHz, DMSO-d$_6$): δ=1.40 (s, 3H), 1.57 (s, 3H), 1.93 (d, 1H), 2.98 (dd, 1H), 3.16–3.20 (m, 2H), 5.52 (br, 1H), 5.99 (br, 1H), 6.68 (dd, 1H), 6.78–6.84 (m, 1H), 7.01 (dd, 1H), 7.32 (d, 1H), 7.45 (t, 1H), 7.71 (s, 1H), 8.03 (d, 1H), 8.21 (s, 1H), 8.46 (d, 1H), 9.73 (s, 1H).

Example 39

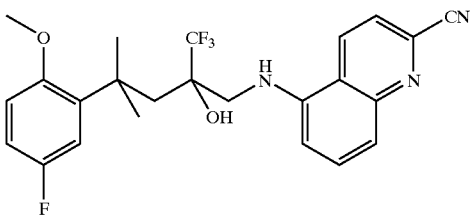

5-[4-(5-Fluoro-2-methoxyphenyl)-2-hydroxy-4-methyl-2-trifluoromethylpentylamino]quinoline-2-carboxylic acid nitrile 5-[4-(5-Fluoro-2-methoxyphenyl)-2-hydroxy-4-methyl-2-trifluoromethylpentylidenamino]-quinoline-2-carboxylic acid nitrile 220 mg (0.46 mmol) of 5-[4-(5-fluoro-2-methoxyphenyl)-2-hydroxy-4-methyl-2-trifluoromethylpentylidenamino]quinoline-2-carboxylic acid amide and 1.80 ml (3.2 mmol) of triethylamine are dissolved in 18 ml of dichloromethane and mixed with 0.44 ml (1.38 mmol) of trifluoroacetic acid anhydride. After 2 minutes, the reaction is halted by adding water. It is extracted three times with ethyl acetate, and the combined organic phases are washed with a 1N sodium hydroxide solution. After drying on sodium sulfate, removal of the solvent in a vacuum as well as chromatography on silica gel with hexane-ethyl acetate (0–100%), 190 mg (90% of theory) of the product is obtained.

$^1$H-NMR (300 MHz, CDCl$_3$): δ=1.37 (s, 3H), 1.57 (s, 3H), 2.30 (d, 1H), 3.47 (d, 1H), 3.80 (s, 3H), 4.69 (s, 1H), 6.38–6.43 (m, 1H), 6.59–6.60 (m, 2H), 6.80 (dd, 1H), 7.54 (s, 1H), 7.65 (t, 1H), 7.74 (d, 1H), 8.03 (d, 1H), 8.44 (d, 1H).

5-[4-(5-Fluoro-2-methoxyphenyl)-2-hydroxy-4-methyl-2-trifluoromethylpentylamino]quinoline-2-carboxylic acid nitrile Analogously to Example 37, 90 mg (0.2 mmol) of 5-[4-(5-fluoro-2-methoxyphenyl)-2-hydroxy-4-methyl-2-trifluoromethylpentylidenamino]-quinoline-2-carboxylic acid nitrile is reacted with 31 mg (0.8 mmol) of sodium in 5.0 ml of methanol and 1.0 ml of tetrahydrofuran. After working-up and chromatography on silica gel with hexane-ethyl acetate (0–100%), 50 mg (54% of theory) of the product is obtained.

$^1$H-NMR (300 MHz, DMSO-d$_6$): δ=1.38 (s, 3H), 1.56 (s, 3H), 2.05 (d, 1H), 2.88–3.11 (m, 3H), 3.78 (s, 3H), 5.82–5.84 (m, 1H), 5.94 (s, 1H), 6.14 (d, 1H), 6.89–7.09 (m, 3H), 7.31 (d, 1H), 7.54 (t, 1H), 7.93 (d, 1H), 8.61 (d, 1H).

Example 40

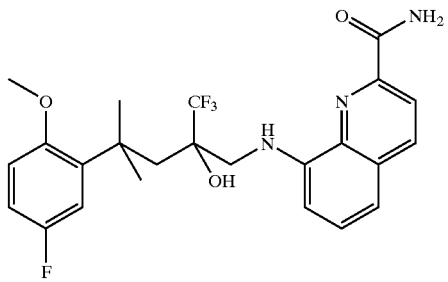

8-[4-(5-Fluoro-2-methoxyphenyl)-2-hydroxy-4-methyl-2-trifluoromethylpentylamino]quinoline-2-carboxylic acid amide 8-Aminoquinoline-2-carboxylic acid amide Analogously to Example 37, 120 mg (0.59 mmol) of 8-aminoquinoline-2-carboxylic acid methyl ester is reacted with 10 ml of a 7N methanolic ammonia solution. After purification on silica gel with hexane-ethyl acetate, 79 mg (72% of theory) of the product is obtained.

$^1$H-NMR (300 MHz, DMSO-d$_6$): δ=6.51 (br, 2H), 6.84 (d, 1H), 7.04 (d, 1H), 7.35 (t, 1H), 7.58 (br, 1H), 8.03 (d, 1H), 8.27 (d, 1H), 8.87 (br, 1H).

8-[4-(5-Fluoro-2-methoxyphenyl)-2-hydroxy-4-methyl-2-trifluoromethylpentylidenamino]-quinoline-2-carboxylic acid amide Analogously to Example 37, 535 mg (2.86 mmol) of a mixture that consists of 5- and 8-aminoquinoline-2-carboxylic acid amide is reacted with 1.06 g (3.43 mmol) of 4-(5-fluoro-2-methoxyphenyl)-2-hydroxy-4-methyl-2-(trifluoromethyl)pentanal in 4.50 ml of concentrated acetic acid and 20 ml of toluene. After 40 hours, the purification on silica gel with hexane-ethyl acetate (0–40%) takes place, and 624 mg (46% of theory) of the desired product is obtained.

$^1$H-NMR (300 MHz, CDCl$_3$): δ=1.37 (s, 3H), 1.60 (s, 3H), 2.27 (d, 1H), 3.46 (d, 1H), 3.70 (s, 3H), 5.08 (s, 1H), 5.60 (br, 1H), 6.34–6.48 (m, 2H), 6.83 (dd, 1H), 7.00 (d, 1H), 7.49–7.59 (m, 2H), 7.65–7.78 (m, 2H), 8.32 (s, 2H).

8-[4-(5-Fluoro-2-methoxyphenyl)-2-hydroxy-4-methyl-2-trifluoromethylpentylamino]quinoline-2-carboxylic acid amide 703 mg (1.47 mmol) of 8-[4-(5-fluoro-2-methoxyphenyl)-2-hydroxy-4-methyl-2-trifluoromethyl-pentylidenamino]quinoline-2-carboxylic acid amide in 10 ml of methanol and 5.0 ml of tetrahydrofuran are mixed with 449 mg (11.8 mmol) of sodium borohydride. After 16 hours, the solvent is concentrated by evaporation, the residue is taken up in water and ethyl acetate, extracted with ethyl acetate, and the combined organic phases are dried on sodium sulfate. After removal of the solvent and purification on silica gel with hexane-ethyl acetate (0–50%) as well as dichloromethane-methanol (0–7%), 358 mg (51% of theory) of the product is obtained.

$^1$H-NMR (300 MHz, DMSO-$d_6$): δ=1.39 (s, 3H), 1.58 (s, 3H), 2.10 (d, 1H), 2.86 (d, 1H), 3.13 (d, 2H), 3.76 (s, 3H), 5.87 (s, 1H), 6.24 (d, 1H), 6.81–6.97 (m, 3H), 7.06–7.11 (m, 2H), 7.32 (t, 1H), 7.76 (br, 1H), 8.06 (d, 1H), 8.31 (d, 1H), 8.45 (br, 1H).

Example 41

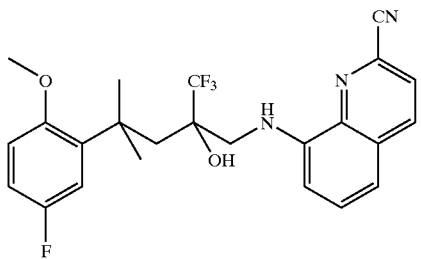

8-[4-(5-Fluoro-2-methoxyphenyl)-2-hydroxy-4-methyl-2-trifluoromethylpentylamino]quinoline-2-carboxylic acid nitrile 185 mg (0.386 mmol) of 8-[4-(5-fluoro-2-methoxyphenyl)-2-hydroxy-4-methyl-2-trifluoromethylpentylamino]quinoline-2-carboxylic acid amide in 5.0 ml of dimethylformamide is mixed with 397 mg (2.80 mmol) of diphosphorus pentoxide. After five days at room temperature, insoluble components are filtered off. The filtrate is diluted with ethyl acetate and saturated sodium chloride solution. It is extracted with ethyl acetate, the combined organic phases are dried on sodium sulfate, and then the solution is concentrated by evaporation. Dimethylformamide radicals are removed under high vacuum. After purification on silica gel with hexane-ethyl acetate (0–30%), 102 mg (57% of theory) of the product is obtained.

$^1$H-NMR (300 MHz, DMSO-$d_6$): δ=1.37 (s, 3H), 1.56 (s, 3H), 1.99 (d, 1H), 2.95 (dd, 1H), 3.03 (d, 1H), 3.13 (dd, 1H), 3.79 (s, 3H), 6.16–6.17 (m, 2H), 6.23 (d, 1H), 6.76–6.79 (m, 2H), 7.01 (dd, 1H), 7.15 (d, 1H), 7.43 (t, 1H), 7.96 (d, 1H), 8.44 (d, 1H).

Example 42

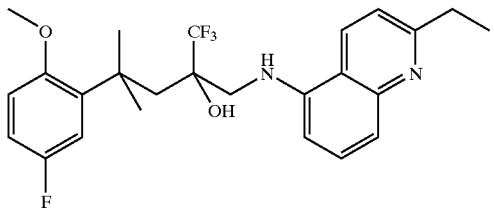

1-(2-Ethylquinolin-5-ylamino)-4-(5-fluoro-2-methoxyphenyl)-4-methyl-2-(trifluoromethyl)pentan-2-ol 2-Chloro-5-nitroquinoline 10.0 g (61.1 mmol) of 2-chloroquinoline is dissolved in 34 ml of concentrated sulfuric acid. At 0° C., 8.4 g (76.4 mmol) of potassium nitrate is added in portions. After 20 hours at room temperature, the reaction mixture is poured onto ice water, and the aqueous phase is extracted with ethyl acetate. The combined organic phases are washed with saturated sodium bicarbonate solution and dried on sodium sulfate. After the solvent is removed in a vacuum and after chromatography on silica gel with hexane-ethyl acetate (10–100%), 5.06 g (40% of theory) of the product is obtained.

$^1$H-NMR (300 MHz, CDCl$_3$): δ=7.62 (d, 1H), 7.84 (t, 1H), 8.33 (d, 1H), 8.39 (d, 1H), 8.98 (d, 1H).

5-Nitro-2-vinylquinoline 5.06 g (24.5 mmol) of 2-chloro-5-nitroquinoline, 1.26 g (4.9 mmol) of triphenylphosphine and 8.0 g (25.2 mmol) of tri-n-butylvinyltin are dissolved in 60 ml of toluene. After adding 2.75 g (2.5 mmol) of tris(dibenzylidenacetone)dipalladium, the reaction mixture is allowed to reflux for 20 hours. Then, it is filtered on Celite and washed with ethyl acetate. The filtrate is mixed with saturated ammonium chloride solution. It is extracted with ethyl acetate, and the combined organic phases are dried on sodium sulfate. After the solvent is removed in a vacuum and after subsequent chromatography on silica gel with hexane-ethyl acetate (5–20%), 3.05 g (62% of theory) of the product is obtained.

$^1$H-NMR (300 MHz, CDCl$_3$): δ=5.78 (d, 1H), 6.40 (d, 1H), 7.03 (dd, 1H), 7.75–7.81 (m, 2H), 8.28–8.38 (m, 2H), 8.95 (d, 1H).

2-Ethylquinolin-5-ylamine 1.0 g (5.0 mmol) of 5-nitro-2-vinylquinoline is dissolved in 30 ml of ethyl acetate. After 100 mg of palladium on carbon and 50 mg of sodium carbonate are added, the reaction mixture is allowed to stir for 20 hours at room temperature under hydrogen atmosphere. It is then filtered on Celite and washed with ethyl acetate. After the solvent is removed in a vacuum and after chromatography on silica gel with hexane-ethyl acetate (0–100%), then with ethyl acetate-methanol (0–30%), 720 mg (84% of theory) of the product is obtained.

$^1$H-NMR (300 MHz, DMSO-$d_6$): δ=1.29 (t, 3H), 2.86 (q, 2H), 5.87 (br, 2H), 6.63 (d, 1H), 7.09 (d, 1H), 7.25 (d, 1H), 7.35 (t, 1H), 8.41 (d, 1H).

1-(2-Ethylquinolin-5-ylimino)-4-(5-fluoro-2-methoxyphenyl)-4-methyl-2-(trifluoromethyl)pentan-2-ol Analogously to Example 37, 334 mg (1.94 mmol) of 2-ethylquinolin-5-ylamine is reacted with 500 mg (1.62 mmol) of 4-(5-fluoro-2-methoxyphenyl)-2-hydroxy-4-methyl-2-trifluoromethylpentanal in 2.20 ml of concentrated acetic acid and 15 ml of toluene. After purification on silica gel with hexane-ethyl acetate (0–100%), 600 mg (80% of theory) of the corresponding imine is obtained.

$^1$H-NMR (300 MHz, CDCl$_3$): δ=1.38 (s, 3H), 1.41 (t, 3H), 1.57 (s, 3H), 2.30 (d, 1H), 3.03 (q, 2H), 3.42 (d, 1H), 3.80 (s, 3H), 4.88 (s, 1H), 6.40–6.56 (m, 3H), 6.81 (dd, 1H), 7.37 (d, 1H), 7.47–7.55 (m, 2H), 7.92 (d, 1H), 8.20 (d, 1H).

1-(2-Ethylquinolin-5-ylamino)-4-(5-fluoro-2-methoxyphenyl)-4-methyl-2-(trifluoromethyl)pentan-2-ol 600 mg (1.3 mmol) of 1-(2-ethylquinolin-5-ylimino)-4-(5-fluoro-2-methoxyphenyl)-4-methyl-2-(trifluoromethyl)pentan-2-ol in 5.0 ml of methanol is mixed at 0° C. with 197 mg (5.2 mmol) of sodium borohydride. After 2 hours at room temperature, water is added, and methanol is removed in a vacuum. The aqueous phase is extracted with dichloromethane, the combined organic phases are dried on sodium sulfate, and the solvent is removed in a vacuum. After purification on silica gel with hexane-ethyl acetate (0–100%), 400 mg (66% of theory) of the product is obtained.

¹H-NMR (300 MHz, CDCl₃): δ=1.37 (t, 3H), 1.46 (s, 3H), 1.57 (s, 3H), 2.33 (d, 1H), 2.78 (d, 1H), 2.98 (q, 2H), 3.13 (dd, 1H), 3.19 (br, 1H), 3.30 (dd, 1H), 3.84 (s, 3H), 4.24 (br, 1H), 6.01 (d, 1H), 6.80 (dd, 1H), 6.91–6.98 (m, 1H), 7.12 (dd, 1H), 7.23 (d, 1H), 7.38–7.49 (m, 2H), 7.91 (d, 1H).

Example 43

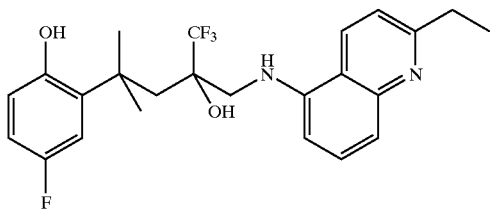

1-(2-Ethylquinolin-5-ylamino)-4-(5-fluoro-2-hydroxyphenyl)-4-methyl-2-(trifluoromethyl)pentan-2-ol 230 mg (0.49 mmol) of 1-(2-ethylquinolin-5-ylimino)-4-(5-fluoro-2-methoxyphenyl)-4-methyl-2-(trifluoromethyl)pentan-2-ol in 4.5 ml of dichloromethane is mixed at 0° C. with 7.30 ml (7.30 mmol) of a 1 M boron tribromide solution. After 23 hours at room temperature, the reaction is brought to a halt by the addition of 30 ml of methanol. The reaction mixture is allowed to stir for one hour at room temperature, and then the solvent is removed in a vacuum. After chromatography on silica gel with ethyl acetate-methanol (0–10%), 60 mg (27% of theory) of the product is obtained.

¹H-NMR (300 MHz, DMSO-d₆): δ=1.29 (t, 3H), 1.40 (s, 3H), 1.56 (s, 3H), 1.93 (d, 1H), 2.87 (q, 2H), 2.95 (d, 1H), 3.08–3.20 (m, 2H), 5.34 (br, 1H), 5.89 (d, 1H), 5.96 (s, 1H), 6.73 (dd, 1H), 6.83–6.88 (m, 1H), 7.01 (dd, 1H), 7.14 (d, 1H), 7.27–7.34 (m, 2H), 8.18 (d, 1H), 9.73 (s, 1H).

Example 44

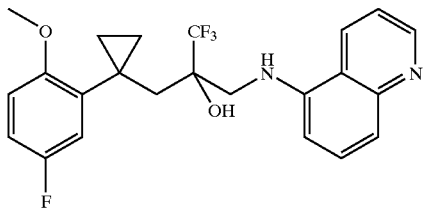

1-(Quinolin-5-ylamino)-3-[1-(5-fluoro-2-methoxyphenyl)cycloprop-1-yl]-2-(trifluoromethyl)propan-2-ol 1-(Quinolin-5-ylimino)-3-[1-(5-fluoro-2-methoxyphenyl)cycloprop-1-yl]-2-(trifluoromethyl)propan-2-ol Analogously to Example 37, 362 mg (2.5 mmol) of 5-aminoquinoline is reacted with 640 mg (2.09 mmol) of 3-[1-(5-fluoro-2-methoxyphenyl)cycloprop-1-yl]-2-hydroxy-2-(trifluoromethyl)propanal and 2.80 ml of concentrated acetic acid in 19 ml of toluene. After 6 hours, the chromatography is carried out on silica gel with hexane-ethyl acetate (0–100%), and 810 mg (90% of theory) of the product is obtained.

MS (ES+): m/z (r.I. %)=433 (M+1, 100).

1-(Quinolin-5-ylamino)-3-[1-(S-fluoro-2-methoxyphenyl)cycloprop-1-yl]-2-(trifluoromethyl)propan-2-ol 810 mg (1.87 mmol) of 1-(quinolin-5-ylimino)-3-[1-(5-fluoro-2-methoxyphenyl)cycloprop-1-yl]-2-(trifluoromethyl)propan-2-ol is reacted with 288 mg (7.61 mmol) of sodium borohydride in 6.0 ml of methanol and 3.0 ml of tetrahydrofuran as in Example 1. After chromatography on silica gel with hexane-ethyl acetate (0–100%), 660 mg (81% of theory) of the product is obtained.

¹H-NMR (400 MHz, CDCl₃): δ=0.85–0.99 (m, 4H), 2.19 (d, 1H), 2.32 (d, 1H), 3.19–3.29 (m, 2H), 3.70 (s, 3H), 3.83 (s, 1H), 4.47 (t, 1H), 6.31 (d, 1H), 6.61 (dd, 1H), 6.84 (ddd, 1H), 7.06 (dd, 1H), 7.33 (dd, 1H), 7.46–7.52 (m, 2H), 8.05 (d, 1H), 8.87 (dd, 1H).

Example 45

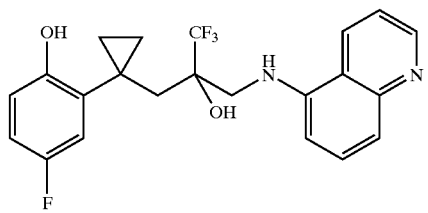

1-(Quinolin-5-ylamino)-3-[1-(5-fluoro-2-hydroxyphenl)cycloprop-1-yl]-2-(trifluoromethyl)propan-2-ol Analogously to Example 38, 330 mg (0.76 mmol) of 1-(quinolin-5-ylamino)-3-[1-(5-fluoro-2-methoxyphenyl)cycloprop-1-yl]-2-(trifluoromethyl)propan-2-ol is reacted with 3.80 ml (3.80 mmol) of a 1 M boron tribromide solution in 6.90 ml of dichloromethane. After 2 hours, the reaction is halted. The recrystallization from ethyl acetate and methanol yields 292 mg (91% of theory) of the product.

¹H-NMR (400 MHz, DMSO-d₆): δ=0.63–0.65 (m, 1H), 0.79–0.84 (m, 3H), 1.97 (d, 1H), 2.62 (d, 1H), 3.35 (m, 2H), 5.93 (br, 1H), 6.26 (br, 1H), 6.42 (dd, 1H), 6.51 (d, 1H), 6.64 (td, 1H), 6.91 (dd, 1H), 7.31 (d, 1H), 7.71 (t, 1H), 7.83 (dd, 1H), 9.08–9.12 (m, 2H), 9.34 (s, 1H).

Example 46

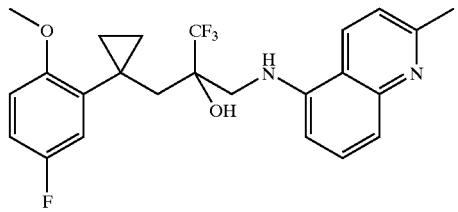

3-[1-(5-Fluoro-2-methoxyphenyl)cycloprop-1-yl]-1-(2-methylquinolin-5-ylamino)-2-(trifluoromethyl)propan-2-ol 3-[1-(5-Fluoro-2-methoxyphenyl)cycloprop-1-yl]-1-(2-methylquinolin-5-ylimino)-2-(trifluoromethyl)propan-2-ol Analogously to Example 1, 352 mg (2.23 mmol) of 5-amino-2-methylquinoline is reacted with 650 mg (2.12 mmol) of 3-[1-(5-fluoro-2-methoxyphenyl)cycloprop-1-yl]-2-hydroxy-2-(trifluoromethyl)propanal and 2.80 ml of concentrated acetic acid in 19 ml of toluene. After chromatography on silica gel with hexane-ethyl acetate (0–100%), 870 mg (92% of theory) of the product is obtained.

MS (ES+): m/z (r.I. %)=447 (M+1, 100).

3-[1-(5-Fluoro-2-methoxyphenyl)cycloprop-1-yl]-1-(2-methylquinolin-5-ylamino)-2-(trifluoromethyl)propan-2-ol 870 mg (1.95 mmol) of 3-[1-(5-fluoro-2-methoxyphenyl)cycloprop-1-yl]-1-(2-methylquinolin-5-ylimino)-2-(trifluoromethyl)propan-2-ol is reacted analogously to Example 37 with 96 mg (2.53 mmol) of sodium borohydride in 6.0 ml of methanol and 3.0 ml of tetrahydrofuran. After recrystallization from hexane and ethyl acetate, 790 mg (90% of theory) of the product is obtained.

$^1$H-NMR (400 MHz, CDCl$_3$): δ=0.83–0.97 (m, 4H), 2.19 (d, 1H), 2.31 (d, 1H), 2.72 (s, 3H), 3.21–3.25 (m, 2H), 3.70 (s, 3H), 3.79 (s, 1H), 4.41 (t, 1H), 6.25 (dd, 1H), 6.61 (dd, 1H), 6.86 (ddd, 1H), 7.05 (dd, 1H), 7.21 (d, 1H), 7.43–7.44 (m, 2H), 7.94 (d, 1H).

Example 47

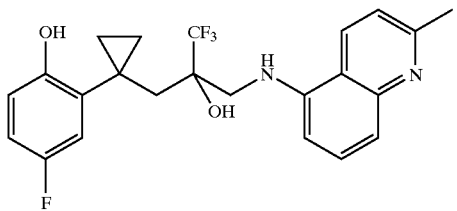

3-[1-(5-Fluoro-2-hydroxyphenyl)cycloprop-1-yl]-1-(2-methylquinolin-5-ylamino)-2-(trifluoromethyl)propan-2-ol Analogously to Example 38, 395 mg (0.88 mmol) of 3-[1-(5-fluoro-2-methoxyphenyl)cycloprop-1-yl]-1-(2-methylquinolin-5-ylamino)-2-(trifluoromethyl)propan-2-ol is reacted with 4.30 ml (4.3 mmol) of a 1 M boron tribromide solution in 8.0 ml of dichloromethane. After one hour at 0° C., the reaction is halted. The subsequent recrystallization from ethyl acetate, acetone and methanol yields 257 mg (67% of theory) of the product.

MS (ES+): m/z (r.I.%)=435 (M+1, 100).

Example 48

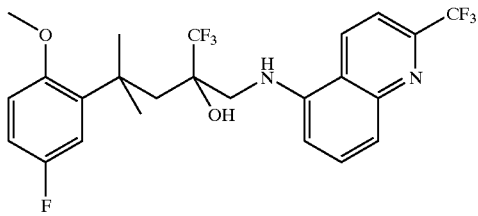

4-(5-Fluoro-2-methoxyphenyl)-4-methyl-2-trifluoromethyl-1-(2-(trifluoromethyl)quinolin-5-ylamino)pentan-2-ol 2-(Trifluoromethyl)quinoline According to instructions in the literature (Baraznenok, I. L., Nenajdenko, V. G., Balenkova, E. S. Eur. J. Org. Chem. 1999, 937–941), 1.2 g (7.18 mmol) of (E)-4-(dimethylamino)-1,1,1-trifluoro-3-buten-2-one is reacted with 2.03 g (7.18 mmol) of trifluoroacetic acid anhydride and 1.30 ml (14.36 mmol) of aniline in 72 ml of 1,2-dichloroethane, then in 36 ml of xylene. After working-up and purification on silica gel with hexane-ethyl acetate (0–100%), 1.01 g (71% of theory) of the product is obtained.

5-Nitro-2-(trifluoromethyl)quinoline 1.52 g (7.7 mmol) of 2-(trifluoromethyl)quinoline is dissolved in 7.90 ml of concentrated sulfuric acid, and 1.47 g of potassium nitrate is added in portions at 0° C. After 20 hours at room temperature, the reaction solution is poured onto ice/water. It is extracted with ethyl acetate, the combined organic phases are washed with saturated sodium bicarbonate solution and dried on sodium sulfate. After removal of the solvent and chromatography on silica gel with hexane-ethyl acetate (10–100%), 390 mg (21% of theory) of the product is obtained.

$^1$H-NMR (300 MHz, CDCl$_3$): δ=7.92–8.00 (m, 2H), 8.53–8.58 (m, 2H), 9.26 (d, 1H).

5-Amino-2-(trifluoromethyl)quinoline 390 mg (1.61 mmol) of 5-nitro-2-(trifluoromethyl)quinoline is dissolved in 13 ml of methanol. After the addition of 39 mg of palladium on carbon and 19 mg of potassium carbonate, the reaction mixture is allowed to stir for 20 hours at room temperature under hydrogen atmosphere. It is then filtered on Celite and washed with ethyl acetate. After the solvent is removed in a vacuum and after chromatography on silica gel with hexane-ethyl acetate (0–100%), 250 mg (73% of theory) of the product is obtained.

$^1$H-NMR (300 MHz, CDCl$_3$): δ=4.28 (br, 2H), 6.92 (d, 1H), 7.58–7.69 (m, 3H), 8.36 (d, 1H).

4-(5-Fluoro-2-methoxyphenyl)-4-methyl-2-trifluoromethyl-1-(2-(trifluoromethyl)quinolin-5-ylimino)pentan-2-ol Analogously to Example 37, 250 mg (1.18 mmol) of 5-amino-2-(trifluoromethyl)quinoline is reacted with 438 mg (1.42 mmol) of 4-(5-fluoro-2-methoxyphenyl)-2-hydroxy-4-methyl-2-(trifluoromethyl)pentanal and 1.30 ml of concentrated acetic acid in 20 ml of toluene. After chromatography on silica gel with hexane-ethyl acetate (0–100%), 500 mg (84% of theory) of the product is obtained.

$^1$H-NMR (300 MHz, CDCl$_3$): δ=1.38 (s, 3H), 1.58 (s, 3H), 2.31 (d, 1H), 3.47 (d, 1H), 3.80 (s, 3H), 4.75 (s, 1H), 6.39–6.45 (m, 1H), 6.51–6.58 (m, 2H), 6.82 (dd, 1H), 7.55 (s, 1H), 7.64 (t, 1H), 7.78 (d, 1H), 8.10 (d, 1H), 8.49 (d, 1H).

4-(5-Fluoro-2-methoxyphenyl)-4-methyl-2-trifluoromethyl-1-(2-(trifluoromethyl)-quinolin-5-ylamino)pentan-2-ol Analogously to Example 37, 500 mg (0.99 mmol) of 4-(5-fluoro-2-methoxyphenyl)-4-methyl-2-trifluoromethyl-1-(2-(trifluoromethyl)quinolin-5-ylimino)-pentan-2-ol is reacted with 154 mg (4.04 mmol) of sodium borohydride in 5.0 ml of methanol. After purification on silica gel with hexane-ethyl acetate (0–100%), 420 mg (84% of theory) of the product is obtained.

$^1$H-NMR (300 MHz, CDCl$_3$): δ=1.47 (s, 3H), 1.55 (s, 3H), 2.42 (d, 1H), 2.74 (d, 1H), 3.03 (s, 1H), 3.16 (dd, 1H), 3.34 (dd, 1H), 3.85 (s, 3H), 4.38 (dd, 1H), 6.20 (d, 1H), 6.79 (dd, 1H), 6.91–6.97 (m, 1H), 7.10 (dd, 1H), 7.52–7.65 (m, 3H), 8.14 (d, 1H).

Example 49

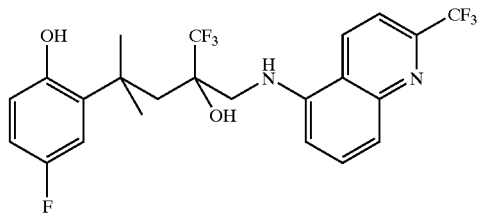

4-(5-Fluoro-2-hydroxyphenyl)-4-methyl-2-trifluoromethyl-1-(2-(trifluoromethyl)-quinolin-5-ylamino)pentan-2-ol 100 mg (0.20 mmol) of 4-(5-fluoro-2-methoxyphenyl)-4-methyl-2-trifluoromethyl-1-(2-(trifluoromethyl)quinolin-5- ylamino)pentan-2-ol in 2.0 ml of dichloromethane is mixed at room temperature with 4.0 ml (4.0 mmol) of a 1 M boron tribromide solution. After 20 hours at room temperature, the reaction is brought to a halt by adding 20 ml of methanol. The reaction mixture is allowed to stir for 30 minutes at room temperature, and then the solvent is removed in a vacuum. After chromatography on silica gel with hexane-ethyl acetate (0–100%), 79 mg (80% of theory) of the product is obtained.

$^1$H-NMR (300 MHz, CDCl$_3$): δ=1.51 (s, 3H), 1.57 (s, 3H), 2.45 (d, 1H), 2.76 (d, 1H), 3.21–3.27 (m, 2H), 3.42 (dd, 1H), 4.43 (br, 1H), 5.60 (br, 1H), 6.23 (d, 1H), 6.59 (dd, 1H), 6.75–6.87 (m, 1H), 7.07 (dd, 1H), 7.51–7.65 (m, 3H), 8.14 (d, 1H).

Example 50

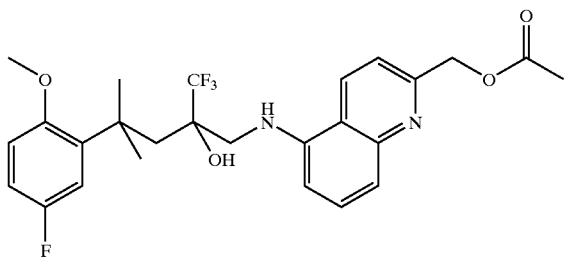

1-(2-(Acetoxymethyl)quinolin-5-ylamino)-4-(5-fluoro-2-methoxyphenyl)-4-methyl-2-(trifluoromethyl)pentan-2-ol 1-(1,2-Dihydroxyethyl)-5-nitroquinoline 336 mg (2.5 mmol) of N-methylmorpholine-N-oxide hydrate and 10.22 ml of osmium tetroxide solution in isopropanol are added at 0° C. to a solution that consists of 3.18 g (15.88 mmol) of 5-nitro-2-vinylquinoline in 140 ml of acetone and 21 ml of water, and the reaction mixture is stirred for 24 hours at room temperature. Then, the solvent is removed in a vacuum, and the residue is taken up in ethyl acetate. The organic phase is washed with water and saturated sodium chloride solution. The aqueous phase is extracted repeatedly with dichloromethane, diethyl ether and ethyl acetate. The combined organic phases are dried on sodium sulfate. After removal of the solvent and purification of silica gel with hexane-ethyl acetate (0–100%) as well as with ethyl acetate-methanol (0–20%), 1.64 g (44% of theory) of the product is obtained.

$^1$H-NMR (300 MHz, DMSO-d$_6$): δ=3.62–3.81 (m, 2H), 4.78–4.84 (m, 2H), 5.76 (d, 1H), 7.90–7.96 (m, 2H), 8.37–8.42 (m, 2H), 8.83 (d, 1H).

5-Nitroquinoline-2-carbaldehyde 2.99 g (14.0 mmol) of sodium periodate is added to a solution that consists of 1.64 g (7.0 mmol) of 1-(1,2-dihydroxyethyl)-5-nitroquinoline in 42 ml of tetrahydrofuran and 7.0 ml of water. After 20 hours at room temperature, ethyl acetate is added, and the organic phase is washed with saturated sodium chloride solution. After the organic phase is dried on sodium sulfate, after the solvent is removed, and after purification on silica gel with hexane-ethyl acetate (0–100%), 1.40 g (99% of theory) of the product is obtained.

$^1$H-NMR (300 MHz, CDCl$_3$): δ=7.94 (t, 1H), 8.24 (d, 1H), 8.53 (d, 1H), 8.58 (d, 1H), 9.18 (d, 1H), 10.24 (s, 1H).

2-(Hydroxymethyl)-5-nitroquinoline 700 mg (3.46 mmol) of 5-nitroquinoline-2-carbaldehyde are dissolved in 13 ml of methanol and 7.0 ml of tetrahydrofuran and mixed at 0° C. with 523 mg (13.9 mmol) of sodium borohydride. After 5 hours, the reaction is brought to a halt by adding water. The solvent is removed in a vacuum, the residue is taken up in dichloromethane and water, the aqueous phase is extracted with dichloromethane, and the combined organic phases are dried on sodium sulfate. After the solvent is removed, and after purification on silica gel with hexane-ethyl acetate (0–100%), 390 mg (55% of theory) of the product is obtained.

$^1$H-NMR (300 MHz, CDCl$_3$): δ=4.13 (br, 1H), 4.99 (s, 2H), 7.55 (d, 1H), 7.82 (t, 1H), 8.36–8.41 (m, 2H), 8.99 (d, 1H).

2-(Acetoxymethyl)-5-nitroquinoline

A solution that consists of 390 mg (1.91 mmol) of 2-(hydroxymethyl)-5-nitroquinoline and 2.5 ml of acetic acid anhydride in 5.0 ml of pyridine is allowed to stir for 24 hours at room temperature. After repeated co-evaporation with toluene and subsequent chromatography on silica gel with hexane-ethyl acetate (0–100%), 410 mg (87% of theory) of the product is obtained.

$^1$H-NMR (300 MHz, CDCl$_3$): δ=2.23 (s, 3H), 5.42 (s, 2H), 7.70 (d, 1H), 7.81 (t, 1H), 8.37–8.40 (m, 2H), 9.02 (d, 1H).

2-(Acetoxymethyl)-5-aminoquinoline

Under hydrogen atmosphere, a solution that consists of 410 mg (1.67 mol) of 2-(acetoxymethyl)-5-nitroquinoline in 61 ml of acetone can be stirred in the presence of 410 mg of Raney nickel for 2 hours at room temperature. It is suctioned off on Celite and rewashed with acetone. After removal of the solvent and subsequent chromatography on silica gel with hexane-ethyl acetate (10–100%), 230 mg (64% of theory) of the product is obtained.

$^1$H-NMR (300 MHz, CDCl$_3$): δ=2.19 (s, 3H), 4.20 (br, 2H), 5.37 (s, 2H), 6.81 (dd, 1H), 7.41 (d, 1H), 7.51–7.53 (m, 2H), 8.19 (d, 1H).

1-(2-(Acetoxymethyl)quinolin-5-ylimino)-4-(5-fluoro-2-methoxyphenyl)-4-methyl-2-(trifluoromethyl)pentan-2-ol Analogously to Example 37, 230 mg (1.06 mmol) of 2-(acetoxymethyl)-5-aminoquinoline is reacted with 273 mg (0.88 mmol) of 4-(5-fluoro-2-methoxyphenyl)-2-hydroxy-4-methyl-2-(trifluoromethyl)pentanal and 1.20 ml of concentrated acetic acid in 20.0 ml of toluene. After chromatography on silica gel with hexane-ethyl acetate (0–100%), 360 mg (81% of theory) of the product is obtained.

$^1$H-NMR (300 MHz, CDCl$_3$): δ=1.37 (s, 3H), 1.57 (s, 3H), 2.21 (s, 3H), 2.32 (d, 1H), 3.44 (d, 1H), 3.79 (s, 3H), 4.84 (s, 1H), 5.40 (s, 2H), 6.42–6.56 (m, 3H), 6.82 (dd, 1H), 7.45–7.60 (m, 3H), 7.95 (d, 1H), 8.31 (d, 1H).

1-(2-(Acetoxymethyl)quinolin-5-ylamino)-4-(S-fluoro-2-methoxyphenyl)-4-methyl-2-(trifluoromethyl)pentan-2-ol A solution that consists of 170 mg (0.34 mmol) of 1-(2-(acetoxymethyl)quinolin-5-ylimino)-4-(5-fluoro-2-methoxyphenyl)-4-methyl-2-(trifluoromethyl)pentan-2-ol in 1.5 ml of methanol and 0.8 ml of tetrahydrofuran is mixed with 53 mg (1.38 mmol) of sodium borohydride. After 3 hours at room temperature, the reaction is halted by adding water. It is extracted with ethyl acetate, the combined organic phases are washed with saturated sodium chloride solution and dried on sodium sulfate. After removal of the solvent and chromatography on silica gel with hexane-ethyl acetate (0–100%), 94 mg (55% of theory) of the product is obtained.

$^1$H-NMR (300 MHz, CDCl$_3$): δ=1.46 (s, 3H), 1.56 (s, 3H), 2.19 (s, 3H), 2.35 (d, 1H), 2.77 (d, 1H), 3.10–3.16 (m, 2H), 3.31 (dd, 1H), 3.84 (s, 3H), 4.28 (dd, 1H), 5.36 (s, 2H), 6.07 (d, 1H), 6.80 (dd, 1H), 6.91–6.98 (m, 1H), 7.11 (dd, 1H), 7.37–7.53 (m, 3H), 7.99 (d, 1H).

Example 51

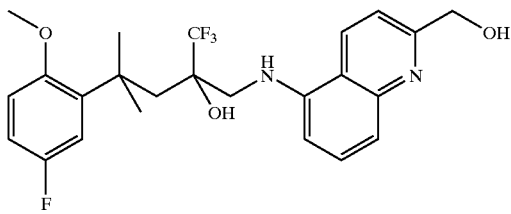

4-(5-Fluoro-2-methoxyphenyl)-1-(2-(hydroxymethyl)quinolin-5-ylamino)-4-methyl-2-(trifluoromethyl)pentan-2-ol In the reaction of 170 mg (0.34 mmol) of 1-(2-(acetoxymethyl)quinolin-5-ylamino)-4-(5-fluoro-2-methoxyphenyl)-4-methyl-2-(trifluoromethyl)pentan-2-ol with 53 mg (1.38 mmol) of sodium borohydride in 1.5 ml of methanol and 0.8 ml of tetrahydrofuran, 43 mg (27% of theory) of the product is obtained (cf. Example 14).

$^1$H-NMR (300 MHz, CDCl$_3$): δ=1.46 (s, 3H), 1.57 (s, 3H), 2.35 (d, 1H), 2.77 (d, 1H), 3.10–3.16 (m, 2H), 3.32 (dd, 1H), 3.84 (s, 3H), 4.29 (dd, 1H), 4.41 (br, 1H), 4.89 (s, 2H), 6.07 (d, 1H), 6.79 (dd, 1H), 6.91–6.97 (m, 1H), 7.12 (dd, 1H), 7.20 (d, 1H), 7.42–7.51 (m, 2H), 7.95 (d, 1H).

Example 52

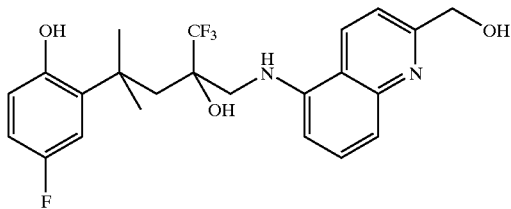

4-(5-Fluoro-2-hydroxyphenyl)-1-(2-(hydroxymethyl)quinolin-5-ylamino)-4-methyl-2-(trifluoromethyl)pentan-2-ol 290 mg (0.62 mmol) of 4-(5-fluoro-2-methoxyphenyl)-1-(2-(hydroxymethyl)quinolin-5-ylamino)-4-methyl-2-(trifluoromethyl)pentan-2-ol in 7.0 ml of dichloromethane is mixed at room temperature with 12.5 ml (12.5 mmol) of a 1 M boron tribromide solution. After 20 hours at room temperature, the reaction is brought to a halt by adding methanol. The solvent is removed in a vacuum, the residue is taken up in saturated sodium bicarbonate solution and ethyl acetate, extracted with ethyl acetate, and the combined organic phases are dried on sodium sulfate. After the solvent is removed and after purification on silica gel with hexane-ethyl acetate (0–70%) as well as with ethyl acetate-methanol (0–10%), 160 mg (51% of theory) of the product is obtained.

$^1$H-NMR (300 MHz, DMSO-d$_6$): δ=1.46 (s, 3H), 1.56 (s, 3H), 1.93 (d, 1H), 2.94 (dd, 1H), 3.09–3.21 (m, 2H), 4.67 (d, 2H), 5.34–5.37 (m, 1H), 5.51 (t, 1H), 5.91 (d, 1H), 5.98 (s, 1H), 6.73 (dd, 1H), 6.81–6.87 (m, 1H), 7.01 (dd, 1H), 7.14 (d, 1H), 7.32 (t, 1H), 7.54 (d, 1H), 8.28 (d, 1H), 9.74 (s, 1H).

Example 53

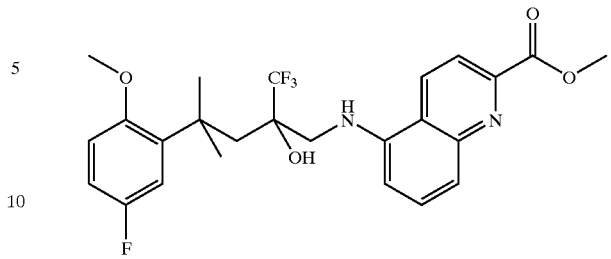

5-[4-(5-Fluoro-2-methoxyphenyl)-2-hydroxy-4-methyl-2-(trifluoromethyl)pentylamino]quinoline-2-carboxylic acid methyl ester 5-Aminoquinoline-2-carboxylic acid methyl ester At 0° C., 2.8 g (mmol) of potassium nitrate is added in portions to a solution that consists of 3.5 g (20.21 mmol) of quinoline-2-carboxylic acid in 12 ml of concentrated sulfuric acid. After 4 days at room temperature, the reaction mixture is poured onto ice water. The precipitated solid is suctioned off, washed with a little water and dried under high vacuum. The crude product is dissolved in 50 ml of methanol. After adding 10 ml of concentrated sulfuric acid, the reaction solution is allowed to reflux for 4 hours, then stirred for 36 hours at room temperature. The reaction solution is concentrated by evaporation to one third of the original volume and added to ice water. It is extracted with ethyl acetate, the combined organic phases are washed with saturated sodium bicarbonate solution, then with saturated sodium chloride solution, it is dried on sodium sulfate, and the solvent is removed in a vacuum. The crude product is dissolved in 80 ml of methanol-acetone (50%) and mixed with palladium on carbon and potassium carbonate. It is stirred for 20 hours under hydrogen atmosphere at room temperature. After suctioning off on Celite and washing with acetone, the solvent is removed in a vacuum, and the residue is purified on silica gel with hexane/ethyl acetate (0–60%). 850 mg (27% of theory) of the product is obtained.

$^1$H-NMR (300 MHz, CDCl$_3$): δ=4.07 (s, 3H), 6.90 (d, 1H), 7.58 (t, 1H), 7.75 (d, 1H), 8.12 (d, 1H), 8.33 (d, 1H).

5-[4-(5-Fluoro-2-methoxyphenyl)-2-hydroxy-4-methyl-2-(trifluoromethyl)pentylidenamino]-quinoline-2-carboxylic acid methyl ester Analogously to Example 37, 200 mg (1.0 mmol) of 5-aminoquinoline-2-carboxylic acid methyl ester is reacted with 371 mg (1.2 mmol) of 4-(5-fluoro-2-methoxyphenyl)-2-hydroxy-4-methyl-2-(trifluoromethyl)pentanal and 1.10 ml of concentrated acetic acid in 20 ml of toluene. After chromatography on silica gel with hexane-ethyl acetate (0–100%), 420 mg (85% of theory) of the product is obtained.

$^1$H-NMR (300 MHz, CDCl$_3$): δ=1.38 (s, 3H), 1.59 (s, 3H), 2.29 (d, 1H), 3.47 (d, 1H), 3.80 (s, 3H), 4.10 (s, 3H), 4.79 (s, 1H), 6.40–6.45 (m, 1H), 6.53–6.56 (m, 2H), 6.81 (dd, 1H), 7.54 (s, 1H), 7.60 (t, 1H), 8.18 (d, 1H), 8.23 (d, 1H), 8.45 (d, 1H).

5-[4-(5-Fluoro-2-methoxyphenyl)-2-hydroxy-4-methyl-2-(trifluoromethyl)pentylamino]quinoline-2-carboxylic acid methyl ester Analogously to Example 40, 420 mg (0.85 mmol) of 5-[4-(5-fluoro-2-methoxyphenyl)-2-hydroxy-4-methyl-2-(trifluoromethyl)pentylidenamino] quinoline-2-carboxylic acid methyl ester is dissolved in 10 ml of methanol and mixed with 130 mg (3.41 mmol) of sodium borohydride.

After chromatography on silica gel with hexane-ethyl acetate (0–100%), 75 mg (18% of theory) of the product is obtained.

¹H-NMR (300 MHz, CDCl₃): δ=1.46 (s, 3H), 1.56 (s, 3H), 2.36 (d, 1H), 2.78 (d, 1H), 3.04 (s, 1H), 3.15 (dd, 1H), 3.50 (dd, 1H), 3.84 (s, 3H), 4.08 (s, 3H), 4.35 (dd, 1H), 6.16 (d, 1H), 6.77 (dd, 1H), 6.89–6.95 (m, 1H), 7.10 (dd, 1H), 7.52 (t, 1H), 7.71 (d, 1H), 8.11 (s, 2H).

Example 54

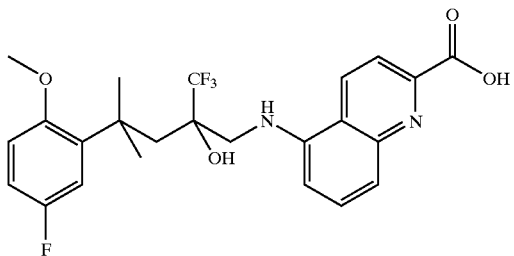

5-[4-(5-Fluoro-2-methoxyphenyl)-2-hydroxy-4-methyl-2-(trifluoromethyl)pentylamino]quinoline-2-carboxylic acid A solution that consists of 60 mg (0.12 mmol) of 5-[4-(5-fluoro-2-methoxyphenyl)-2-hydroxy-4-methyl-2-(trifluoromethyl)pentyamino]quinoline-2-carboxylic acid methyl ester in 10 ml of methanol is mixed with 0.5 ml (0.5 mmol) of 1N sodium hydroxide solution. After 2.5 hours, the solvent is removed in a vacuum, and the residue is purified on silica gel with dichloromethane-methanol (6–25%). 47 mg (82% of theory) is obtained.

¹H-NMR (300 MHz, DMSO-d₆): δ=1.38 (s, 3H), 1.54 (s, 3H), 2.04 (d, 1H), 2.91–3.06 (m, 3H), 3.75 (s, 3H), 5.49 (br, 1H), 5.94 (d, 1H), 6.11 (br, 1H), 6.83–6.88 (m, 1H), 6.93–6.97 (m, 1H), 7.07 (dd, 1H), 7.34 (t, 1H), 7.44 (d, 1H), 8.00 (d, 1)H), 8.38 (d, 1H).

Example 55

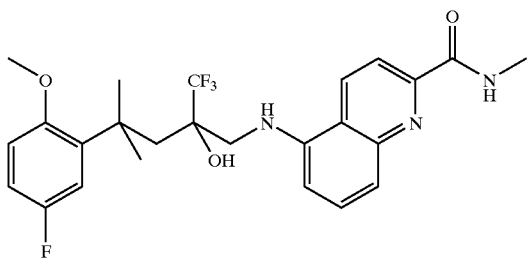

5-[4-(5-Fluoro-2-methoxyphenyl)-2-hydroxy-4-methyl-2-trifluoromethylpentylamino]-quinoline-2-carboxylic acid methylamide 5-Aminoquinoline-2-carboxylic acid methylamide 76 mg (0.376 mmol) of 5-aminoquinoline-2-carboxylic acid methyl ester is dissolved with 10 ml of a 2.0 M methanolic methylamine solution. After 90 minutes under reflux and another 16 hours at room temperature, the solvent is removed under reduced pressure, and the residue is purified on silica gel with hexane-ethyl acetate (0–80%). 72 mg (95% of theory) of the product is obtained.

¹H-NMR (300 MHz, DMSO-d₆): δ=2.87 (d, 3H), 6.10 (s, 2H), 6.77 (d, 1H), 7.27 (d, 1H), 7.51 (t, 1H), 7.95 (d, 1H), 8.68 (d, 1H), 8.79–8.80 (m, 1H).

5-[4-(5-Fluoro-2-methoxyphenyl)-2-hydroxy-4-methyl-2-(trifluoromethyl)-pentylidenamino]-quinoline-2-carboxylic acid methylamide Analogously to Example 37, 220 mg (1.08 mmol) of 5-aminoquinoline-2-carboxylic acid-methylamide is reacted with 550 mg (1.78 mmol) of 4-(5-fluoro-2-methoxyphenyl)-2-hydroxy-4-methyl-2-(trifluoromethyl)pentanal and 3.0 ml of concentrated acetic acid in 30 ml of toluene. After chromatography on silica gel with hexane-ethyl acetate (0–70%), 259 mg (48% of theory) of the product is obtained.

¹H-NMR (300 MHz, CDCl₃): δ=1.37 (s, 3H), 1.56 (s, 3H), 2.29 (d, 1H), 3.11 (d, 3H), 3.48 (d, 1H), 3.81 (s, 3H), 4.81 (s, 1H), 6.46–6.49 (m, 2H), 6.57 (dd, 1H), 6.78 (dd, 1H), 7.50 (s, 1H), 7.56 (t, 1H), 7.95 (d, 1H), 8.23 (br, 1H), 8.34 (d, 1H), 8.46 (d, 1H).

5-[4-(5-Fluoro-2-methoxyphenyl)-2-hydroxy-4-methyl-2-(trifluoromethyl)pentylamino]-quinoline-2-carboxylic acid methylamide 155 mg (0.315 mmol) of 5-[4-(5-fluoro-2-methoxyphenyl)-2-hydroxy-4-methyl-2-(trifluoromethyl)pentylidenamino]quinoline-2-carboxylic acid methylamide is dissolved in 10 ml of ethanol and mixed with 0.09 ml (0.4 mmol) of titanium tetraethylate as well as 94 mg (2.6 mmol) of sodium borohydride. The reaction is halted after 5 hours by adding saturated sodium chloride solution and ethyl acetate. Insoluble components are filtered. The filtrate is extracted with ethyl acetate, the combined organic phases are dried on sodium sulfate, and the solvent is removed in a vacuum. After chromatography on silica gel with hexane-ethyl acetate (0–50%), 110 mg (71% of theory) of the product is obtained.

¹H-NMR (300 MHz, DMSO-d₆): δ=1.38 (s, 3H), 1.56 (s, 3H), 2.06 (d, 1H), 2.86–2.97 (m, 5H), 3.07 (dd, 1H), 3.78 (s, 3H), 5.98 (s, 1H), 6.03 (d, 1H), 6.86–7.05 (m, 2H), 7.07 (dd, 1H), 7.32 (d, 1H), 7.46 (t, 1H), 8.03 (d, 1H), 8.49 (d, 1H), 8.81 (q, 1H).

Example 56

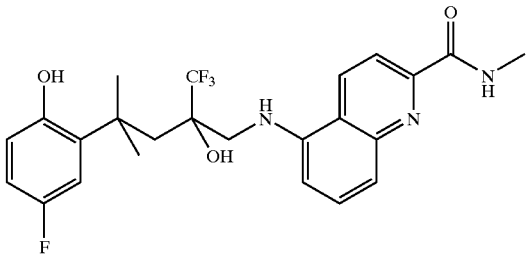

5-[4-(5-Fluoro-2-hydroxyphenyl)-2-hydroxy-4-methyl-2-(trifluoromethyl)pentylamino]-quinoline-2-carboxylic acid methylamide Analogously to Example 38, 97 mg (0.197 mmol) of 5-[4-(5-fluoro-2-methoxyphenyl)-2-hydroxy-4-methyl-2-(trifluoromethyl)pentylamino]quinoline-2-carboxylic acid methylamide is reacted with 8.0 ml (8.0 mmol) of a 1 M boron tribromide solution. After working-up and purification on silica gel with hexane-ethyl acetate (0–70%), 18 mg (18% of theory) of the product is obtained.

¹H-NMR (300 MHz, DMSO-d₆): δ=1.40 (s, 3H), 1.57 (s, 3H), 1.93 (d, 1H), 2.87 (d, 3H), 2.97 (dd, 1H), 3.13–3.20 (m, 2H), 5.51–5.54 (m, 1H), 5.98 (s, 1H), 6.04 (d, 1H), 6.67 (dd, 1H), 6.76–6.83 (m, 1H), 7.00 (dd, 1H), 7.32 (d, 1H), 7.45 (t, 1H), 8.03 (d, 1H), 8.46 (d, 1H), 8.80–8.82 (m, 1H), 9.72 (br, 1H).

Example 57

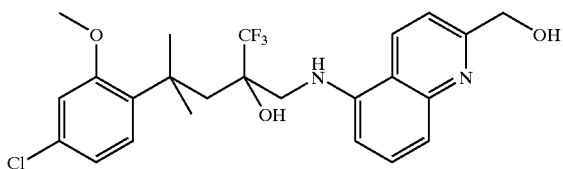

4-(4-Chloro-2-methoxyphenyl)-1-(2-(hydroxymethyl)quinolin-5-ylamino)-4-methyl-2-(trifluoromethyl)pentan-2-ol 5-[4-(4-Chloro-2-methoxyphenyl)-2-hydroxy-4-methyl-2-(trifluoromethyl)pentylidenamino]quinoline-2-carboxylic acid methyl ester Analogously to Example 1, 250 mg (1.24 mmol) of 5-aminoquinoline-2-carboxylic acid methyl ester is reacted with 484 mg (1.49 mmol) of 4-(4-chloro-2-methoxyphenyl)-2-hydroxy-4-methyl-2-(trifluoromethyl)pentanal and 1.40 ml of concentrated acetic acid in 20 ml of toluene. After chromatography on silica gel with hexane-ethyl acetate (0–100%), 500 mg (79% of theory) of the product is obtained.

$^1$H-NMR (300 MHz, CDCl$_3$): δ=1.36 (s, 3H), 1.58 (s, 3H), 2.28 (d, 1H), 3.45 (d, 1H), 3.84 (s, 3H), 4.11 (s, 3H), 4.79 (s, 1H), 6.38 (d, 1H), 6.48 (dd, 1H), 6.67 (d, 1H), 7.00 (d, 1H), 7.52 (s, 1H), 7.65 (dd, 1H), 8.18–8.25 (m, 2H), 8.48 (d, 1H).

4-(4-Chloro-2-methoxyphenyl)-1-(2-(hydroxymethyl)quinolin-5-ylamino)-4-methyl-2-(trifluoromethyl)pentan-2-ol Analogously to Example 40, 200 mg (0.39 mmol) of 5-[4-(4-chloro-2-methoxy-phenyl)-2-hydroxy-4-methyl-2-(trifluoromethyl)pentylidenamino]quinoline-2-carboxylic acid methyl ester is dissolved in 5.0 ml of methanol and mixed with 60 mg (1.56 mmol) of sodium borohydride. After chromatography on silica gel with hexane-ethyl acetate (0–100%), 70 mg (37% of theory) of the product is obtained.

$^1$H-NMR (300 MHz, DMSO-d$_6$): δ=1.37 (s, 3H), 1.55 (s, 3H), 2.04 (d, 1H), 2.82–2.91 (m, 2H), 2.98–3.02 (m, 1H), 3.81 (s, 3H), 4.67 (d, 2H), 5.39–5.42 (m, 1H), 5.49 (t, 1H), 5.87 (d, 1H), 5.95 (s, 1H), 6.95 (dd, 1H), 7.01 (d, 1H), 7.17 (d, 1H), 7.29–7.37 (m, 2H), 7.53–7.55 (d, 1H), 8.29 (d, 1H).

Example 58

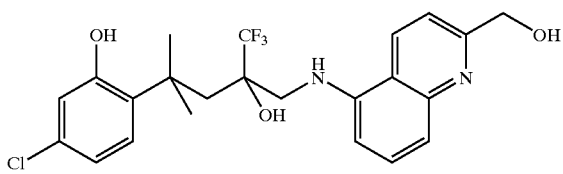

4-(4-Chloro-2-hydroxyphenyl)-1-(2-(hydroxymethyl)quinolin-5-ylamino)-4-methyl-2-(trifluoromethyl)pentan-2-ol Analogously to Example 38, 110 mg (0.23 mmol) of 4-(4-chloro-2-methoxyphenyl)-1-(2-(hydroxymethyl)quinolin-5-ylamino)-4-methyl-2-(trifluoromethyl)pentan-2-ol is reacted with 4.60 ml (4.60 mmol) of a 1 M boron tribromide solution. After working-up and purification on silica gel with hexane-ethyl acetate (0–100%) as well as with ethyl acetate-methanol (0–20%), 54 mg (50% of theory) of the product is obtained.

$^1$H-NMR (300 MHz, DMSO-d$_6$): δ=1.39 (s, 3H), 1.57 (s, 3H), 1.94 (d, 1H), 2.91 (dd, 1H), 3.04–3.13 (m, 2H), 4.67 (d, 2H), 5.34–5.37 (m, 1H), 5.50 (t, 1H), 5.87 (d, 1H), 5.97 (s, 1H), 6.80–6.83 (m, 2H), 7.16 (d, 1H), 7.34 (t, 1H), 7.53 (d, 1H), 8.27 (d, 1H), 10.20 (s, 1H).

Example 59

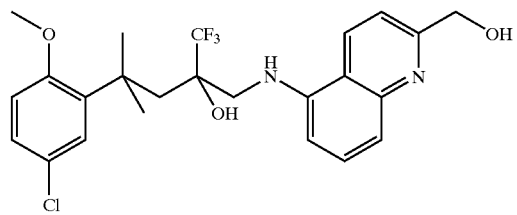

4-(5-Chloro-2-methoxyphenyl)-1-(2-(hydroxymethyl)quinolin-5-ylamino)-4-methyl-2-(trifluoromethyl)pentan-2-ol 5-[4-(5-Chloro-2-methoxyphenyl)-2-hydroxy-4-methyl-2-(trifluoromethyl)pentylidenamino]quinoline-2-carboxylic acid methyl ester 224 mg (0.69 mmol) of 4-(5-chloro-2-methoxyphenyl)-2-hydroxy-4-methyl-2-(trifluoromethyl)pentanal and 195 mg (0.96 mmol) of 5-aminoquinoline-2-carboxylic acid methyl ester are dissolved in 20 ml of toluene. After 5.0 ml of concentrated acetic acid is added, it is refluxed for 16 hours in a water separator. After the solvent is removed, the residue is taken up in 10 ml of tetrahydrofuran, 0.3 ml (1.4 mmol) of titanium tetraethylate is added, and the reaction is allowed to reflux again. After the solvent is removed as well as after purification on silica gel with hexane/ethyl acetate (0–100%), 120 mg (33% of theory) of the product is obtained.

$^1$H-NMR (300 MHz, CDCl$_3$): δ=1.37 (s, 3H), 1.51 (t, 3H), 1.57 (s, 3H), 2.99 )d, 1H), 3.49 (d, 1H), 3.81 (s, 3H), 4.57 (q, 2H), 4.83 (s, 1H), 6.52–6.58 (m, 1H), 6.79 (dd, 1H), 7.02 (d, 1H), 7.51 (s, 1H), 7.61 (t, 1H), 8.18–8.26 (m, 2H), 8.46 (d, 1H).

4-(5-Chloro-2-methoxyphenyl)-1-(2-(hydroxymethyl)quinolin-5-ylamino)-4-methyl-2-(trifluoromethyl)pentan-2-ol Analogously to Example 40, 120 mg (0.23 mmol) of 5-[4-(5-chloro-2-methoxyphenyl)-2-hydroxy-4-methyl-2-trifluoromethylpentylidenamino]-quinoline-2-carboxylic acid ethyl ester is reacted with 35 mg (0.92 mmol) of sodium borohydride. After working-up and purification on silica gel with hexane-ethyl acetate (0–100%) as well as with ethyl acetate-methanol (0–20%), 61 mg (55% of theory) of the product is obtained.

$^1$H-NMR (300 MHz, CDCl$_3$): δ=1.47 (s, 3H), 1.59 (s, 3H), 2.29 (d, 1H), 2.82 (d, 1H), 3.05–3.16 (m, 2H), 3.29–3.36 (m, 1H), 4.23–4.26 (m, 1H), 4.32–4.52 (br, 1H), 4.88 (s, 2H), 6.04–6.06 (m, 1H), 6.79 (d, 1H), 7.18–7.21 (m, 2H), 7.36 (d, 1H), 7.48–7.50 (m, 2H), 7.95 (d, 1H).

Example 60

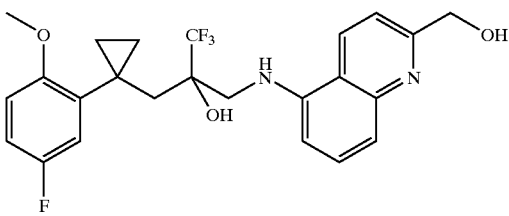

3-[1-(5-Fluoro-2-methoxyphenyl)cycloprop-1-yl]-1-(2-(hydroxymethyl)quinolin-5-ylamino)-2-(trifluoroethyl)propan-2-ol 5-{3-[1-(5-Fluoro-2-methoxyphenyl)cycloprop-1-yl]-2-hydroxy-2-(trifluoromethyl)propylidenamino}quinoline-2-carboxylic acid methyl ester Analogously to Example 37, 306 mg (1.2 mmol) of 5-{3-[1-(5-fluoro-2-methoxyphenyl)cycloprop-1-yl]-2-hydroxy-2-(trifluoromethyl)propanal is reacted with 170 mg (0.84 mmol) of 5-aminoquinoline-2-carboxylic acid methyl ester in 4.0 ml of concentrated acetic acid and 20 ml of toluene. After working-up and purification on silica gel with hexane-ethyl acetate (0–70%), 204 mg (49% of theory) of the product is obtained.

$^1$H-NMR (300 MHz, CDCl$_3$): δ=0.61–0.68 (m, 1H), 0.76–0.80 (m, 1H), 0.94–1.00 (m, 1H), 1.06–1.12 (m, 1H), 2.16 (d, 1H), 2.90 (d, 1H), 3.84 (s, 3H), 4.10 (s, 3H), 4.82 (s, 1H), 6.58 (d, 1H), 6.63–6.66 (m, 2H), 6.75 (d, 1H), 7.63 (t, 1H), 7.74 (s, 1H), 8.19–8.26 (m, 2H), 8.60 (d, 1H).

3-[1-(5-Fluoro-2-methoxyphenyl)cycloprop-1-yl]-1-(2-(hydroxymethyl)quinolin-5-ylamino)-2-(trifluoromethyl)propan-2-ol Analogously to Example 40, 200 mg (0.41 mmol) of 5-{3-[1-(5-fluoro-2-methoxyphenyl)cycloprop-1-yl]-2-hydroxy-2-(trifluoromethyl)propylidenamino}-quinoline-2-carboxylic acid methyl ester is reacted with 156 mg (4.1 mmol) of sodium borohydride. After working-up and purification on silica gel with hexane-ethyl acetate (0–75%), 119 mg (63% of theory) of the product is obtained.

$^1$H-NMR (300 MHz, DMSO-d$_6$): δ=0.58–0.61 (m, 1H), 0.78–0.91 (m, 3H), 1.90 (d, 1H), 2.65 (d, 1H), 3.17–3.18 (m, 2H), 3.61 (s, 3H), 4.68 (d, 2H), 5.31 (t, 1H), 5.51 (t, 1H), 5.97 (s, 1H), 6.13 (d, 1H), 6.61 (dd, 1H), 6.85 (td, 1H), 7.01 (dd, 1H), 7.17 (d, 1H), 7.38 (t, 1H), 7.54 (d, 1H), 8.37 (d, 1H).

Example 61

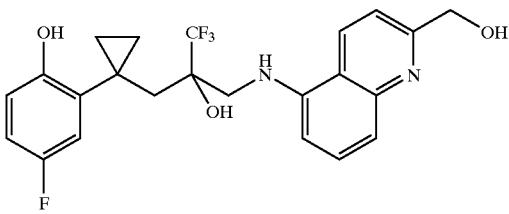

3-[1-(5-Fluoro-2-hydroxyphenyl)cycloprop-1-yl]-1-(2-(hydroxymethyl)quinolin-5-ylamino)-2-(trifluoromethyl)propan-2-ol Analogously to Example 38, 100 mg (0.22 mmol) of 3-[1-(5-fluoro-2-methoxyphenyl)cycloprop-1-yl]-1-(2-(hydroxymethyl)quinolin-5-ylamino)-2-(trifluoromethyl)propan-2-ol is reacted with 4.40 ml (4.40 mmol) of a 1 M boron tribromide solution. After working-up and purification on silica gel with hexane-ethyl acetate (0–100%) as well as with ethyl acetate-methanol (0–20%), 50 mg (50% of theory) of the product is obtained.

$^1$H-NMR (300 MHz, DMSO-d$_6$): δ=0.66–0.73 (m, 1H), 0.83–0.88 (m, 3H), 2.04 (d, 1H), 2.54 (d, 1H), 3.24–3.26 (m, 2H), 4.68 (d, 2H), 5.32 (t, 1H), 5.51 (t, 1H), 5.95 (s, 1H), 6.23 (d, 1H), 6.60 (d, 1H), 6.73–6.79 (m, 1H), 6.94 (dd, 1H), 7.16 (d, 1H), 7.39 (t, 1H), 7.54 (d, 1H), 8.33 (d, 1H), 9.49 (s, 1H).

Example 62

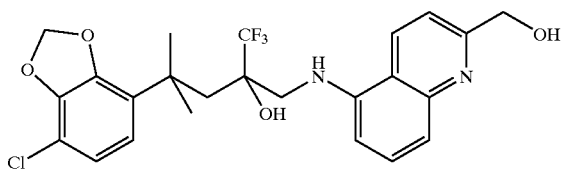

4-(7-Chlorobenzo[1,3]dioxol-4-yl)-2-(2-(hydroxymethyl)quinolin-5-ylamino)-4-methyl-2-(trifluoromethyl)pentan-2-ol 5-[4-(7-Chlorobenzo[1,3]dioxol-4-yl)-2-hydroxy-4-methyl-2-(trifluoromethyl)pentylidenamino]quinoline-2-carboxylic acid methyl ester Analogously to Example 37, 70 mg (0.21 mmol) of 4-(7-chlorobenzo[1,3]dioxol-4-yl)-2-hydroxy-4-methyl-2-(trifluoromethyl)pentanal is reacted with 50 mg (0.25 mmol) of 5-aminoquinoline-2-carboxylic acid methyl ester in 0.5 ml of concentrated acetic acid and 20 ml of toluene. After working-up and purification on silica gel with hexane-ethyl acetate (0–100%), 60 mg (55% of theory) of the product is obtained.

$^1$H-NMR (300 MHz, CDCl$_3$): δ=1.37 (s, 3H), 1.52 (s, 3H), 2.34 (d, 1H), 3.08 (d, 1H), 4.11 (s, 3H), 4.83 (s, 1H), 5.94 (s, 1H), 6.02 (s, 1H), 6.37 (d, 1H), 6.54 (t, 1H), 7.58–7.70 (m, 2H), 8.20–8.26 (m, 2H), 8.57 (d, 1H).

4-(7-Chlorobenzo[1,3]dioxol-4-yl)-2-(2-(hydroxymethyl)quinolin-5-ylamino)-4-methyl-2-(trifluoromethyl)pentan-2-ol Analogously to Example 40, 60 mg (0.11 mmol) of 5-[4-(7-chlorobenzo[1,3]dioxol-4-yl)-2-hydroxy-4-methyl-2-(trifluoromethyl)pentylidenamino]-quinoline-2-carboxylic acid methyl ester is reacted with 18 mg (0.46 mmol) of sodium borohydride. After working-up and purification on silica gel with hexane-ethyl acetate (0–100%) as well as with ethyl acetate-methanol (0–20%), 21 mg (39% of theory) of the product is obtained.

$^1$H-NMR (300 MHz, DMSO-d$_6$): δ=1.37 (s, 3H), 1.53 (s, 3H), 2.11 (d, 1H), 2.55 (d, 1H), 3.01–3.19 (m, 2H), 4.67 (d, 2H), 5.42–5.46 (m, 1H), 5.50 (t, 1H), 5.98–6.08 (m, 4H), 6.86 (s, 2H), 7.18 (d, 1H), 7.36 (t, 1H), 7.55 (d, 1H), 8.32 (d, 1H).

Example 63

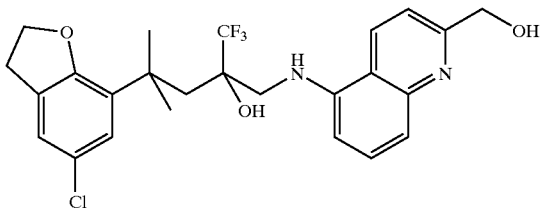

4-(5-Chloro-2,3-dihydrobenzofuran-7-yl)-2-(2-(hydroxymethyl)quinolin-5-ylamino)-4-methyl-2-(trifluoromethyl)pentan-2-ol 5-[4-(5-Chloro-2,3-dihydrobenzofuran-7-yl)-2-hydroxy-4-methyl-2-(trifluoromethyl)pentylidenamino]quinoline-2-carboxylic acid methyl ester Analogously to Example 37, 160 mg (0.47 mmol) of 4-(5-chloro-2,3-dihydrobenzofuran-7-yl)-2-hydroxy-4-methyl-2-(trifluoromethyl)pentanal is reacted with 116 mg (0.57 mmol) of 5-aminoquinoline-2-carboxylic acid methyl ester in 1.0 ml of concentrated acetic acid and 20 ml of toluene. After working-up and purification on silica gel with hexane-ethyl acetate (0–100%), 110 mg (45% of theory) of the product is obtained.

$^1$H-NMR (300 MHz, CDCl$_3$): δ=1.34 (s, 3H), 1.55 (s, 3H), 2.27 (d, 1H), 2.65–2.73 (m, 1H), 2.91–3.01 (m, 1H), 3.35 (d, 1H), 4.11 (s, 3H), 4.42–4.58 (m, 2H), 4.79 (s, 1H), 6.58 (s, 1H), 6.65 (d, 1H), 6.82 (d, 1H), 7.61–7.67 (m, 2H), 8.21 (d, 1H), 8.27 (d, 1H), 8.47 (d, 1H).

4-(5-Chloro-2,3-dihydrobenzofuran-7-yl)-2-(2-(hydroxymethyl)quinolin-5-ylamino)-4-methyl-2-(trifluoromethyl)pentan-2-ol Analogously to Example 40, 110 mg (0.21 mmol) of 5-[4-(5-chloro-2,3-dihydrobenzofuran-7-yl)-2-hydroxy-4-methyl-2-(trifluoromethyl)pentylidenamino]-quinoline-2-carboxylic acid methyl ester is reacted with 32 mg (0.84 mmol) of sodium borohydride. After working-up and purification on silica gel with hexane-ethyl acetate (0–100%) as well as with ethyl acetate-methanol (0–30%), 68 mg (65% of theory) of the product is obtained.

$^1$H-NMR (300 MHz, DMSO-d$_6$): δ=1.34 (s, 3H), 1.53 (s, 3H), 2.03 (d, 1H), 2.77 (d, 1H), 2.85–3.12 (m, 4H), 5.32–5.36 (m, 1H), 5.51 (t, 1H), 5.96 (d, 1H), 6.02 (s, 1H), 7.03 (s, 1H), 7.07 (s, 1H), 7.18 (d, 1H), 7.37 (t, 1H), 7.54 (d, 1H), 8.29 (d, 1H).

Example 64

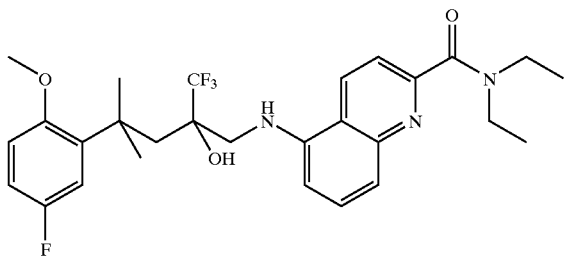

5-[4-(5-Fluoro-2-methoxyphenyl)-2-hydroxy-4-methyl-2-(trifluoromethyl)pentylamino]quinoline-2-carboxylic acid diethylamide 5-Aminoquinoline-2-carboxylic acid diethylamide A suspension that consists of 1.06 g (7.95 mmol) of aluminum chloride in 35 ml of toluene is mixed with 1.70 ml (15.7 mmol) of diethylamine while being cooled with ice. After one hour at room temperature, 350 mg (1.73 mmol) of 5-aminoquinoline-2-carboxylic acid methyl ester is added, and the reaction mixture is allowed to stir for 5 hours at 40° C. The reaction is halted by adding water. It is extracted with dichloromethane, and the combined organic phases are dried on sodium sulfate. After removal of the solvent and purification on silica gel with dichloromethane-methanol (0–10%), 210 mg (50% of theory) of the product is obtained.

$^1$H-NMR (300 MHz, DMSO-d$_6$): δ=1.11 (t, 3H), 1.19 (t, 3H), 3.27 (q, 2H), 3.48 (q, 2H), 6.06 (s, 2H), 6.74 (d, 1H), 7.17 (d, 1H), 7.42–7.47 (m, 2H), 8.61 (d, 1H).

5-[4-(5-Fluoro-2-methoxyphenyl)-2-hydroxy-4-methyl-2-(trifluoromethyl)pentylidenamino]quinoline-2-carboxylic acid diethylamide A solution that consists of 210 mg (0.86 mmol) of 5-aminoquinoline-2-carboxylic acid diethylamide, 266 mg (0.86 mmol) of 4-(5-fluoro-2-methoxyphenyl)-2-hydroxy-4-methyl-2-(trifluoromethyl)pentanal and 0.36 ml (1.73 mmol) of titanium tetraethylate in 15 ml of tetrahydrofuran is stirred for one hour at room temperature and then for 3 hours at 80° C. After removal of the solvent and purification on silica gel with hexane-ethyl acetate (0–70%), 230 mg (52% of theory) of the product is obtained.

$^1$H-NMR (300 MHz, CDCl$_3$): δ=1.23 (t, 3H), 1.33 (t, 3H), 1.37 (s, 3H), 1.57 (s, 3H), 3.38–3.50 (m, 3H), 3.63 (q, 2H), 3.81 (s, 3H), 4.82 (s, 1H), 6.43–6.50 (m, 2H), 6.56 (dd, 1H), 6.79 (dd, 1H), 7.50 (s, 1H), 7.55 (t, 1H), 7.68 (d, 1H), 7.99 (d, 1H), 8.39 (d, 1H).

5-[4-(5-Fluoro-2-methoxyphenyl)-2-hydroxy-4-methyl-2-(trifluoromethyl)pentylamino]quinoline-2-carboxylic acid diethylamide A solution that consists of 230 mg (0.45 mmol) of 5-[4-(5-fluoro-2-methoxyphenyl)-2-hydroxy-4-methyl-2-(trifluoromethyl)pentylidenamino]quinoline-2-carboxylic acid diethylamide and 0.132 ml (0.58 mmol) of titanium tetraethylate in 14 ml of ethanol is mixed with 135 mg (3.55 mmol) of sodium borohydride. After 6 hours at room temperature, the reaction is halted by adding saturated sodium chloride solution and ethyl acetate. The precipitate that is produced is suctioned off on Celite. The filtrate is washed with saturated sodium chloride solution, and it is dried on sodium sulfate. After removal of the solvent and purification on silica gel with hexane-ethyl acetate (0–70%), 220 mg (92%) of the product is obtained.

$^1$H-NMR (300 MHz, CDCl$_3$): δ=1.20 (t, 3H), 1.31 (t, 3H), 1.46 (s, 3H), 1.56 (s, 3H), 2.34 (d, 1H), 2.78 (d, 1H), 3.13 (dd, 1H), 3.19 (s, 1H), 3.31 (dd, 1H), 3.41 (q, 2H), 3.60 (q, 2H), 3.84 (s, 3H), 4.33–4.37 (m, 1H), 6.08 (d, 1H), 6.79 (dd, 1H), 6.89–6.96 (m, 1H), 7.11 (dd, 1H), 7.42–7.51 (m, 2H), 7.55 (d, 1H), 8.03 (d, 1H).

Example 65

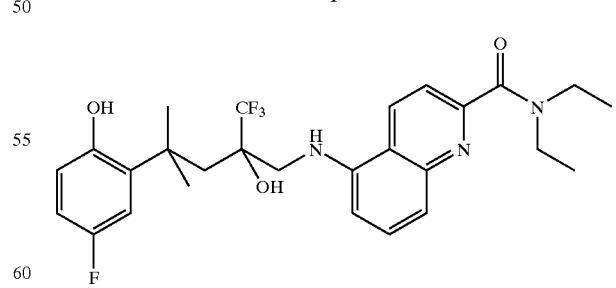

5-[4-(5-Fluoro-2-hydroxyphenyl)-2-hydroxy-4-methyl-2-(trifluoromethyl)pentylamino]-quinoline-2-carboxylic acid diethylamide 210 mg (0.39 mmol) of 5-[4-(5-fluoro-2-methoxyphenyl)-2-hydroxy-4-methyl-2-(trifluoromethyl)

pentylamino]quinoline-2-carboxylic acid diethylamide is mixed with 7.8 ml (7.8 mmol) of a 1 M boron tribromide solution in dichloromethane. After 20 hours at room temperature, the reaction is halted by adding water. It is extracted with ethyl acetate, the combined organic phases are washed with saturated sodium bicarbonate solution, and it is dried on sodium sulfate. After the solvent is removed and after purification on silica gel with hexane-ethyl acetate (0–100%), 56 mg (28%) of the product is obtained.

$^1$H-NMR (300 MHz, DMSO-$d_6$): δ=1.10 (t, 3H), 1.19 (t, 3H), 1.40 (s, 3H), 1.57 (s, 3H), 1.93 (d, 1H), 2.96 (dd, 1H), 3.11–3.29 (m, 4H), 3.48 (q, 2H), 5.48–5.52 (m, 1H), 5.97 (s, 1H), 6.01 (d, 1H), 6.70 (dd, 1H), 6.79–6.85 (m, 1H), 7.00 (dd, 1H), 7.22 (d, 1H), 7.41 (t, 1H), 7.51 (d, 1H), 8.40 (d, 1H), 9.73 (s, 1H).

Example 66

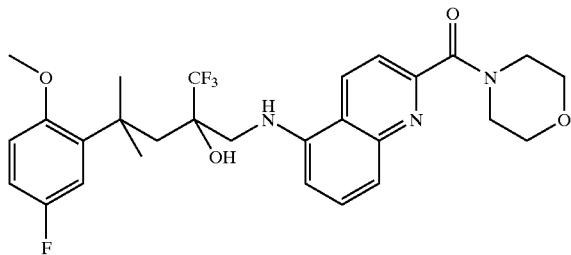

4-(5-Fluoro-2-methoxyphenyl)-1-(2-(morpholin-4-ylmethyl)quinolin-5-ylamino)-4-methyl-2-(trifluoromethyl)pentan-2-ol 2-Bromomethyl-5-nitroquinoline A solution that consists of 800 mg (4.25 mmol) of 5-nitro-2-methylquinoline in 20 ml of tetrachloromethane is mixed with 11 mg (0.04 mmol) of benzoyl peroxide and 794 mg (4.46 mmol) of N-bromosuccinimide. The reaction mixture is allowed to reflux for 8 hours in the presence of UV light. Insoluble components are filtered off, and the filtrate is concentrated by evaporation. After purification on silica gel with hexane-ethyl acetate (0–100%), 320 mg (28% of theory) of the product is obtained.

$^1$H-NMR (300 MHz, CDCl$_3$): δ=4.72 (s, 2H), 7.79–7.82 (m, 2H), 8.35–8.39 (m, 2H), 9.02 (d, 1H).

2-(Morpholin-4-ylmethyl)-5-nitroquinoline 460 mg (1.72 mmol) of 2-bromomethyl-5-nitroquinoline and 0.54 ml (6.2 mmol) of morpholine are dissolved in 150 ml of toluene. After 1.07 g (7.74 mmol) of potassium carbonate is added, the reaction mixture is allowed to reflux for 2 hours. Potassium carbonate is filtered off, and the filtrate is concentrated by evaporation. After purification on silica gel with hexane-ethyl acetate (0–100%), 190 mg (40% of theory) of the product is obtained.

$^1$H-NMR (300 MHz, CDCl$_3$): δ=2.55–2.58 (m, 4H), 3.74–3.77 (m, 4H), 3.86 (s, 2H), 7.78 (t, 1H), 7.87 (d, 1H), 8.33–8.39 (m, 2H), 8.95 (d, 1H).

5-Amino-2-(morpholin-4-ylmethyl)quinoline 190 mg (0.7 mmol) of 2-(morpholin-4-ylmethyl)-5-nitroquinoline is dissolved in 10 ml of methanol. After the addition of 19 mg of palladium on carbon and 19 mg of potassium carbonate, the reaction mixture is allowed to stir for 4 hours at room temperature under hydrogen atmosphere. It is then filtered on Celite and washed with ethyl acetate. After removal of the solvent in a vacuum and chromatography on silica gel with hexane-ethyl acetate (0–100%) as well as with ethyl acetate-methanol (0–100%), 134 mg (79% of theory) of the product is obtained.

$^1$H-NMR (300 MHz, CDCl$_3$): δ=2.55–2.57 (m, 4H), 3.73–3.76 (m, 4H), 3.82 (s, 2H), 4.18 (br, 2H), 6.79 (d, 1H), 7.45–7.59 (m, 3H), 8.14 (d, 1H).

4-(5-Fluoro-2-methoxyphenyl)-1-(2-(morpholin-4-ylmethyl)quinolin-5-ylimino)-4-methyl-2-(trifluoromethyl)pentan-2-ol Analogously to Example 37, 180 mg (0.74 mmol) of 5-amino-2-(morpholin-4-ylmethyl)quinoline is reacted with 274 mg (0.89 mmol) of 4-(5-fluoro-2-methoxyphenyl)-2-hydroxy-4-methyl-2-(trifluoromethyl)pentanal in 0.8 ml of concentrated acetic acid and 20 ml of toluene. After purification on silica gel with hexane-ethyl acetate (0–100%), 220 mg (56% of theory) of the product is obtained.

$^1$H-NMR (300 MHz, CDCl$_3$): δ=1.37 (s, 3H), 1.57 (s, 3H), 2.29 (d, 1H), 2.55–2.58 (m, 4H), 3.46 (d, 1H), 3.75–3.77 (m, 4H), 3.80 (s, 3H), 3.85 (s, 2H), 4.88 (s, 1H), 6.38–6.45 (m, 2H), 6.53 (dd, 1H), 6.79 (dd, 1H), 7.47–7.52 (m, 2H), 7.67 (d, 1H), 7.94 (d, 1H), 8.28 (d, 1H).

4-(5-Fluoro-2-methoxyphenyl)-1-(2-(morpholin-4-ylmethyl)quinolin-5-ylamino)-4-methyl-2-(trifluoromethyl)pentan-2-ol Analogously to Example 40, 220 mg (0.41 mmol) of 4-(5-fluoro-2-methoxyphenyl)-1-(2-(morpholin-4-ylmethyl)quinolin-5-ylamino)-4-methyl-2-(trifluoromethyl)pentan-2-ol is dissolved in 10 ml of methanol and mixed with 315 mg (8.25 mmol) of sodium borohydride. After working-up and purification, 109 mg (50% of theory) of the product is obtained.

$^1$H-NMR (300 MHz, CDCl$_3$): δ=1.46 (s, 3H), 1.56 (s, 3H), 2.34 (d, 1H), 2.52–2.55 (m, 4H), 2.77 (d, 1H), 3.09–3.16 (m, 2H), 3.31 (dd, 1H), 3.72–3.75 (m, 4H), 3.81 (s, 2H), 3.85 (s, 3H), 4.26–4.29 (m, 1H), 6.05 (d, 1H), 6.81 (dd, 1H), 6.91–6.98 (m, 1H), 7.11 (dd, 1H), 7.39–7.56 (m, 3H), 7.94 (d, 1H).

Example 67

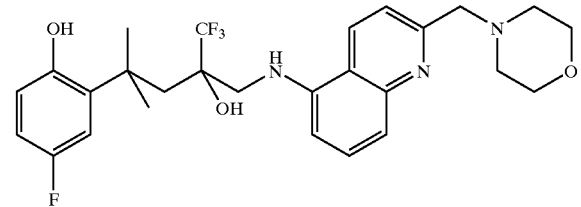

4-(5-Fluoro-2-hydroxyphenyl)-1-(2-(morpholin-4-ylmethyl)quinolin-5-ylamino)-4-methyl-2-(trifluoromethyl)pentan-2-ol Analogously to Example 38, 80 mg (0.15 mmol) of 4-(5-fluoro-2-methoxyphenyl)-1-(2-(morpholin-4-ylmethyl)quinolin-5-ylamino)-4-methyl-2-trifluoromethyl)pentan-2-ol is mixed with 3.0 ml (3.0 mmol) of a 1 M boron tribromide solution in dichloromethane. After working-up and purification on silica gel with hexane-ethyl acetate (0–100%) as well as ethyl acetate-methanol (0–20%), 53 mg (68% of theory) of the product is obtained.

$^1$H-NMR (300 MHz, DMSO-$d_6$): δ=1.40 (s, 3H), 1.56 (s, 3H), 2.40–2.43 (m, 4H), 2.93 (dd, 1H), 3.09–3.20 (m, 2H), 3.58–3.61 (m, 4H), 3.69 (s, 2H), 5.33–5.37 (m, 1H), 5.93 (d, 1H), 5.96 (br, 1H), 6.72 (dd, 1H), 6.80–6.86 (m, 1H), 6.99 (dd, 1H), 7.17 (d, 1H), 7.32 (t, 1H), 7.51 (d, 1H), 8.24 (d, 1H), 9.74 (br, 1H).

Example 68

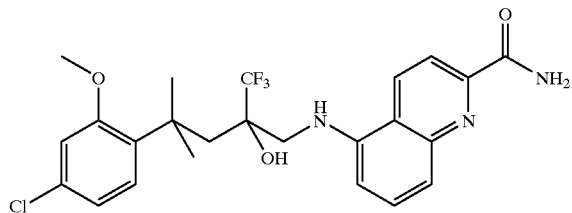

5-[4-(4-Chloro-2-methoxyphenyl)-2-hydroxy-4-methyl-2-(trifluoromethyl)pentylamino]-quinoline-2-carboxylic acid amide 5-[4-(4-Chloro-2-methoxyphenyl)-2-hydroxy-4-methyl-2-(trifluoromethyl)pentylidenamino]-quinoline-2-carboxylic acid amide Analogously to Example 37, 160 mg (0.87 mmol) of 5-aminoquinoline-2-carboxylic acid amide is reacted with 341 mg (1.05 mmol) of 4-(4-chloro-2-methoxyphenyl)-2-hydroxy-4-methyl-2-(trifluoromethyl)pentanal in 0.96 ml of concentrated acetic acid and 20 ml of toluene. After purification on silica gel with hexane-ethyl acetate (0–100%), 340 mg (79% of theory) of the product is obtained.

$^1$H-NMR (300 MHz, CDCl$_3$): δ=1.37 (s, 3H), 1.58 (s, 3H), 2.27 (d, 1H), 3.44 (d, 1H), 3.84 (s, 3H), 4.80 (s, 1H), 5.71 (br, 1H), 6.39 (d, 1H), 6.44 (dd, 1H), 6.66 (d, 1H), 6.99 (d, 1H), 7.51 (s, 1H), 7.62 (dd, 1H), 7.99 (d, 1H), 8.07 (br, 1H), 8.33 (d, 1H), 8.49 (d, 1H).

5-[4-(4-Chloro-2-methoxyphenyl)-2-hydroxy-4-methyl-2-(trifluoromethyl)pentylamino]-quinoline-2-carboxylic acid amide Analogously to Example 40, 340 mg (0.69 mmol) of 5-[4-(4-chloro-2-methoxyphenyl)-2-hydroxy-4-methyl-2-(trifluoromethyl)pentylidenamino]quinoline-2-carboxylic acid amide is dissolved in 10 ml of methanol and mixed several times with 110 mg (2.89 mmol) of sodium borohydride. After working-up and purification on silica gel with hexane-ethyl acetate (0–100%), 280 mg (82% of theory) of the product is obtained.

$^1$H-NMR (300 MHz, DMSO-d$_6$): δ=1.37 (s, 3H), 1.56 (s, 3H), 2.06 (d, 1H), 2.85–3.06 (m, 3H), 3.81 (s, 3H), 5.57–5.61 (m, 1H), 5.96 (s, 1H), 6.00 (d, 1H), 6.95 (dd, 1H), 6.98 (d, 1H), 7.29–7.35 (m, 2H), 7.46 (t, 1H), 7.71 (br, 1H), 8.04 (d, 1H), 8.21 (br, 1H), 8.48 (d, 1H).

Example 69

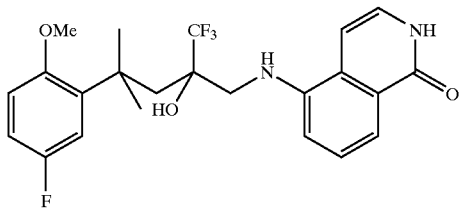

5-{[4-(5-Fluoro-2-methoxyphenyl)-2-hydroxy-4-methyl-2-(trifluoromethyl)pentyl]amino}isoquinolin-1(2H)-one a. 2-Methyl-3-nitrobenzoic acid methyl ester 20 g (110.4 mmol) of 2-methyl-3-nitrobenzoic acid is refluxed in 100 ml of methanol for 10 hours after 2 ml of concentrated sulfuric acid is added. The product that crystallizes out during cooling is suctioned off and dried. The filtrate is evaporated to the dry state, the solid residue is taken up in ethyl acetate, and the solution is washed twice with saturated sodium bicarbonate solution. After drying on Na$_2$SO$_4$, another product is obtained. Together, 16.4 g (76.3%) of the desired compound is obtained.

b. 5-Nitroisocoumarin 16.4 g (84.03 mmol) of the compound that is described under a is stirred with 26.8 g (225.1 mmol) of N,N-dimethylformamide dimethylacetal in 85 ml of dimethylformamide for 12 hours at 130° C. The solvent is drawn off in a rotary evaporator, the residue is taken up in methyl-tert-butyl ether and washed three times with water. After washing with saturated NaCl solution, the organic phase is dried. After the desiccant is filtered off and the solvent is spun off, the remaining residue is chromatographed on silica gel (mobile solvent ethyl acetate/hexane). 8.73 g (54.5%) of the desired compound is isolated.

MS (CI) m/e (relative intensity): 209 (M$^{+18}$, 52), 191 (M$^+$, 29), 179 (100).

c. 5-Nitroisoquinolin-1(2H)-one 2.51 g (13.13 mmol) of 5-nitroisocoumarin is added to 100 ml of ethanol. Ammonia is pressure-forced in in an autoclave. The product precipitates and is suctioned off. 1.98 g (79.7%) of the desired compound is isolated.

MS (CI) m/e (relative intensity): 208 (M$^{+18}$, 60), 191 (M$^{+1}$, 100), 161 (81).

d. 5-Aminoisoquinolin-1(2H)-one 268.3 mg (1.51 mmol) of 5-nitroisoquinolin-1(2H)-one is added with 376.5 mg of ammonium chloride and 2.6 ml of water in 14 ml of ethanol and 5.4 ml of tetrahydrofuran. After the addition of 1.23 g of zinc powder in portions (heating to 30 to 35° C.), it is stirred for two hours. The reaction mixture is suctioned off via a glass fiber filter and rewashed with ethyl acetate. After the filtrate is washed with water and saturated sodium chloride solution, the organic phase is dried as usual. Filtering off the desiccant and spinning-off the solvent produce 196.5 mg (88.1%) of the desired amine.

MS (CI) m/e (relative intensity): 161 (M$^{+1}$, 100).

e. 5-{(E/Z)-[4-(5-Fluoro-2-methoxyphenyl)-2-hydroxy-4-methyl-2-(trifluoromethyl) pentylidene]amino}isoquinolin-1(2H)-one 140.1 mg (0.455 mmol) of 4-(5-fluoro-2-methoxyphenyl)-2-hydroxy-4-methyl-2-(trifluoromethyl) pentanal is stirred with 72.8 mg (0.455 mmol) of 5-aminoisoquinolin-1(2H)-one in 0.74 ml of glacial acetic acid overnight. The mixture is evaporated to the dry state, and the residue is put on a Flashmaster column (mobile solvent ethyl acetate/hexane). 103.6 mg (52.5%) of the desired compound is isolated.

MS (ES+) m/e (relative intensity): 451 (M$^{+1}$, 100).

f. 5-{[4-(5-Fluoro-2-methoxyphenyl)-2-hydroxy-4-methyl-2-(trifluoromethyl)pentyl]amino}isoquinolin-1(2H)-one 103.6 mg (0.239 mmol) of the compound that is described under e. is mixed with 2.6 ml of dichloroethane and 0.1 ml of glacial acetic acid. After 75.9 mg (0.359 mmol) of sodium triacetoxy borohydride is added, it is stirred overnight. The reaction mixture is mixed with saturated sodium bicarbonate solution and extracted twice with ethyl acetate. The combined organic phases are washed with water and saturated sodium chloride solution, dried, filtered and concentrated by evaporation. After chromatography on a Flashmaster (mobile solvent ethyl acetate/hexane), 36 mg (34.6%) of the desired compound is isolated.

MS (ES+) m/e (relative intensity): 453 (M$^{+1}$, 100).

Example 70

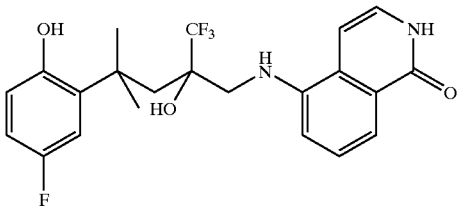

5-{[4-(5-Fluoro-2-hydroxyphenyl)-2-hydroxy-4-methyl-2-(trifluoromethyl)-pentyl]amino}isoquinolin-1(2H)-one 30 mg (0.066 mmol) of the compound that is synthesized under Example 70 f. is mixed with 0.76 ml of a 1 M solution of boron tribromide in dichloromethane. After four hours of stirring at room temperature, the reaction mixture is diluted with ethyl acetate and washed once with saturated sodium bicarbonate solution. After the organic phase (sodium sulfate) is dried, the solvent is spun off after the desiccant is filtered off. Chromatography on a Flashmaster (mobile solvent ethyl acetate/hexane) yields 15.9 mg (56.7%) of the desired compound.

MS (ES+) m/e (relative intensity): 439 ($M^{+1}$, 100).

Similarly produced starting from the corresponding aldehydes were:
5-{[4-(3-Fluoro-2-hydroxyphenyl)-2-hydroxy-4-methyl-2-(trifluoromethyl) pentyl]amino}isoquinolin-1(2H)-one
5-({3-[1-(3-Fluoro-2-hydroxyphenyl)cyclopropyl]-2-hydroxy-2-(trifluoromethyl)propyl}amino)isoquinolin-1(2H)-one
5-{[4-(4-Chloro-2-hydroxyphenyl)-2-hydroxy-4-methyl-2-(trifluoromethyl) pentyl]amino}isoquinolin-1(2H)-one
5-{[4-(5-Chloro-2-hydroxyphenyl)-2-hydroxy-4-methyl-2-(trifluoromethyl) pentyl]amino}isoquinolin-1(2H)-one
5-{[4-(2-Chlorophenyl)-2-hydroxy-4-methyl-2-(trifluoromethyl) pentyl]amino}isoquinolin-1(2H)-one
(+)-5-{[4-(5-Fluoro-2-hydroxyphenyl)-2-hydroxy-4-methyl-2-(trifluoromethyl) pentyl]amino}isoquinolin-1(2H)-one
(−)-5-{[4-(5-Fluoro-2-hydroxyphenyl)-2-hydroxy-4-methyl-2-(trifluoromethyl) pentyl]amino}isoquinolin-1(2H)-one

Example 71

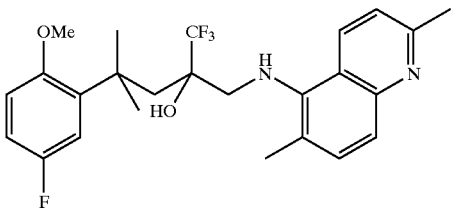

5-{[4-(5-Fluoro-2-methoxyphenyl)-2-hydroxy-4-methyl-2-(trifluoromethyl)pentyl]amino}-2,6-dimethyl-quinoline a. 2,6-Dimethyl-5-nitroquinoline 3 g (19.08 mmol) of 2,6-dimethylquinoline is introduced into 15 ml of concentrated sulfuric acid at 10° C. After one-half hour, a solution of 2.03 g of potassium nitrate in 11.4 concentrated sulfuric acid is added in drops, specifically so that the temperature remains between 5° and 15° C. The batch is stirred for one more hour and then poured onto ice water. It is made ammonia-alkaline, and the deposited precipitate is suctioned off. After washing with water, the crude product is dissolved in ethyl acetate and shaken from water. The organic phase is treated as usual. After the solvent is spun off, 3.69 g (95.6%) of the desired compound remains, which is used in the reduction without further purification.

MS (CI) m/e (relative intensity): 220 ($M^{+18}$, 20), 203 ($M^{+1}$, 100).

b. 5-Amino-2,6-dimethylquinoline 3.69 g (18.248 mmol) of the compound that is produced according to a. is stirred with 15.19 g (66.85 mmol) of tin(II) chloride dihydrate and 30.4 ml of concentrated hydrochloric acid for 45 minutes at 85° C. The batch is poured onto ice water, made basic with 2N NaOH, and the amine is extracted with ethyl acetate. The organic extracts are washed with brine, dried on sodium sulfate, and the solvent is spun off after the desiccant is suctioned off. The remaining residue is chromatographed on silica gel (mobile solvent ethyl acetate/hexane). 2.75 g (87.6%) of the desired compound is isolated.

MS (ES+) m/e (relative intensity): 173 ($M^{+1}$, 100).

c. 5-{(E/Z)-[4-(5-Fluoro-2-methoxyphenyl)-2-hydroxy-4-methyl-2-(trifluoromethyl) pentylidene]amino}2,6-dimethylquinoline 250 mg (0.811 mmol) of 4-(5-fluoro-2-methoxyphenyl)-2-hydroxy-4-methyl-2-trifluoromethyl)-pentanal is refluxed with 139.7 mg (0.811 mmol) of 5-amino, 2,6-dimethylquinoline in ten milliliters of dichloroethane with the addition of 0.2 ml of trifluoroacetic acid and 150 mg of molecular sieve (4 A) for seven days. The mixture is filtered on a glass fiber filter, and the filtrate is evaporated to the dry state. The residue is put on a Flashmaster column (mobile solvent ethyl acetate/hexane). 134.3 mg (35.8%) of the desired compound is isolated.

MS (ES+) m/e (relative intensity): 463 ($M^{+1}$, 100).

d. 5-{[4-(5-Fluoro-2-methoxyphenyl)-2-hydroxy-4-methyl-2-(trifluoromethyl) pentyl]amino}2,6-dimethylquinoline 134.3 mg (0.29 mmol) of the compound that is described under c. is added to 17 ml of methanol and mixed with 1.7 ml of glacial acetic acid. After 141.5 mg (2.252 mmol) of sodium cyanoborohydride is added, it is stirred for four hours. The reaction mixture is mixed with saturated sodium bicarbonate solution and extracted twice with ethyl acetate. The combined organic phases are washed with water and saturated sodium chloride solution, dried, filtered, and concentrated by evaporation. After chromatography on a Flashmaster (mobile solvent ethyl acetate/hexane), 80 mg (59.3%) of the desired compound is isolated.

MS (ES+) m/e (relative intensity): 465 ($M^{+1}$, 100).

Example 72

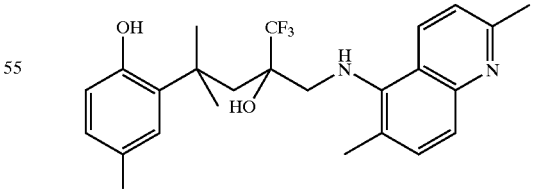

5-{[4-(5-Fluoro-2-hydroxyphenyl)-2-hydroxy-4-methyl-2-(trifluoromethyl)pentyl]amino}-2,6-dimethyl-quinoline 80 mg (0.172 mmol) of the compound that is synthesized under Example 71d. is mixed with two milliliters of a 1 M solution of boron tribromide in dichloromethane. After five hours of stirring at room temperature, the reaction mixture is diluted with ethyl acetate and washed once with saturated sodium bicarbonate solution. The organic phase is dried (sodium sulfate), and the solvent is spun off after the desiccant is filtered off. Chromatography on a Flashmaster (mobile solvent ethyl acetate/hexane) yields 58.9 mg (75.9%) of the desired compound.

MS (ES+) m/e (relative intensity): 451 ($M^{+1}$, 100).

Similarly synthesized starting from the corresponding aldehydes and amines were the following compounds:

(+)-5-{[4-(5-Fluoro-2-hydroxyphenyl)-2-hydroxy-4-methyl-2-(trifluoromethyl) pentyl]amino}-2,6-dimethylquinoline (−)-5-{[4-(5-Fluoro-2-hydroxyphenyl)-2-hydroxy-4-methyl-2-(trifluoromethyl) pentyl]amino}-2,6-dimethylquinoline 5-{[4-(3-Fluoro-2-hydroxyphenyl)-2-hydroxy-4-methyl-2-(trifluoromethyl) pentyl]amino}-2,6-dimethylquinoline 5-{[4-(5-Fluoro-2-hydroxyphenyl)-2-hydroxy-4-methyl-2-(trifluoromethyl) pentyl]amino}-6-chloro-2-methylquinoline 5-{[4-(3-Fluoro-2-hydroxyphenyl)-2-hydroxy-4-methyl-2-(trifluoromethyl) pentyl]amino}6-chloro-2-methylquinoline

Example 73

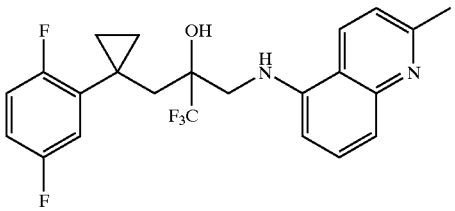

3-[1-(2,5-Difluorophenyl)-cycloprop-1-yl]-1-(2-methylquinolin-5-ylamino)-2-(trifluoromethyl)-1-(2-methylquinolin-5-ylamino)-propan-2-ol Analogously to Example 76, 60 mg (1.46 mmol) of NaH (60%) and 244 mg (1.23 mmol) of 5-acetylamino-2-methylquinoline are reacted with 365 mg (0.81 mmol) of toluene-4-sulfonic acid-3-[1-(2,5-difluorophenyl)-cycloprop-1-yl]-2-(trifluoromethyl)-2-hydroxy-propyl ester. The crude product is treated analogously to Example 76 with 1 M sodium hydroxide solution. After chromatography on silica gel with hexane-ethyl acetate (30–50%), 67 mg of product is obtained.

H-NMR (CDCl$_3$); δ=0.80–1.02 (m, 4H), 2.16 (d, 1H), 2.42 (d, 1H), 2.21 (s, 3H), 3.27–3.42 (m, 2H), 4.21–4.30 (m, 1H), 6.30 (dd, 1H), 6.66–6.81 (m, 2H), 6.95–7.05 (m, 1H), 7.22 (d, 1H), 7.40–7.50 (m, 2H), 7.96 (d, 1H).

MS (ESI): 437 (M+H).

Example 74

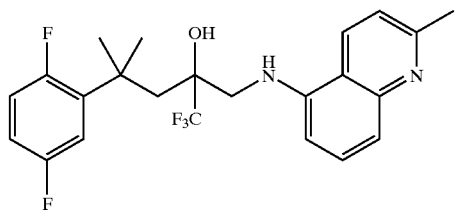

4-(2,5-Difluorophenyl)-4-methyl-1-(2-methylquinolin-5-ylamino)-2-(trifluoromethyl-pentan-2-ol 175 mg (0.62 mmol) of 4-(2,5-difluorophenyl)-4-methyl-2-(trifluoromethyl)-pentanal and 125 mg (0.78 mmol) of 5-amino-2-methylquinoline are stirred in 10 ml of toluene and 3 ml of acetic acid for 18 hours at room temperature and refluxed for another 2 hours in a water separator. The crude product is reduced analogously to 79 with 120 mg (3.16 mmol) of NaBH$_4$ in 5 ml of acetic acid. After chromatography on silica gel with hexane-ethyl acetate (30%), 45 mg of product is obtained.

MS (EI): 438 ($M^+$).

Example 75

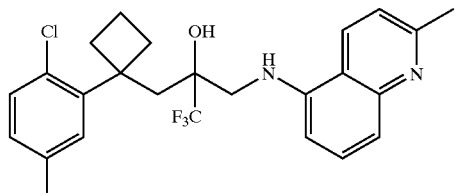

3-[1-(2-Chloro-5-fluorophenyl)cyclobut-1-yl]-1-(2-methylquinolin-5-ylamino)-2-(trifluoromethyl)-propan-2-ol Analogously to Example 79, 200 mg (0.64 mmol) of 3-[1-(2-chloro-5-fluorophenyl)cyclobut-1-yl]-2-(trifluoromethyl)-propanal and 126 mg (0.80 mmol) of 5-amino-2-methylquinoline are reacted, and the isolated crude product is reduced with 102 mg (2.70 mmol) of NaBH$_4$. After chromatography on silica gel with hexane-ethyl acetate, 165 mg of product is obtained.

MS (ESI): 467 (M+H); angle of rotation of the pure (−)-enantiomer after separation by chiral HPLC: α$_D$=−31.4.

OTHER EXAMPLES
Synthesis of the Diol Precursors:

Diol-Example a 4-(7-Bromo-1,3-benzodioxol-4-yl)-2-hydroxy-4-methyl-2-(trifluoromethyl)pentan-1-ol 2,3-Dihydroxy-4-nitrobenzaldehyde:

17.2 g of 2-hydroxy-3-methoxy-4-nitrobenzaldehyde (J. Het. Chem. 33, (1996), 1171) in 350 ml of dichloromethane is slowly mixed at 0° C. with 175 ml of boron tribromide solution (1 M in dichloromethane), and it is stirred for another 4 hours. The batch is added to ice water, the organic phase is separated, and the aqueous phase is extracted with dichloromethane. The combined organic phases are washed with water, and the solvent is removed in a vacuum. 15.2 g of 2,3-dihydroxy-4-nitrobenzaldehyde is obtained as a red solid, flash point 122–126° C.

7-Nitro-benzo[1,3]dioxole-4-carboxylic acid:

14.2 g of 2,3-dihydroxy-4-nitrobenzaldehyde in 1000 ml of DMF is stirred with 57.6 ml of bromochloromethane and 50.6 g of cesium carbonate at 100° C. for 7 hours. The batch is added to 1 N hydrochloric acid and extracted with ethyl acetate. The organic phase is washed several times with water and brine, dried with sodium sulfate and concentrated by evaporation in a vacuum. The brown solid that is obtained is purified by column chromatography (silica gel, hexane/ethyl acetate 100:0→60:40). 7.4 g of 7-nitro-benzo[1,3]dioxole-4-carbaldehyde is obtained as a light yellow solid. The latter is mixed in 400 ml of acetone at 10° C. with a solution of 11.8 g of potassium permanganate in 190 ml of acetone/water (1:1). It was stirred for 10 hours, added to 2 N hydrochloric acid and filtered through diatomaceous earth. The acetone is removed in a vacuum, and the aqueous phase is made alkaline with sodium hydroxide solution. It is extracted with ether, and then the aqueous phase is acidified with hydrochloric acid. It is extracted with ethyl acetate, washed with water, dried with sodium sulfate and concentrated by evaporation in a vacuum. 4.36 g of 7-nitro-benzo[1,3]dioxole-4-carboxylic acid is obtained as a brown solid, flash point 230–239° C.

7-Amino-benzo[1,3]dioxole-4-carboxylic acid:

8.05 g of 7-nitro-benzo[1,3]dioxole-4-carboxylic acid is reacted with hydrogen in 650 ml of ethanol with 800 mg of palladium/carbon catalyst under normal pressure at room temperature. It is filtered through diatomaceous earth and concentrated by evaporation in a vacuum. 6.82 g of 7-amino-benzo[1,3]dioxole-4-carboxylic acid is obtained as a brown solid, flash point 196–197° C.

2-(7-Bromo-1,3-benzodioxol-4-yl)-propan-2-ol:

1.95 g of 7-amino-benzo[1,3]dioxole-4-carboxylic acid in 25 ml of hydrobromic acid (48%) and 20 ml of water are mixed at 0° C. with a solution of 760 mg of sodium nitrite in 4.2 ml of water. It is stirred for 15 minutes and then added to a solution of 2.07 g of copper(I) bromide in 5.5 ml of hydrobromic acid (48%). It is heated for 30 minutes to 100° C., added to water and extracted with ethyl acetate. It is washed with brine, dried with sodium sulfate and concentrated by evaporation in a vacuum. 2.88 g of 7-bromo-benzo[1,3]dioxole-4-carboxylic acid is obtained as a brown solid. The latter is reacted in 50 ml of DMF at 0° C. with 4.08 g of cesium carbonate and 0.8 ml of methyl iodide. It is stirred for 4 hours at room temperature, added to water, and extracted with ethyl acetate. It is washed several times with water and brine, dried and concentrated by evaporation in a vacuum. 1.81 g of 7-bromo-benzo[1,3]dioxole-4-carboxylic acid methyl ester is obtained as a red solid. The latter is dissolved in 5 ml of ether, and 10 ml of THF is added to a solution of 5.06 ml of methylmagnesium chloride (3 M in THF) and 6 ml of ether at room temperature. After 3.5 hours, the batch is added to 1N hydrochloric acid, extracted with ethyl acetate, washed with brine, dried and concentrated by evaporation in a vacuum. 1.79 g of 2-(7-bromo-1,3-benzodioxol-4-yl)-propan-2-ol is obtained as an orange-colored oil.

$^1$H-NMR (CDCl$_3$), δ (ppm)=1.58 (s, 6H), 6.05 (s, 2H), 6.85 (d, 1H), 6.97 (d, 1H).

4-(7-Bromobenzo[1,3]dioxol-4-yl)-4-methyl-2-oxo-valeric acid:

1.77 g of 2-(7-bromobenzo[1,3]dioxol-4-yl)-propan-2-ol and 2.82 g of 2-trimethylsilyloxy-acrylic acid-ethyl ester (WO 00/32584) in 36 ml of dichloromethane are mixed at −70° C. with 1.10 ml of tin(VI)chloride. It is stirred for 20 minutes at −70° C. and then added to saturated sodium carbonate solution. It is extracted with dichloromethane, washed with water, dried and concentrated by evaporation in a vacuum. 3.15 g of 4-(7-bromo-1,3-benzodioxol-4-yl)-4-methyl-2-oxo-valeric acid-ethyl ester is obtained as a crude product. The latter is reacted for 4 hours at room temperature in 57 ml of a mixture that consists of 1N sodium hydroxide solution in ethanol/water. The batch is added to water, extracted with ether and then the aqueous phase is acidified with hydrochloric acid. It is extracted with ethyl acetate, washed with water, dried with sodium sulfate and concentrated by evaporation in a vacuum. 2.1 g of 4-(7-bromo-1,3-benzodioxol-4-yl)-4-methyl-2-oxo-valeric acid is obtained as a yellow oil.

$^1$H-NMR (CDCl$_3$), δ (ppm)=1.46 (s, 6H), 3.44 (s, 2H), 5.98 (s, 2H), 6.66 (d, 1H), 6.94 (d, 1H).

4-(7-Bromo-1,3-benzodioxol-4-yl)-2-hydroxy-4-methyl-2-trifluoromethyl-ventan-1-ol:

300 mg of 4-(7-bromo-1,3-benzodioxol-4-yl)-4-methyl-2-oxo-valeric acid and 0.1 ml of sulfuric acid (96%) in 5 ml of ethanol are heated for 4 hours to 70° C. Then, the batch is concentrated by evaporation in a vacuum and added to water. It is extracted with ethyl acetate, washed with brine, dried and concentrated by evaporation in a vacuum. 272 mg of 4-(7-bromo-1,3-benzodioxol-4-yl)-4-methyl-2-oxo-valeric acid-ethyl ester is obtained as a yellow oil. This ester and 0.32 ml of trifluoromethyl-trimethylsilane in 4 ml of THF are mixed with 0.14 ml of a tetrabutylammonium fluoride solution (1 M in THF) at −70° C. It is stirred for 1 hour at 70° C, for 1.5 hours at −10° C., for 1 hour at 0° C. and for 2 hours at room temperature. Another spatula-tip full of tetrabutylammonium fluoride is added, and after stirring is continued for 20 minutes, it is added to water. It is extracted with ethyl acetate, washed with water, dried with sodium sulfate and concentrated by evaporation in a vacuum. 297 mg of 4-(7-bromo-1,3-benzodioxol-4-yl)-2-hydroxy-4-methyl-2-trifluoromethyl-valeric acid-ethyl ester is obtained as a yellow oil. This oil is mixed in 5 ml of ether at 0° C. with 29 mg of lithium aluminum hydride, and stirred for 1 hour at 0° C. and for another 10 hours at room temperature. The batch is added to dilute hydrochloric acid, extracted with ethyl acetate, washed with water, dried with sodium sulfate and concentrated by evaporation in a vacuum. 164 mg of 4-(7-bromo-1,3-benzodioxol-4-yl)-2-hydroxy-4-methyl-2-(trifluoromethyl)pentan-1-ol is obtained as a yellow oil.

$^1$H-NMR (CDCl$_3$), δ (ppm)=1.40 (s, 3H), 1.48 (s, 3H), 2.20–2.28 (m, 2H), 2.9 (s, 1H), 3.42 (d, 1H), 3.56 (d, 1H), 6.02 (d, 2H), 6.71 (d, 1H), 6.94 (d, 1H).

MS (ei) m/e: M$^+$=384 ($^{79}$Br)/386 ($^{81}$Br).

Diol-Example b 4-(4-Chlorophenyl)-2-hydroxy-4-methyl-2-(trifluoromethyl)pentan-1-ol 2-(4-Chlorophenyl)-2-methylpropanal:

10 g of 4-chlorobenzyl cyanide and 14.3 ml of methyl iodide in 140 ml of DMF are mixed at 0° C. in portions with sodium hydride (60% in oil). It is stirred overnight and then mixed with water and ethyl acetate. The phases are separated, and the aqueous phase is extracted with ethyl acetate.

It is extracted thoroughly with water, washed with brine, dried with sodium sulfate and concentrated by evaporation in a vacuum. After chromatography on silica gel (hexane/ethyl acetate 95:5), 11.73 g of 2-(4-chlorophenyl)-2-methylpropionitrile is obtained as a colorless oil. The latter is slowly mixed in toluene at −78° C. with 55.4 ml of diisobutylaluminium hydride solution (20% in toluene), and after 4 hours at −78° C., 50 ml of ethyl acetate was added in drops. It is stirred overnight while being heated to room temperature, and water is added. After filtering through diatomaceous earth, the phases are separated, and the aqueous phase is extracted with ethyl acetate. It is washed with water and brine, dried with sodium sulfate and concentrated by evaporation in a vacuum. After chromatography on silica gel (hexane/ethyl acetate 95:5), 10.2 g of 2-(4-chlorophenyl)-2-methylpropanal is obtained as a colorless oil.

$^1$H-NMR (CDCl$_3$), δ (ppm)=1.46 (s, 6H), 7.20 (d, 1H), 7.29–7.43 (m, 3H), 9.48 (s, 1H).

4-(4-Chlorophenyl)-4-methyl-2-oxo-valeric acid:

A solution of 15.04 g of 2-diethylphosphono-2-ethoxyacetic acid-ethyl ester in 50 ml of tetrahydrofuran is mixed while being cooled with ice within 20 minutes with 30 ml of a 2 M solution of lithium diisopropylamide in tetrahydrofuran-heptane-toluene, and it is stirred for 15 minutes at 0° C. Within 30 minutes, a solution of 10.2 g of 2-(4-chlorophenyl)-2-methylpropanal in 50 ml of tetrahydrofuran is added in drops thereto at 0° C. After 20 hours at room temperature, 2N sulfuric acid is added, it is extracted with ethyl acetate, dried (Na$_2$SO$_4$) and concentrated by evaporation. The crude product is saponified with 200 ml of 2 M sodium hydroxide solution/400 ml of ethanol. 13.8 g of acid, which is refluxed for 3 hours with 300 ml of 2N sulfuric acid and 100 ml of glacial acetic acid while being stirred vigorously, is obtained. After extraction with ethyl acetate and washing with water, 10.9 g of 4-(4-chlorophenyl)-4-methyl-2-oxo-valeric acid is obtained as a red oil.

$^1$H-NMR (CDCl$_3$), δ (ppm)=1.47 (s, 6H), 3.28 (s, 2H), 7.28 (s, 4H), 7.73 (bs, 1H).

4-(4-Chlorophenyl)-2-hydroxy-4-methyl-2-(trifluoromethyl)-pentan-1-ol:

Analogously to the synthesis of 4-(7-bromo-1,3-benzodioxol-4-yl)-2-hydroxy-4-methyl-2-(trifluoromethyl)pentan-1-ol (Diol Example 1), 4.22 g of 4-(4-chlorophenyl)-2-hydroxy-4-methyl-2-(trifluoromethyl)pentan-1-ol is obtained as a colorless oil by esterification of 10.9 g of 4-(4-chlorophenyl)-4-methyl-2-oxo-valeric acid in ethanol/sulfuric acid, reaction of the product with trifluoromethyl-trimethylsilane and tetrabutylammonium fluoride and reduction of the formed hydroxy ester with lithium aluminum hydride.

$^1$H-NMR (CDCl$_3$), δ (ppm)=1.39 (s, 3H), 1.49 (s, 3H), 2.07 (d, 1H), 2.19 (d, 1H), 2.83 (bs, 1H), 3.27 (d, 1H), 3.41 (d, 1H), 7.26–7.38 (m, 4H).

Diol-Examples c and d 4-(4-Chloro-2-methoxyphenyl)-2-hydroxy-4-methyl-2-(trifluoromethyl)pentan-1-ol and 4-(2-Chloro-4-methoxyphenyl)-2-hydroxy-4-methyl-2-(trifluoromethyl)pentan-1-ol A solution of 3 g of 2-hydroxy-4-methylene-2-(trifluoromethyl)valeric acid ethyl ester in 22 ml of 3-chloroanisole is mixed at room temperature in portions with aluminum dichloride. It is stirred for 48 hours and then mixed with 2N hydrochloric acid and hexane and stirred for 1 hour. It is washed with 2N hydrochloric acid and water, and excess 3-chloroanisole is distilled off in a vacuum. The remaining residue is purified by chromatography on silica gel (hexane/ethyl acetate 100:0→90:10). 2.85 g of a mixture of 4-(4-chloro-2-methoxyphenyl)-2-hydroxy-4-methy-2-(trifluoromethyl)valeric acid ethyl ester and 4-(2-chloro-4-methoxyphenyl)-2-hydroxy-4-methy-2-(trifluoromethyl) valeric acid ethyl ester is obtained as a yellow oil. This substance mixture is mixed in 90 ml of ether at 0° C. with 445 mg of lithium aluminum hydride, and it is stirred for 12 hours. The batch is added to saturated sodium bicarbonate solution, filtered through diatomaceous earth, the phases are separated, and the aqueous phase is extracted with ethyl acetate. It is washed with water and brine, dried with sodium sulfate and concentrated by evaporation in a vacuum. After chromatography on silica gel (hexane/ethyl acetate 95:5), 1.87 mg of 4-(4-chloro-2-methoxyphenyl)-2-hydroxy-4-methyl-2-(trifluoromethyl)pentan-1-ol is obtained as a first fraction, and 160 mg of 4-(2-chloro-4-methoxyphenyl)-2-hydroxy-4-methyl-2-(trifluoromethyl)pentan-1-ol is obtained as a second fraction as colorless oils.

$1^{st}$ Fraction: $^1$H-NMR (CDCl$_3$), δ (ppm)=1.41 (s, 3H), 1.51 (s, 3H), 2.24 (d, 1H), 2.51 (d, 1H), 2.84 (bs, 1H), 3.36 (d, 1H), 3.48 (d, 1H), 3.85 (s, 3H), 6.88 (d, 1H), 6.92 (dd, 1H), 7.24 (d, 1H).

$2^{nd}$ Fraction: $^1$H-NMR (CDCl$_3$), δ (ppm)=1.52 (s, 3H), 1.62 (s, 3H), 2.18 (d, 1H), 2.76 (d, 1H), 2.93 (bs, 1H), 3.33 (d, 1H), 3.55 (d, 1H), 3.80 (s, 3H), 6.78 (dd, 1H), 6.90 (d, 1H), 7.38 (d, 1H).

The following compounds were produced with the above-described processes of Diol-Example a to Diol-Example d:

TABLE I

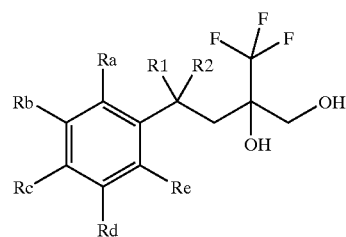

| Ex. | Diol Synthesis Process | R1/R2 | Ra–Re (≠H) | MS |
|---|---|---|---|---|
| e | b | —CH$_2$—CH$_2$— | Ra = Cl | M$^+$ + 1 = 295 ($^{35}$Cl), 297 ($^{37}$Cl); (esi) |
| f | a | CH$_3$, CH$_3$ | Ra–Rb = —O-CH$_2$—O— | M$^+$ = 306 (ei) |

TABLE I-continued

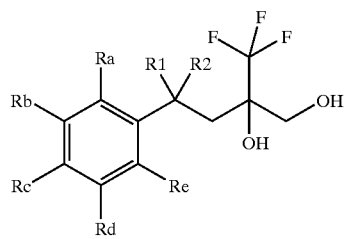

| Ex. | Diol Synthesis Process | R1/R2 | Ra–Re (≠H) | MS |
|---|---|---|---|---|
| g | b | $CH_3, CH_3$ | Ra = Cl | $M^+ = 296\ (^{35}Cl),\ 298\ (^{37}Cl);\ (ei)$ |
| h | b | $CH_3, CH_3$ | Rb = Cl | $M^+ = 296\ (^{35}Cl),\ 298\ (^{37}Cl);\ (ei)$ |
| i | a | $CH_3, CH_3$ | Ra–Rb = —O—$CH_2$—O—, Rc = Cl | $M^+ = 340\ (^{35}Cl),\ 342\ (^{37}Cl);\ (ei)$ |
| j | b | $CH_3, CH_3$ | Ra = Rc = Cl | $M^+ = 330\ (2 \times {}^{35}Cl),\ 332\ ({}^{37}Cl + {}^{35}Cl),\ 334\ (2 \times {}^{37}Cl);\ (ei)$ |
| k | b | $CH_3, CH_3$ | Ra = $CF_3$, Rd = F | $M^+ = 348\ (ei)$ |
| l | a | $CH_3, CH_3$ | Ra = $OCH_3$, Rb = Rd = F | $M^+ + 1 = 329\ (esi)$ |
| m | b | $CH_3, CH_3$ | Ra = Rd = F | $M^+ = 298\ (ci)$ |
| n | b | —$(CH_3)_3$— | Ra = Cl, Rd = F | $M^+ + NH_4 = 344\ (ci)$ |
| o | b | $CH_3, CH_3$ | Ra = Cl, Rd = F | 314, 316 ($EI^+$) |
| p | b | —$(CH_2)_2$— | Ra = Cl, Rc = F | 312, 314 ($EI^+$) |
| q | b | —$(CH_2)_2$— | Ra = Cl, Rd = F | 312, 314 ($EI^+$) |
| r | b | —$(CH_2)_3$— | Ra = $OCH_3$, Rd = F | 322, 324 ($EI^+$) |
| s | b | $CH_3, CH_3$ | Ra = Cl, Rc = F | 378 (–Cl, $EI^+$) |
| t | c | $CH_3, CH_3$ | Ra = $OCH_3$, Rd = Br | 370, 372 ($EI^+$) |

Example 76

(±)-4-(7-Bromo-1,3-benzodioxol-4-yl)-4-methyl-1-(2-methylquinolin-5-ylamino)-2-(trifluoromethyl)pentan-2-ol A solution of 160 mg of 4-(7-bromo-1,3-benzodioxol-4-yl)-2-hydroxy-4-methyl-2-(trifluoromethyl)pentan-1-ol and 111 mg of 4-toluenesulfonic acid chloride in 1.5 ml of pyridine is stirred for 70 hours at 0° C. It is concentrated by evaporation in a vacuum, taken up in 2N hydrochloric acid, and extracted with ethyl acetate. It is washed with 2N hydrochloric acid and water, dried with sodium sulfate and concentrated by evaporation in a vacuum. 188 mg of 4-toluenesulfonic acid-[4-(7-bromo-1,3-benzodioxol-4-yl)-2-hydroxy-4-methyl-2-(trifluoromethyl)]pentylester is obtained as a yellow oil. The latter is added to a solution, which is prepared from 94 mg of N-acetyl-5-amino-2-methylquinoline and sodium hydride (60% in oil) in 1.5 ml DMF at 0° C., and it is stirred for 1.5 hours. It is heated to 50° C. for 1 hour. It is stirred for another 70 hours at room temperature and added to saturated sodium bicarbonate solution. It is extracted with ethyl acetate, washed with water and brine, dried with sodium sulfate and concentrated by evaporation in a vacuum. After chromatography on silica gel (hexane/ethyl acetate 100:0→85:15), 74 mg of N-acetyl-(7-bromo-1,3-benzodioxol-4-yl)-4-methyl-1-[(2-methylquinolin-5-yl)amino]-2-(trifluoromethyl)pentan-2-ol is obtained as a yellow oil. The latter is heated with 4 ml of ethanol and 1.2 ml of 1N sodium hydroxide solution for 8 hours to 100° C. It is concentrated by evaporation in a vacuum and extracted with ethyl acetate. It is washed with water and brine, dried with sodium sulfate and concentrated by evaporation in a vacuum. After chromatography on silica gel (hexane/ethyl acetate 100:0→85:15), 51 mg of the title compound is obtained as a yellow foam.

$^1$H-NMR (CDCl$_3$), δ (ppm)=1.46 (s, 3H), 1.58 (s, 3H), 2.29 (d 1H), 2.50 (d, 1H), 2.74 (s, 3H), 3.13 (bs, 1H), 3.18 (dd, 1H), 3.35 (dd, 1H), 4.30 (bs, 1H), 5.98 (s, 2H), 6.11 (d, 1H), 6.80 (d, 1H), 7.00 (d, 1H), 7.21 (d, 1H), 7.49 (d, 1H), 7.52 (d, 1H), 7.95 (d, 1H).

Examples 77, 78

(−)-4-(7-Bromo-1,3-benzodioxol-4-yl)-4-methyl-1-[(2-methylquinolin-5-yl)amino]-2-(trifluoromethyl)pentan-2-ol (+)-4-(7-bromo-1,3-benzodioxol-4-yl)-4-methyl-1-[(2-methylquinolin-5-yl)amino]-2-(trifluoromethyl)pentan-2-ol Separation of (±)-4-(7-bromo-1,3-benzodioxol-4-yl)-4-methyl-1-[(2-methylquinolin-5-yl)amino]-2-(trifluoromethyl)pentan-2-ol:

The enantiomer mixture is separated by chromatography on chiral carrier material (CHIRALPAK AD®, DAICEL Company) with hexane/ethanol/triethylamine (98:2:0.1, vvv).

(−)-Enantiomer: MS (ei): $M^+=524\ (^{79}Br)\ 526\ (^{81}Br)$, [ ]$_D$−50.4° (c=0.5, CHCl$_3$) and (+)-Enantiomer: MS (ei): $M^+=524\ (^{79}Br)\ 526\ (^{81}Br)$ are thus obtained.

Example 79

(±)-4-(4-Chlorophenyl)-4-methyl-1-[(2-methylquinolin-5-yl)amino]-2-(trifluoromethyl)pentan-2-ol 0.674 ml of oxalyl chloride in 16.8 ml of dichloromethane is mixed at −78° C. with 1.15 ml of DMSO in 3.4 ml of dichloromethane. After 5 minutes, 2 g of 4-(4-chlorophenyl)-2-hydroxy-4-methyl-2-(trifluoromethyl) pentan-1-ol in 6.8 ml of dichloromethane is added in drops at −78° C. After 15 minutes, it is mixed with 4.7 ml of triethylamine and slowly heated to room temperature. It is washed with water and brine, dried with sodium sulfate and concentrated by evaporation in a vacuum. After chromatography on silica gel (hexane/ethyl acetate 98:2), 1.07 g of 4-(4-chlorophenyl)-2-hydroxy-4-methyl-2-(trifluoromethyl)-pentanal is obtained as a colorless oil. 300 mg thereof was heated with 194 mg of 5-amino-2-methylquinoline in 9 ml of glacial acetic acid for 4.5 hours to 130° C. After toluene is added, it is concentrated by evaporation in a vacuum. The residue is taken up in methanol and mixed at 0° C. with 153 mg of sodium borohydride. It is allowed to stir for 5 hours at room temperature, and water is added. The batch is concentrated by evaporation in a vacuum, extracted with ethyl acetate, washed with water and brine, dried with sodium sulfate and concentrated by evaporation in a vacuum. After chromatography on silica gel (hexane/ethyl acetate 100:0→85:15), 163 mg of the title compound is obtained as a yellow solid.

Flash point: 137–139° C.

Examples 80, 81

(−)-4-(4-Chlorophenyl)-4-methyl-1-[(2-methylquinolin-5-yl)amino]-2-(trifluoromethyl) pentan-2-ol (+)-4-(4-Chlorophenyl)-4-methyl-1-[(2-methylquinolin-5-yl)amino]-2-(trifluoromethyl) pentan-2-ol Separation of (±)-4-(4-Chlorophenyl)-4-methyl-1-[(2-methylquinolin-5-yl)amino]-2-(trifluoromethyl)pentan-2-ol:

The enantiomer mixture is separated by chromatography on chiral carrier material (CHIRALPAK AD®, DAICEL Company) with hexane/ethanol (97:3, vvv).

(−)-Enantiomer: MS (esi): $M^+ + 1 = 437$ ($^{35}$Cl) 439 ($^{37}$Cl), $[\alpha]_D = 47.0°$ (c=0.75, CHCl$_3$) and (+)-Enantiomer: MS (esi): $M^+ + 1 = 437$ ($^{35}$Cl) 439 ($^{37}$Cl) are thus obtained.

Example 82

4-(1,3-Benzodioxol-4-yl)-4-methyl-1-[(quinolin-5-yl)amino]-2-(trifluoromethyl)pentan-2-ol A solution that consists of 2.44 g of 4-(1,3-benzodioxol-4-yl)-2-hydroxy-4-methyl-2-(trifluoromethyl)-pentan-1-ol and 1.72 g of 4-toluenesulfonic acid chloride in 18 ml of pyridine is stirred for 70 hours at 9° C. It is concentrated by evaporation in a vacuum, taken up in 2N hydrochloric acid and extracted with ethyl acetate. It is washed with 2N hydrochloric acid and water, dried with sodium sulfate and concentrated by evaporation in a vacuum. After chromatography on silica gel (hexane/ethyl acetate 100:0→90:10), 3.97 g of 4-toluenesulfonic acid-[4-(1,3-benzodioxol-4-yl)-2-hydroxy-4-methyl-2-(trifluoromethyl)]-pentyl ester is obtained as a colorless oil. 1.35 g thereof in 40 ml of THF is mixed with 118 mg of sodium hydride (60% in oil) and heated for 4 hours to 60° C. Water is added, and it is extracted with ethyl acetate. It is washed with water and brine, dried with sodium sulfate and concentrated by evaporation in a vacuum. After chromatography on silica gel (hexane/ethyl acetate 98:2), 630 mg of 2-[2-(1,3-benzodioxol-4-yl)-2-(methylpropyl)]-2-(trifluoromethyl) oxirane is obtained as a yellow oil. 230 mg thereof with 230 mg of 5-aminoquinoline in 5 ml of DMSO is heated for 5 hours to 120° C. Water is added, and it is extracted with ethyl acetate. It is washed with water and brine, dried with sodium sulfate and concentrated by evaporation in a vacuum. After chromatography on silica gel (dichloromethane/acetone 99:1), 27 mg of the title compound is obtained.

MS (esi): $M^+ + 1 = 433$.

According to the above-described process, the following compounds of Table II were obtained:

TABLE II

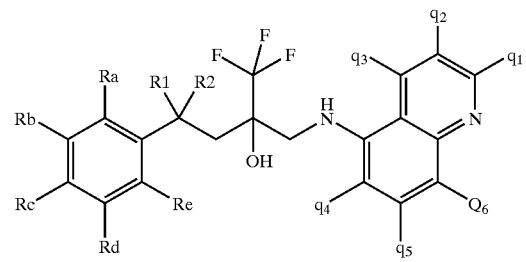

| Ex. | Synthesis Process | R1/R2 | Ra–Re (≠H)[1] | q1–q6 (≠H)[2] | Analysis[3] | Isomerism |
|---|---|---|---|---|---|---|
| 83 | Example 76 | CH$_3$/CH$_3$ | Ra–Rb = —O—CH$_2$—O— | q1 = CH$_3$ | MS: M$^+$ = 477 (ei) | Racemate |
| 84 | Examples 77, 78 | CH$_3$/CH$_3$ | Ra–Rb = —O—CH$_2$—O— | q1 = CH$_3$ | MS: M$^+$ = 477 (ei) | −51.2 (c = 1, CHCl$_3$) |
| 85 | Examples 77, 78 | CH$_3$/CH$_3$ | Ra–Rb = —O—CH$_2$—O— | q1 = CH$_3$ | MS: M$^+$ = 477 (ei) | +54.7 (c = 0.5, CHCl$_3$) |
| 86 | Example 79 | CH$_3$/CH$_3$ | Rb = Cl | | MS: M$^+$ = 422/424 (ei) | Racemate |
| 87 | Examples 80, 81 | CH$_3$/CH$_3$ | Rb = Cl | | MS: M$^+$ = 422/424 (ei) | −28.1 (c = 0.35, MeOH/CHCl$_3$) |

TABLE II-continued

[Structure: quinoline amine with trifluoromethyl-hydroxy-phenyl substituent, positions labeled Ra-Re on phenyl, q1-q6 on quinoline, R1/R2 on central carbon]

| Ex. | Synthesis Process | R1/R2 | Ra–Re (≠H)[1] | q1–q6 (≠H)[2] | Analysis[3] | Isomerism |
|---|---|---|---|---|---|---|
| 88 | Examples 80, 81 | $CH_3/CH_3$ | Rb = Cl | | MS: M⁺ = 422/424 (ei) | +26.7 (c = 0.5, $CHCl_3$) |
| 89 | Example 79 | $CH_3/CH_3$ | Rc = Cl | | MS: M⁺ = 423/425 (esi) | Racemate |
| 90 | Example 79 | $CH_3/CH_3$ | Ra = Cl | | Flash point = 186–187° C. | Racemate |
| 91 | Examples 80, 81 | $CH_3/CH_3$ | Ra = Cl | | MS: M⁺ + 1 = 423/425 (esi) | −26.0 (c = 0.5, $CHCl_3$) |
| 92 | Examples 80, 81 | $CH_3/CH_3$ | Ra = Cl | | MS: M⁺ = 422/424 (ei) | +17.3 (c = 1.1, $CHCl_3$) |
| 93 | Example 79 | $CH_3/CH_3$ | Ra = Cl | q1 = $CH_3$ | MS: M⁺ = 436/438 (ei) | Racemate |
| 94 | Examples 80, 81 | $CH_3/CH_3$ | Ra = Cl | q1 = $CH_3$ | MS: M⁺ = 436/438 (ei) | −15.5 (c = 0.5, $CHCl_3$) |
| 95 | Examples 80, 81 | $CH_3/CH_3$ | Ra = Cl | q1 = $CH_3$ | MS: M⁺ = 436/438 (ei) | +18.7 (c = 0.6, $CHCl_3$) |
| 96 | Example 76 | $CH_3/CH_3$ | Ra–Rb = —O—$CH_2$—O—, Rc = Cl | q1 = $CH_3$ | MS: M⁺ = 480/482 (ei) | Racemate |
| 97 | Examples 77, 78 | $CH_3/CH_3$ | Ra–Rb = —O—$CH_2$—O—, Rc = Cl | q1 = $CH_3$ | MS: M⁺ = 480/482 (ei) | −29.0 (c = 0.45, $CHCl_3$) |
| 98 | Examples 77, 78 | $CH_3/CH_3$ | Ra–Rb = —O—$CH_2$—O—, Rc = Cl | q1 = $CH_3$ | MS: M⁺ = 480/482 (ei) | (+)-Enantiomer |
| 99 | Example 79 | $CH_3/CH_3$ | Rb = Cl | q1 = $CH_3$ | MS: M⁺ = 436/438 (ei) | Racemate |
| 100 | Examples 80, 81 | $CH_3/CH_3$ | Rb = Cl | q1 = $CH_3$ | MS: M⁺ = 436/438 (ei) | −34.6 (c = 1.0, $CHCl_3$) |
| 101 | Examples 80, 81 | $CH_3/CH_3$ | Rb = Cl | q1 = $CH_3$ | MS: M⁺ = 436/438 (ei) | (+)-Enantiomer |
| 102 | Example 79 | $CH_3/CH_3$ | Ra = Rc = Cl | q1 = $CH_3$ | MS: M⁺ = 470, 472, 474 (ei) | Racemate |
| 103 | Examples 80, 81 | $CH_3/CH_3$ | Ra = Rc = Cl | q1 = $CH_3$ | MS: M⁺ = 470, 472, 474 (ei) | (−)-Enantiomer |
| 104 | Examples 80, 81 | $CH_3/CH_3$ | Ra = Rc = Cl | q1 = $CH_3$ | MS: M⁺ = 470, 472, 474 (ei) | +15.7 (c = 0.5, $CHCl_3$) |
| 105 | Example 79 | $CH_3/CH_3$ | Ra = $CF_3$, Rd = F | q1 = $CH_3$ | MS: M⁺ = 488 (ei) | Racemate |
| 106 | Examples 80, 81 | $CH_3/CH_3$ | Ra = $CF_3$, Rd = F | q1 = $CH_3$ | MS: M⁺ = 488 (ei) | −20.5 (c = 1.0, $CHCl_3$) |
| 107 | Examples 80, 81 | $CH_3/CH_3$ | Ra = $CF_3$, Rd = F | q1 = $CH_3$ | MS: M⁺ = 488 (ei) | (+)-Enantiomer |
| 108 | Example 79 | —$CH_2$—$CH_2$— | Ra = Cl | q1 = $CH_3$ | MS: M⁺ + 1 = 435, 437 (ci) | Racemate |
| 109 | Examples 80, 81 | —$CH_2$—$CH_2$— | Ra = Cl | q1 = $CH_3$ | MS: M⁺ = 434, 436 (ei) | −6.4 (c = 0.5, $CHCl_3$) |
| 110 | Examples 80, 81 | —$CH_2$—$CH_2$— | Ra = Cl | q1 = $CH_3$ | MS: M⁺ = 434, 436 (ei) | +5.0 (c = 0.5, $CHCl_3$) |

TABLE II-continued

| Ex. | Synthesis Process | R1/R2 | Ra–Re (≠H)[1)] | q1–q6 (≠H)[2)] | Analysis[3)] | Isomerism |
|---|---|---|---|---|---|---|
| 111 | Example 76 | CH$_3$/CH$_3$ | Ra = OCH$_3$, Rc = Cl | q1 = CH$_3$ | MS: M$^+$ = 466, 468 (ei) | Racemate |
| 112 | Examples 77, 78 | CH$_3$/CH$_3$ | Ra = OCH$_3$, Rc = Cl | q1 = CH$_3$ | MS: M$^+$ = 466, 468 (ei) | (−)-Enantiomer |
| 113 | Examples 77, 78 | CH$_3$/CH$_3$ | Ra = OCH$_3$, Rc = Cl | q1 = CH$_3$ | MS: M$^+$ = 466, 468 (ei) | +34.1 (c = 1.0, CHCl$_3$) |
| 114 | Example 82 | CH$_3$/CH$_3$ | Ra–Rb = —O—CH$_2$—O— | q1 = Cl | MS: M$^+$ + 1 = 467, 469 (ci) | Racemate |
| 115 | Example 76 | CH$_3$/CH$_3$ | Ra = OCH$_3$, Rb = Rd = F | q1 = CH$_3$ | MS: M$^+$ + 1 = 469 (esi) | Racemate |
| 116 | Examples 77, 78 | CH$_3$/CH$_3$ | Ra = OCH$_3$, Rb = Rd = F | q1 = CH$_3$ | MS: M$^+$ = 468 (ei) | −11.0 (c = 0.45, CHCl$_3$) |
| 117 | Examples 77, 78 | CH$_3$/CH$_3$ | Ra = OCH$_3$, Rb = Rd = F | q1 = CH$_3$ | MS: M$^+$ = 468 (ei) | (+)-Enantiomer |
| 118 | Example 4 | CH$_3$/CH$_3$ | Ra = OH, Rb = Rd = F | q1 = CH$_3$ | MS: M$^+$ + 1 = 455 (esi) | −10.0 (c = 0.3, CHCl$_3$) |
| 119 | Example 4 | CH$_3$/CH$_3$ | Ra = OH, Rb = Rd = F | q1 = CH$_3$ | MS: M$^+$ + 1 = 455 (esi) | (+)-Enantiomer |
| 120 | Example 4 | CH$_3$/CH$_3$ | Ra = OH, Rc = Cl | q1 = CH$_3$ | Flash point: 107–108° C. | (−)-Enantiomer |
| 121 | Example 4 | CH$_3$/CH$_3$ | Ra = OH, Rc = Cl | q1 = CH$_3$ | Flash point: 106–107° C. | (+)-Enantiomer |
| 122 | Example 71 | CH$_3$/CH$_3$ | Ra = OCH$_3$, Rd = F | q1 = CH$_3$, q6 = F | MS: M$^+$ + 1 = 469 (esi) | Racemate |
| 123 | Example 4 | CH$_3$/CH$_3$ | Ra = OH, Rd = F | q1 = CH$_3$, q6 = F | MS: M$^+$ + 1 = 455 (esi) | Racemate |
| 124 | Example 79 | CH$_3$/CH$_3$ | Ra = OCH$_3$, Rd = F | q1 = CH$_3$, q4 = F | MS: M$^+$ + 1 = 469 (esi) | Racemate |
| 125 | Example 4 | CH$_3$/CH$_3$ | Ra = OH, Rd = F | q1 = CH$_3$, q4 = F | MS: M$^+$ + 1 = 455 (esi) | Racemate |
| 126 | Example 79 | CH$_3$/CH$_3$ | Ra–Rb = —O—CH$_2$—O— | q1 = CH$_3$, q6 = F | MS: M$^+$ + 1 = 463 (esi) | Racemate |
| 127 | Example 79 | CH$_3$/CH$_3$ | Rb = Cl | q1 = OH* | MS: M$^+$ + 1 = 439, 441 (esi) | Racemate |
| 128 | Example 79 | —CH$_2$—CH$_2$— | Ra = Cl | q1 = OH* | MS: M$^+$ + 1 = 435, 437 (ci) | Racemate |
| 129 | Example 79 | CH$_3$/CH$_3$ | Ra–Rb = —O—CH$_2$—O— | q1 = OH* | MS: M$^+$ = 448 (ei) | Racemate |
| 130 | Example 79 | CH$_3$/CH$_3$ | Ra = OCH$_3$, Rc = Cl | q1 = OH* | MS: M$^+$ + 1 = 469, 471 (esi) | Racemate |
| 131 | Example 76 | —CH$_2$—CH$_2$— | Ra = Rd = F | q1 = CH$_3$ | MS: M$^+$ + 1 = 437 (esi) | Racemate |
| 132 | Example 79 | CH$_3$/CH$_3$ | Ra = Rd = F | q1 = CH$_3$ | MS: M$^+$ + 1 = 438 (esi) | Racemate |
| 133 | Examples 77, 78 | CH$_3$/CH$_3$ | Ra = Rd = F | q1 = CH$_3$ | | (−)-Enantiomer |
| 134 | Examples 77, 78 | CH$_3$/CH$_3$ | Ra = Rd = F | q1 = CH$_3$ | | +27.1 (c = 0.33, CHCl$_3$) |
| 135 | Example 79 | —(CH$_2$)$_3$— | Ra = Rd = F | q1 = CH$_3$ | MS: M$^+$ + 1 = 451 (ci) | |
| 136 | Example 79 | —(CH$_2$)$_3$— | Ra = Cl, Rd = F | q1 = CH$_3$ | MS: M$^+$ + 1 = 467 (esi) | Racemate |
| 137 | Examples 77, 78 | —(CH$_2$)$_3$— | Ra = Cl, Rd = F | q1 = CH$_3$ | | (+)-Enantiomer |

TABLE II-continued

[Structure: trifluoromethyl carbinol with substituted phenyl (Ra, Rb, Rc, Rd, Re) connected via CR1R2-CH2-C(CF3)(OH)-CH2-NH- to quinoline (q1, q2, q3, q4, q5, Q6)]

| Ex. | Synthesis Process | R1/R2 | Ra–Re (≠H)[1] | q1–q6 (≠H)[2] | Analysis[3] | Isomerism |
|---|---|---|---|---|---|---|
| 138 | Examples 77, 78 | —(CH$_2$)$_3$— | Ra = Cl, Rd = F | q1 = CH$_3$ | | −29.2 (c = 0.61, CHCl$_3$) |
| 139 | Examples 77,78 | CH$_3$/CH$_3$ | Ra = OCH$_3$, Rc = Br | | Flash point: 131–134° C., MS: 496, 498 (EI$^+$) | −32.7° c = 0.5, THF |
| 140 | Examples 77, 78 | CH$_3$/CH$_3$ | Ra = OCH$_3$, Rc = Br | | Flash point: 132–135° C., MS: 496, 498 (EI$^+$) | +36.7° c = 0.5, THF |
| 141 | Example 4 | CH$_3$/CH$_3$ | Ra = OH, Rc = Br | | Flash point: 105° C., MS: 482, 484 (EI+) | Racemate |
| 142 | Examples 77, 78 | CH$_3$/CH$_3$ | Ra = OH, Rc = Br | | MS: 482, 484 (EI+) | (−) Enantiomer |
| 143 | Examples 77, 78 | CH$_3$/CH$_3$ | Ra = OH, Rc = Br | | MS: 482, 484 (EI+) | +34.5° c = 0.5, THF |
| 144 | Example 76 | CH$_3$/CH$_3$ | Ra = OCH$_3$, Rc = Br | q1 = CH$_3$ | Flash point: 146–147° C. MS: 510, 512 (EI$^+$) | Racemate |
| 145 | Examples 77, 78 | CH$_3$/CH$_3$ | Ra = OCH$_3$, Rc = Br | q1 = CH$_3$ | MS: 510, 512 (EI$^+$) | (−) Enantiomer |
| 146 | Examples 77, 78 | CH$_3$/CH$_3$ | Ra = OCH$_3$, Rc = Br | q1 = CH$_3$ | MS: 510, 512 (EI$^+$) | +38.5° c = 0.5, THF |
| 147 | Example 4 | CH$_3$/CH$_3$ | Ra = OH, Rc = Br | q1 = CH$_3$ | MS: 496, 498 (EI$^{30}$) | Racemate |
| 148 | Examples 77, 78 | CH$_3$/CH$_3$ | Ra = OH, Rc = Br | q1 = CH$_3$ | MS: 496, 498 (EI$^+$) | (−) Enantiomer |
| 149 | Examples 77,78 | CH$_3$/CH$_3$ | Ra = OH, Rc = Br | q1 = CH$_3$ | MS: 496, 498 (EI$^+$) | +41.2° c = 0.5, THF |
| 150 | Example 76 | CH$_3$/CH$_3$ | Ra = OCH$_3$, Rd = Br | | Flash point: 138° C., MS: 496, 498 (EI$^+$) | Racemate |
| 151 | Example 4 | CH$_3$/CH$_3$ | Ra = OH, Rd = Br | | MS: 482, 484 | Racemate |
| 152 | Examples 77, 78 | CH$_3$/CH$_3$ | Ra = OH, Rd = Br | | Flash point: 124–126° C., MS: 482, 484 | (+) Enantiomer |
| 153 | Examples 77, 78 | CH$_3$/CH$_3$ | Ra = OH, Rd = Br | | Flash point: 124–126° C., MS: 482, 484 | −45.0° c = 0.5, THF |
| 154 | Example 76 | CH$_3$/CH$_3$ | Ra = OCH$_3$, Rd = Br | q1 = CH$_3$ | Flash point: 155° C., MS: 510, 512 (EI$^+$) | Racemate |
| 155 | Examples 77, 78 | CH$_3$/CH$_3$ | Ra = OH, Rd = Br | q1 = CH$_3$ | MS: 496, 498 (EI$^+$) | (+) Enantiomer |
| 156 | Examples 77, 78 | CH$_3$/CH$_3$ | Ra = OH, Rd = Br | q1 = CH$_3$ | MS: 496, 498 (EI$^+$) | −42.0° c = 0.5, THF |
| 157 | Example 76 | CH$_3$/CH$_3$ | Ra = Cl, Rd = F | | Flash point: 180–182° C., MS: 440, 442 (EI$^+$) | Racemate |

TABLE II-continued

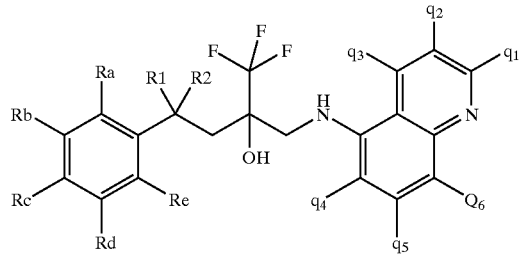

| Ex. | Synthesis Process | R1/R2 | Ra–Re (≠H)[1] | q1–q6 (≠H)[2] | Analysis[3] | Isomerism |
|---|---|---|---|---|---|---|
| 158 | Examples 77, 78 | CH$_3$/CH$_3$ | Ra = Cl, Rd = F | | Flash point: 141–142° C., MS: 440, 442 (EI$^+$) | (+) Enantiomer |
| 159 | Examples 77, 78 | CH$_3$/CH$_3$ | Ra = Cl, Rd = F | | Flash point: 142° C., MS: 440, 442 (EI$^+$) | (−) Enantiomer |
| 160 | Example 76 | CH$_3$/CH$_3$ | Ra = Cl, Rd = F | q1 = CH$_3$ | Flash point: 132–133° C., MS: 454, 456 (EI$^+$) | Racemate |
| 161 | Examples 77, 78 | CH$_3$/CH$_3$ | Ra = Cl, Rd = F | q1 = CH$_3$ | Flash point: 178° C., MS: 454, 456 (EI$^+$) | (+) Enantiomer |
| 162 | Examples 77, 78 | CH$_3$/CH$_3$ | Ra = Cl, Rd = F | q1 = CH$_3$ | Flash point: 177° C., MS: 454, 456 (EI$^+$) | −3.4° c = 0.5, THF |
| 163 | Example 76 | —CH$_2$—CH$_2$— | Ra = Cl, Rd = F | | Flash point: 171° C., MS: 438, 440 (EI$^+$) | Racemate |
| 164 | Example 76 | —CH$_2$—CH$_2$— | Ra = Cl, Rd = F | q1 = CH$_3$ | Flash point: 171° C., MS: 452, 454 (EI$^+$) | Racemate |
| 165 | Example 76 | CH$_3$/CH$_3$ | Ra = Cl, Rc = F | | Flash point: 164–166° C., MS: 440 (EI$^+$) | Racemate |
| 166 | Example 76 | CH$_3$/CH$_3$ | Ra = Cl, Rc = F | q1 = CH$_3$ | Flash point: 128–130° C., MS: 454, 456 (EI$^+$) | Racemate |
| 167 | Examples 77, 78 | CH$_3$/CH$_3$ | Ra = Cl, Rc = F | q1 = CH$_3$ | Flash point: 128° C., MS: 454, 456 (EI$^+$) | −1.5° c = 0.5, THF |
| 168 | Examples 77, 78 | CH$_3$/CH$_3$ | Ra = Cl, Rc = F | q1 = CH$_3$ | Flash point: 128° C., MS: 454, 456 (EI$^+$) | (+) Enantiomer |
| 169 | Example 76 | —CH$_2$—CH$_2$— | Ra = Cl, Rc = F | | Flash point: 172–173° C., MS: 452, 454 (EI$^+$) | Racemate |
| 170 | Example 76 | —(CH$_2$)$_3$— | Ra = OCH$_3$, Rd = F | | Flash point: 130° C., MS: 448, 449 (EI$^+$) | Racemate |
| 171 | Examples 77, 78 | —(CH$_2$)$_3$— | Ra = OCH$_3$, Rd = F | | Flash point: 132–134° C., MS: 448, 449 (EI$^+$) | −18.0° c = 0.5, THF |
| 172 | Examples 77, 78 | —(CH$_2$)$_3$— | Ra = OCH$_3$, Rd = F | | Flash point: 133–134° C., MS: 448, 449 (EI$^+$) | (+) Enantiomer |
| 173 | Example 4 | —(CH$_2$)$_3$— | Ra = OH, Rd = F | | MS: 434, 435 (EI$^{30}$) | Racemate |

TABLE II-continued

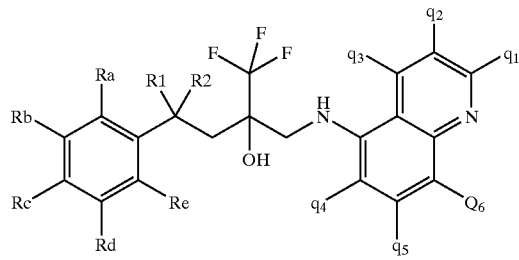

| Ex. | Synthesis Process | R1/R2 | Ra–Re (≠H)[1] | q1–q6 (≠H)[2] | Analysis[3] | Isomerism |
|---|---|---|---|---|---|---|
| 174 | Examples 77, 78 | —(CH$_2$)$_3$— | Ra = OH, Rd = F | | MS: 434 (EI$^+$) | −18.1° c = 0.5, THF |
| 175 | Examples 77, 78 | —(CH$_2$)$_3$— | Ra = OH, Rd = F | | MS: 434 (EI$^+$) | (+) Enantiomer |
| 176 | Example 76 | —(CH$_2$)$_3$— | Ra = OCH$_3$, Rd = F | | Flash point: 188° C., MS: 462, 463 (EI$^+$) | Racemate |
| 177 | Examples 77, 78 | —(CH$_2$)$_3$— | Ra = OCH$_3$, Rd = F | | Flash point: 188° C., MS: 462, 463 (EI$^+$) | −13.2° c = 0.4, CHCl$_3$ |
| 178 | Examples 77, 78 | —(CH$_2$)$_3$— | Ra = OCH$_3$, Rd = F | | Flash point: 188° C., MS: 462, 463 (EI$^+$) | (+) Enantiomer |
| 179 | Example 4 | —(CH$_2$)$_3$— | Ra = OH, Rd = F | q1 = CH$_3$ | MS: 448, 449 | Racemate |
| 180 | Examples 77, 78 | —(CH$_2$)$_3$— | Ra = OH, Rd = F | q1 = CH$_3$ | MS: 448, 449 | −12.0° c = 0.4, CHCl$_3$ |
| 181 | Examples 77, 78 | —(CH$_2$)$_3$— | Ra = OH, Rd = F | q1 = CH$_3$ | MS: 448, 449 | (+) Enantiomer |
| 182 | Example 82 | CH$_3$/CH$_3$ | | q6 = Br | Flash point: 176° C., MS: 466, 466 (EI$^+$) | Racemate |
| 183 | Example 79 | CH$_3$/CH$_3$ | Ra = OCH$_3$, Rd = F | q6 = Br | Flash point: 200° C., MS: 514, 516 (EI$^+$) | Racemate |
| 184 | Example 4 | CH$_3$/CH$_3$ | Ra = OH, Rd = F | q6 = Br | MS: 500, 502 (EI$^+$) | Racemate |
| 185 | Example 79 | CH$_3$/CH$_3$ | Ra = OCH$_3$, Rd = F | q6 = Cl | Flash point: 188–189° C., MS: 470, 472 (EI$^+$) | Racemate |
| 186 | Example 4 | CH$_3$/CH$_3$ | Ra = OH, Rd = F | q6 = Cl | Flash point: 184° C., MS: 456, 458 (EI$^+$) | Racemate |
| 187 | Example 79 | CH$_3$/CH$_3$ | Ra = OCH$_3$, Rd = F | q4 = Cl | Flash point: 132° C., MS: 470, 472 (EI$^+$) | Racemate |
| 188 | Example 4 | CH$_3$/CH$_3$ | Ra = OH, Rd = F | q4 = Cl | MS: 456, 458 (EI$^+$) | Racemate |

[1] Ra–Re (≠H) means that in the column, all radicals Ra–Re are indicated that do not mean hydrogen; any radicals Ra–Re that are not indicated = hydrogen
[2] q1–q6 (≠H) means that all radicals q1–q6 are indicated that do not mean hydrogen; any radicals q1–q6 that are not indicated = hydrogen.
[3] Analysis: MS = Mass spectrometry, flash point = melting point (fixed point)
*OH is to indicate that the compound can be present as a tautomeric equilibrium

Example 189

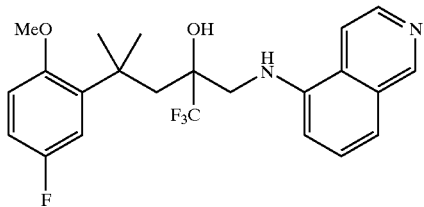

4-(5-Fluoro-2-methoxyphenyl)-1-(isoquinolin-5-ylamino)-4-methyl-2-(trifluoromethyl)pentan-2-ol Analogously to Example 20, 500 mg (1.6 mmol) of 4-(5-fluoro-2-methoxyphenyl)-2-hydroxy-4-methyl-2-(trifluoromethyl)pentanal and 500 mg (1.9 mmol) of 5-aminoisoquinoline in 16 ml of acetic acid are reacted to form 4-(5-fluoro-2-methoxyphenyl)-4-methyl-1-(isoquinolin-5-ylimino)-2-(trifluoromethyl)-pentan-2-ol and subsequently reduced with 509 mg (2.4 mmol) of sodium triacetoxy borohydride. After chromatography on silica gel with hexane-ethyl acetate (0–60%), 221 mg of product is obtained.

H-NMR (CDCl$_3$); δ=1.46 (s, 3H), 1.60 (s, 3H), 2.33 (d, 1H), 2.81 (d, 1H), 3.12 (dd, 1H), 3.24 (br, 1H), 3.30 (dd, 1H), 3.84 (s, 3H), 4.32 (br, 1H), 6.19 (dd, 1H), 6.78 (dd, 1H), 6.92 (td, 1H), 7.13 (dd, 1H), 7.38 (m, 3H), 8.44 (d, 1H), 9.12 (s, 1H).

Example 190

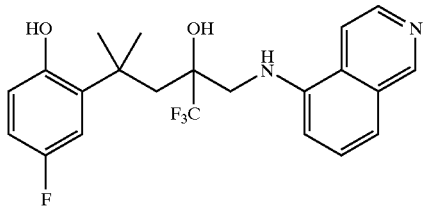

4-(5-Fluoro-2-hydroxyphenyl)-1-(isoquinolin-5-yl)-4-methyl-2-(trifluoromethyl)pentan-2-ol Analogously to Example 2, 100 mg (0.15 mmol) of 4-(5-fluoro-2-methoxyphenyl)-1-(isoquinolin-5-ylamino)-4-methyl-2-(trifluoromethyl)pentan-2-ol is reacted with 4.6 ml of 1 M boron tribromide-CH$_2$Cl$_2$ solution. After chromatography on silica gel with hexane-ethyl acetate (0–80%), 13 mg of the product is obtained.

H-NMR (CD$_3$OD); δ=1.48 (s, 3H), 1.67 (s, 3H), 1.98 (d, 1H), 3.00 (d, 1H), 3.25 (d, 1H), 3.43 (d, 1H), 6.22 (dd, 1H), 6.40 (dd, 1H), 6.53 (td, 1H), 7.01 (dd, 1H), 7.34 (m, 2H), 7.71 (d, 1H), 8.37 (d, 1H), 9.06 (s, 1H).

Example 191

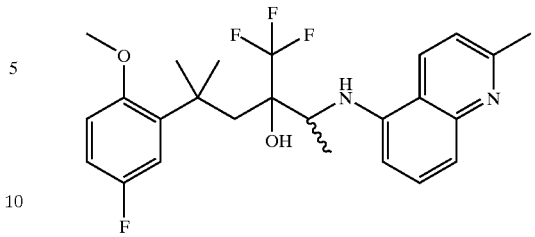

5-(5-Fluoro-2-methoxyphenyl)-5-methyl-2-(2-methylquinolin-5-ylamino)-3-(trifluoromethyl)hexan-3-ol 5-(5-Fluoro-2-methoxyphenyl)-5-methyl-3-(trifluoromethyl)hexane-2,3-diol 8 ml of 3 M methylmagnesium chloride-tetrahydrofuran solution is added in drops to the solution of 3.6 mg (11.7 mmol) of 4-(5-fluoro-2-methoxyphenyl)-2-hydroxy-4-methyl-2-(trifluoromethyl)pentanal in 150 ml of diethyl ether at +2° C. Stirring is continued for 1 hour at +2° C. and for 2 hours at room temperature. Then, it is hydrolyzed with saturated ammonium chloride solution while being cooled with ice, the organic phase is separated, dried on sodium sulfate and concentrated by evaporation. Column chromatography on silica gel with hexane-ethyl acetate yields 2.23 g of the product.

5-(5-Fluoro-2-methoxyphenyl)-3-hydroxy-5-methyl-3-(trifluoromethyl)hexan-2-one 1.46 g (4.5 mmol) of 5-(5-fluoro-2-methoxyphenyl)-5-methyl-3-(trifluoromethyl)hexane-2,3-diol and 3.14 ml (22.5 mmol) of triethylamine in 16.3 ml of DMSO and 50 ml of methylene chloride are mixed in portions with 4.3 g (27 mmol) of pyridine-sulfur trioxide complex at room temperature. After 20 hours at room temperature, it is hydrolyzed with saturated ammonium chloride solution while being cooled with ice and extracted with diethyl ether. The combined extracts are dried (sodium sulfate) and concentrated by evaporation. Column chromatography on silica gel with hexane-ethyl acetate yields 1.04 g of the product.

5-(5-Fluoro-2-methoxyphenyl)-5-methyl-2-(2-methylquinolin-5-ylimino)-3-(trifluoromethyl)hexan-3-ol 645 mg (2 mmol) of 5-(5-fluoro-2-methoxyphenyl)-3-hydroxy-5-methyl-3-(trifluoromethyl) hexan-2-one is refluxed in 4 ml of tetrahydrofuran under nitrogen with 0.84 ml (4 mmol) of titanium tetraethylate and 348 mg (2.2 mmol) of 5-amino-2-methylquinoline for 24 hours. After cooling to room temperature, the reaction mixture is stirred into 20 ml of saturated NaCl solution, 50 ml of ethyl acetate is added, and it is stirred for 30 minutes, suctioned off on Celite, and rewashed with ethyl acetate and with tetrahydrofuran. The organic phase is separated, dried (sodium sulfate) and concentrated by evaporation. Chromatography on silica gel with hexane-ethyl acetate yields 578 mg of the product.

5-(5-Fluoro-2-methoxyphenyl)-5-methyl-2-(2-methylquinolin-5-ylamino)-3-(trifluoromethyl)hexan-3-ol 231 mg (0.5 mmol) of 5-(5-fluoro-2-methoxyphenyl)-5-methyl-2-(2-methylquinolin-5-ylimino)-3-(trifluoromethyl)hexan-3-ol is mixed in 10 ml of tetrahydrofuran and 4 ml of ethanol with 0.21 ml (1 mmol) of titanium tetraethylate. Then, 875 mg (23.1 mmol) of sodium borohydride is added in portions within 4 days at a reaction temperature of 65° C. The reaction mixture is mixed with 20 ml of saturated NaCl solution after cooling to room temperature, stirred for 1 hour at room temperature, filtered on Celite, and rewashed with ethyl acetate and tetrahydrofuran. The organic phase is separated, washed with saturated NaCl solution, dried and concentrated by evaporation. Column chromatography on silica gel with hexane-ethyl acetate yields 68 mg of the product as a mixture of the two possible diastereomers.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Germany Patent Application No. 102 15 316.7, filed Apr. 2, 2002, and U.S. Provisional Application Ser. No. 60/369,583, filed Apr. 4, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula I

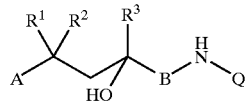

(I)

wherein

A stands for an aryl group, a benzyl group or a phenethyl group, optionally substituted by;
one or more radicals of $C_1$–$C_5$-alkyl, $C_1$–$C_5$-alkoxy, $C_1$–$C_5$-alkylthio, $C_1$–$C_5$-perfluoroalkyl, halogen, hydroxy, cyano, or nitro; or
—O—(CH$_2$)$_n$—O—, —O—(CH$_2$)$_n$—CH$_2$—, —O—CH=CH—, or —(CH$_2$)$_{n+2}$—, wherein n=1 or 2, and wherein the two terminal atoms in these groups are linked with directly adjacent ring-carbon atoms of the aryl, benzyl or phenethyl group to form a fused ring;
or
NR$^4$R$^5$, wherein R$^4$ and R$^5$, independently of one another, are hydrogen, $C_1$–$C_5$-alkyl or (CO)—$C_1$–$C_5$-alkyl, R$^1$ and R$^2$, independently of one another, are a hydrogen atom, a methyl or an ethyl group or together with the carbon atom of the chain from a $C_3$–$C_6$-cycloalkyl ring, R$^3$ means a $C_1$–$C_3$-alkyl group or a $C_1$–$C_3$-alkyl group optionally partially or completely fluorinated, B means a methylene group that is optionally substituted by a methyl, an ethyl, or a carbonyl group, and Q means a quinolinyl group or an isoquinolinyl group that is linked via any position and that optionally can be substituted by one or more radicals from the group $C_1$–$C_5$-alkyl, wherein $C_1$–$C_5$-alkyl is optionally substituted by 1–3 hydroxy groups and/or 1–3 COOR$^6$ groups; $C_1$–$C_5$-alkoxy; $C_1$–$C_5$ alkylthio; $C_1$–$C_5$-perfluoroalkyl; halogen; hydroxy; a carbonyl-oxygen atom; cyano; nitro; or NR$^4$R$^5$,
wherein R$^4$ and R$^5$, independently of one another, are hydrogen, $C_1$–$C_5$-alkyl or (CO)—$C_1$–$C_5$-alkyl;
COOR$^6$, wherein R$^6$ means hydrogen or a $C_1$–$C_5$-alkyl group;
(CO)NR$^7$R$^8$, wherein R$^7$ and R$^8$, independently of one another, mean hydrogen or a $C_1$–$C_5$-alkyl group;
or a ($C_1$–$C_5$-alkylen)-O—(CO)—($C_1$–$C_5$)alkyl group; wherein, the $C_1$–$C_5$-alkyl groups in A, and R$^4$–R$^8$ are optionally substituted by 1–3 hydroxy groups and/or 1–3 COOR$^6$ groups;

or a racemate, a separately present stereoisomer, or a physiologically compatible salt thereof.

2. Compounds according to claim 1, wherein Q means a quinolinyl group or an isoquinolinyl group that is linked via any position and that optionally can be substituted by one or more radicals from the group $C_1$–$C_5$-alkyl, a carbonyl-oxygen atom, COOR$^6$, wherein R$^6$ means hydrogen or a $C_1$–$C_5$-alkyl group, (CO)NR$^7$R$^8$, wherein R$^7$ and R$^8$, independently of one another, mean hydrogen or a $C_1$–$C_5$-alkyl group, or a ($C_1$–$C_5$-alkylene)-O—(CO)—($C_1$–$C_5$)alkyl group, wherein the $C_1$–$C_5$-alkyl optionally can be substituted by 1–3 hydroxy groups or 1–3 COOR$^6$ groups.

3. A compound of formula I

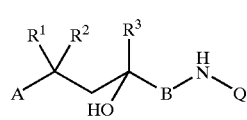

(I)

wherein

A stands for an aryl group, a benzyl group or a phenethyl group, optionally substituted by;
one or more radicals of $C_1$–$C_5$-alkyl, $C_1$–$C_5$-alkoxy, $C_1$–$C_5$-alkylthio, $C_1$–$C_5$-perfluoroalkyl, halogen, hydroxy, cyano, or nitro; or
—O—(CH$_2$)$_n$—O—, —O—(CH$_2$)$_n$—CH$_2$—, —O—CH=CH—, or —(CH$_2$)$_{n+2}$—, wherein n=1 or 2, and wherein the two terminal atoms in these groups are linked with directly adjacent ring-carbon atoms of the aryl, benzyl or phenethyl group to form a fused ring;
or
NR$^4$R$^5$,
wherein R$^4$ and R$^5$, independently of one another, are hydrogen, $C_1$–$C_5$-alkyl or (CO)—$C_1$–$C_5$-alkyl, R$^1$ and R$^2$, independently of one another, mean a hydrogen atom, a methyl or an ethyl group or together with the carbon atom of the chain form a $C_3$–$C_6$-cycloalkyl ring, R$^3$ means a $C_1$–$C_3$-alkyl group or a $C_1$–$C_3$-alkyl group optionally partially or completely fluorinated, B means a methylene group that is optionally substituted by a methyl, an ethyl, or a carbonyl group, and Q means a quinolinyl group or an isoquinolinyl group that is linked via any position and that optionally can be substituted by one or more radicals from the group $C_1$–$C_5$-alkyl, $_1$–$C_5$-alkoxy, $C_1$–$C_5$-perfluoroalkyl, halogen, hydroxy, cyano, nitro or NR$^4$R$^5$,
wherein R$^4$ and R$^5$, independently of one another, can be hydrogen, $C_1$–$C_5$-alkyl or (CO)—$C_1$–$C_5$-alkyl, or a racemate, a separately present stereoisomer or a physiologically compatible salt.

4. A compounds according to claim 2, wherein B means a methylene group.

5. A compounds according to claim 2, wherein A is an aryl radical.

6. A compounds according to claim 5, wherein A is an aryl radical optionally substituted by one or more radicals from the group $C_1$–$C_5$-alkyl, $C_1$–$C_5$-alkoxy, $C_1$–$C_5$-perfluoroalkyl, halogen, hydroxy, or nitro, or
—O—$(CH_2)_n$—O—, —O—$(CH_2)_n$—$CH_2$—, —O—CH=CH—, or —$(CH_2)_{n+2}$—, wherein n=1 or 2, and their terminal atoms in these groups are linked with immediately adjacent ring-carbon atoms.

7. A compound according to claim 2, wherein $R^1$ and $R^2$ together with the carbon atom of the chain mean a $C_3$–$C_6$-cycloalkyl ring.

8. A compounds according to claim 2, wherein Q means an optionally substituted quinolinyl group that is linked via any position.

9. A compound according to claim 5, wherein A is a phenyl radical that is substituted by a hydroxy group, or a methoxy group, or a halogen atom.

10. A compounds according to claim 1, wherein the compound is (+)-enantiomer.

11. A compound according to claim 1, wherein the compound is (−)-enantiomer.

12. A pharmaceutical composition comprising a compound according to claim 1, and a pharmaceutically acceptable vehicle.

13. A method of treating an inflammatory disease, comprising administrating an effective amount of a compound according to claim 1 to a patient in need thereof.

14. A compound according to claim 5, wherein A is phenyl or naphthyl.

15. A compound according to claim 1, wherein the $C_1$–$C_5$ alkyl groups in A, $R^4$, $R^5$, $R^6$, $R^7$, and $R^8$ are, independently, a methyl, an ethyl, an n-propyl, an iso-propyl, an n-butyl, an iso-butyl, a tert-butyl, an n-pentyl, a 2,2-dimethylpropyl, a 2-methylbutyl, or a 3-methylbutyl group, optionally substituted by hydroxy.

16. A compound according to claim 1, wherein $R^1$ and $R^2$ are together a cyclopropyl ring.

17. A compound according to claim 1, wherein B is a methylene group.

18. A compound according to claim 1, wherein the $C_1$–$C_5$ alkoxy group in A and Q is a methoxy or an ethoxy group.

19. A compound according to claim 1, wherein the $C_1$–$C_5$-alkylthio group in A and Q is a methylthio or an ethylthio group.

20. A compound according to claim 1, wherein Q is a quinoline ring linked at the 4-, 5- or 8-position or an isoquinoline ring linked at the 1-position.

* * * * *